Figure 1A:
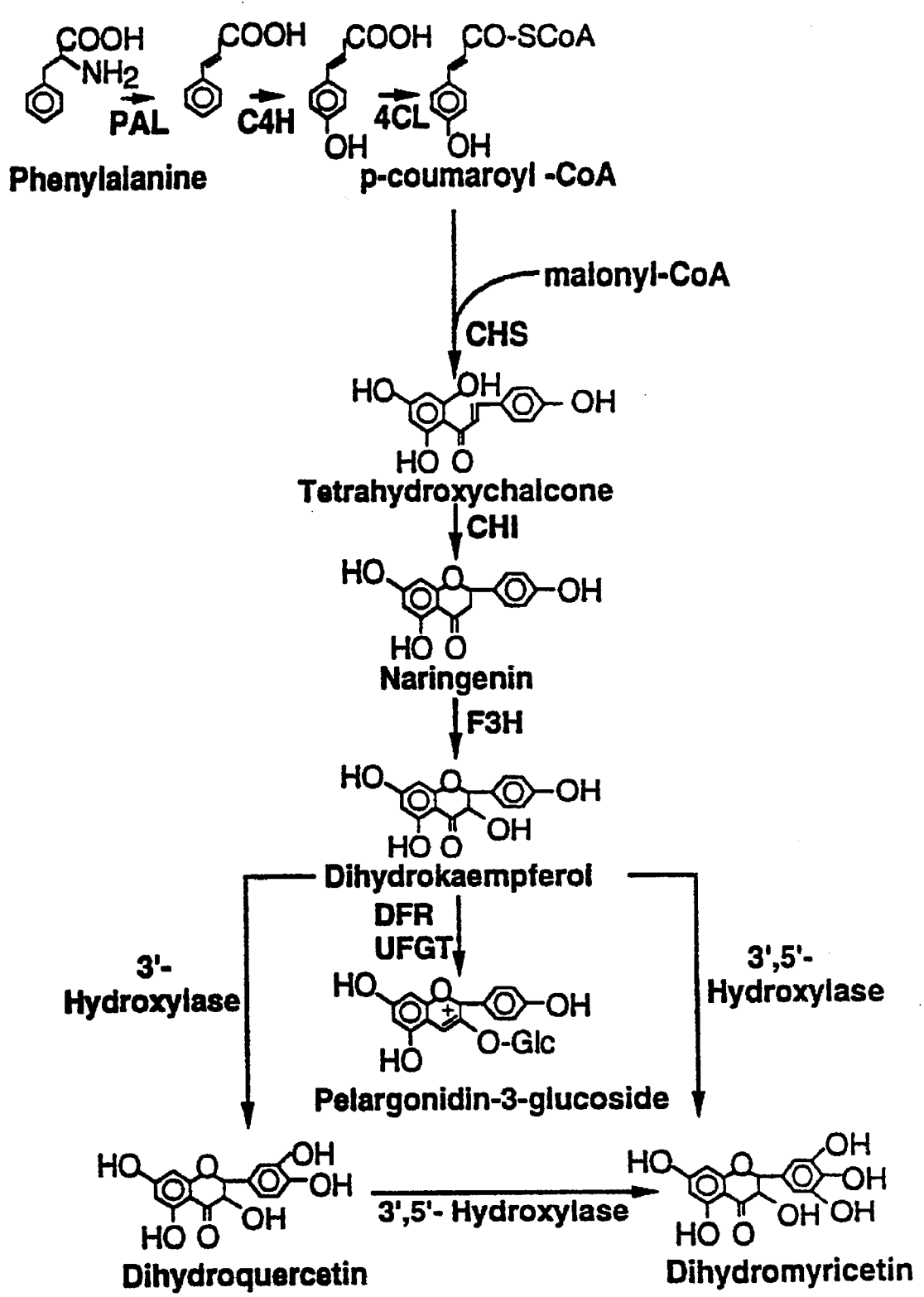

United States Patent [19]
Holton et al.

[11] Patent Number: 5,639,870
[45] Date of Patent: Jun. 17, 1997

[54] GENETIC SEQUENCES ENCODING FLAVONOID PATHWAY ENZYMES AND USES THEREFOR

[75] Inventors: Timothy Albert Holton, Northcote; Edwina Cecily Cornish, Upper Beaconsfield; Yoshikazu Tanaka, Rosanna, all of Australia

[73] Assignee: International Flower Developments Pty., Ltd., Victoria, Australia

[21] Appl. No.: 313,075

[22] PCT Filed: Mar. 25, 1993

[86] PCT No.: PCT/AU93/00127
§ 371 Date: Nov. 30, 1994
§ 102(e) Date: Nov. 30, 1994

[87] PCT Pub. No.: WO93/20206
PCT Pub. Date: Oct. 14, 1993

[30] Foreign Application Priority Data

Mar. 27, 1992 [AU] Australia ............... PL1538/92
Jan. 7, 1993 [AU] Australia ............... PL6698/93

[51] Int. Cl.$^6$ ............................................ C12N 15/29
[52] U.S. Cl. ............... 536/23.2; 800/205; 800/DIG. 67; 800/DIG. 68
[58] Field of Search ............... 435/172.3, 320.1, 435/69.1; 536/23.2, 24.3; 530/370; 800/205, DIG. 67, 68

[56] References Cited

U.S. PATENT DOCUMENTS 5,231,020  7/1993  Jorgensen et al. ............... 435/172.3

OTHER PUBLICATIONS

Britsch et al. (1992) "Molecular Cloning, Sequence Analysis and in vitro Expression of Flavanone 3β–Hydroxylase from *Petunia hybrida*", *The Journal of Biological Chemistry* 267, 5380–5387.

Bozak, et al. (May 1990) Proc. Natl. Acad. Sci. 87: 3904–3908.

Fugua, et al (1990) Biotechniques 9 (2):206–210.

*Primary Examiner*—Che S. Chereskin
*Attorney, Agent, or Firm*—Scully, Scott, Murphy & Presser

[57] ABSTRACT

The present invention relates to a nucleic acid isolate comprising a sequence of nucleotides encoding, or complementary to a sequence encoding, a flavonoid 3'-hydroxylase or a functional derivative thereof. The present invention also relates to transgenic plants carrying and/or expressing the above-mentioned nucleic acid material.

6 Claims, 28 Drawing Sheets pCGP 142

FIGURE 2B

```
 F   S   S   I   R   N   D   E   I   S   S   L
TTT AGT TCA ATT CGG AAT GAT GAG ATT TCG AGT CTC
        ——————————▶

I   S   S   I   H   S   M   N   G   S   V   V
ATT TCA TCA ATT CAT TCC ATG AAC GGT TCT GTT GTC

N   M   T   Q   K   I   L   C   F   T   N   S
AAC ATG ACA CAA AAG ATT CTT TGT TTT ACA AAC TCT

V   T   C   R   T   A   F   G   K   V   Y   K
GTG ACT TGT AGA ACA GCT TTC GGG AAA GTA TAC AAA

N   Q   N   E   L   I   N   L   M   R   E   V
AAT CAA AAT GAA TTG ATA AAC TTG ATG AGG GAA GTA

L   E   L   V   G   G   F   D
CTG GAA TTA GTA GGA GGA TTT GAT  ---------------

F   E   N   S   P   V   E   F   I   G   N   H
TTT GAA AAT TCT CCG GTT GAG TTT ATT GGA AAT CAC

F   E   L   V   P   F   G   A   G   K   R   I
TTT GAG CTT GTT CCG TTT GGT GCA GGA AAA AGG ATT

C   P   G   M   Q   F   G   L   A   N   I   R
TGT CCA GGA ATG CAA TTT GGT TTA GCT AAT ATT AGA

H   P   L   A   R   F   L   Y   H   F   N   W
CAT CCT TTG GCT CGA TTC CTC TAC CAT TTT AAC TGG

A   L   P   Y   E   T   N   P   E   D   L   D
GCG CTT CCA TAT GAA ACT AAT CCT GAA GAT TTA GAT

S   L   K   N   M   D
AGT CTG AAA AAT ATG GAT TAA GTGCAGCAAAAGAGAAAGA
                                 ◀——————————————
TCTATACTTAATTGCCGTAGATCACAAAGAAGGTGATATATAAATTC
TGATGTTCTGCTTTAAATGGTGAAAGTCATACTCTACACAATGCTTC
ATCTCCTTAATTTGAGTTTGGTGTACATTTGTGTCTCCCTTTTAGCT
TTGAATTTCACCTTGAAAAATGATCACATTTTCTTTTTCTGTTACTC
CAATTAAGATATATGTTGTGGTTGGTCAATTATGCCATATTTATCAA
AAGATCAAATCAATTCCCTCGTTGATAAGTATAGATTATAAAACTGA
TTAATGAATCAAAAAAAAAAAAAAAAAA
```

FIGURE 2C pCGP147

```
        Q   F   F   N   L   V   S   F   L   L   I   V   F   S   L
     TGCAATTTTCAACTTGGTTTCCTTTCTCCTTATTGTATTTTCCCTC
            10          20          30          40
     ──────────────────────▶

I   S   L   R   K   W   K   K   S   N   C   Q   T   K   K   L
     ATTTCATTAAGAAAATGGAAGAAATCCAATTGTCAAACCAAAAAATTG
            58          68          78          88

P   P   G   P   W   K   V   P   F   L   G   S   L   L   H   M
     CCTCCAGGCCCATGGAAAGTACCTTTTCTTGGAAGCTTGCTTCATATG
            106         116         126         136

V   G   G   L   P   H   H   V   L   R   D   L   A   K   K   Y
     GTAGGTGGACTTCCACACCATGTCCTTAGAGATTTAGCCAAAAAATAT
            154         164         174         184

G   P   I   M   H   L   Q   L   G   K   I   S   A   V   V   V
     GGACCAATTATGCACCTTCAACTAGGTAAAATTTCTGCCGTTGTAGTT
            202         212         222         232

T   S   P   E   M   A   R   K   V   L   K   T   H   D   L   A
     ACTTCTCCTGAGATGGCAAGAAAAGTACTAAAAACTCATGACCTTGCA
            250         260         270         280

F   A   Y   R   P   K   L   L   G   I   E   I   V   C   Y   N
     TTTGCATATAGGCCTAAACTTCTAGGCATTGAGATTGTCTGCTATAAT
            298         308         318         328

S   S   D   I   A   F   S   P   Y   G   D   Y   W   R   Q   M
     AGTTCAGACATTGCCTTTTCCCCGTATGGTGATTACTGGAGGCAAATG
            346         356         366         376

R   K   I   C   V   L   E   V   L   S   A   K   N   V   R   S
     CGTAAAATTTGTGTATTGGAAGTGCTTAGTGCCAAAAATGTCCGGTCA
            394         404         414         424

F   N   S   I   R   R   D   E   I   L   L   M   I   D   F   L
     TTTAACTCGATTAGACGAGATGAAATACTTCTTATGATCGATTTTTTG
            442         452         462         472

R   S   S   S   G   K   P   V   N   I   T   E   R   I   F   S
     CGATCATCTTCTGGTAAGCCAGTTAATATAACAGAAAGGATCTTTTCA
            490         500         510         520
```

FIGURE 2D

```
       F   T   S   S   M   I   C   R   S   V   F   G   K   R   I   K
     TTCACAAGCTCTATGATTTGTAGATCAGTATTTGGGAAAAGAATAAAG
          538         548         558         568

E   K   D   E   C   I   R   H   V   K   K   M   T   G   L   I
     GAGAAAGACGAATGTATACGACATGTGAAAAAAATGACAGGCTTAATA
          586         596         606         616

D   G   F   D   V   A   D   I   F   P   S   L   R   F   L   H
     GATGGGTTCGATGTGGCTGACATATTCCCTTCGTTGAGGTTTCTTCAT
          634         644         654         664

V   L   I   G   M   K   G   K   I   M   D   V   H   R   K   V
     GTACTAATCGGTATGAAGGGTAAAATTATGGATGTTCATCGTAAGGTA
          682         692         702         712

D   A   I   V   E   E   V   M   N   E   H   K   E   T   L   R
     GATGCTATTGTTGAGGAAGTCATGAATGAGCACAAAGAAACTCTTCGA
          730         740         750         760

T   G   K   T   N   G   E   V   G   G   E   D   L   I   D   V
     ACTGGCAAGACCAATGGTGAAGTGGGAGGAGAAGATTTAATTGATGTA
          778         788         798         808

L   L   R   L   K   E   E   G   D   L   Q   L   P   I   T   N
     TTGCTAAGACTTAAGGAAGAGGGAGACCTTCAACTTCCAATCACAAAT
          826         836         846         856

D   N   I   K   A   I   F   N   D   M   F   A   A   G   T   E
     GACAACATCAAAGCCATTTTTAATGACATGTTTGCTGCGGGAACAGAA
          874         884         894         904

T   S   S   T   T   I   N   W   A   M   V   E   L   M   K   N
     ACTTCATCAACAACAATTAACTGGGCCATGGTAGAACTGATGAAAAAT
          922         932         942         952

P   S   V   F   A   K   A   Q   A   E   V   R   E   V   F   K
     CCAAGTGTATTCGCGAAAGCTCAAGCAGAGGTAAGAGAAGTCTTCAAA
          970         980         990        1000

G   K   E   T   F   D   E   D   D   I   E   E   L   N   Y   L
     GGGAAAGAAACTTTCGATGAAGATGATATCGAGGAGCTGAATTACCTT
         1018        1028        1038        1048

K   L   V   I   R   E   T   L   R   L   H   P   P   L   P   L
     AAGTTAGTCATTAGAGAAACTTTAAGACTCCACCCTCCACTTCCACTT
         1066        1076        1086        1096
```

```
  L   L   P   R   E   C   R   R   E   T   E   I   N   G   Y   T
TTGCTTCCAAGAGAATGTCGGAGAGAAACAGAAATAAATGGCTACACT
     1114      1124      1134      1144

I   P   L   N   T   K   V   I   V   N   V   W   A   I   G   R
ATTCCTTTAAATACCAAAGTCATAGTTAATGTTTGGGCTATTGGAAGA
     1162      1172      1182      1192

D   P   K   Y   W   D   D   A   E   S   F   K   P   E   R   F
GATCCAAAATATTGGGATGATGCAGAAAGCTTTAAGCCTGAGAGATTT
     1210      1220      1230      1240

E   H   N   S   L   N   F   A   G   N   N   F   E   Y   L   P
GAACATAACTCTTTGAATTTTGCTGGCAATAATTTTGAATATCTTCCT
     1258      1268      1278      1288

F   G   S   G   R   R   I   C   P   G   I   S   F   G   L   A
TTTGGTAGTGGAAGGAGGATTTGCCCCGGAATATCATTTGGTTTAGCT
     1306      1316      1326      1336

N   V   Y   H   P   L   A   Q   L   L   Y   H   F   D   W   R
AATGTTTATCATCCATTGGCTCAATTGTTGTATCATTTCGATTGGAGA
     1354      1364      1374      1384

L   P   T   G   V   D   P   N   D   F   E   L   T   S   *
CTTCCTACTGGGGTCGACCCAAATGACTTTGAATTGACTAGTTAGCTG
          1402      1412      1422      1432
       ←————————

GAGTAACTACTGGTAGGAAAAGAGACCTTTACTTGATTTTCACTCCTT
       1450      1460      1470      1480

ATTCACCTTCTCTAAAGTGATTAAATGG-GCAAATTTTAATTTGAAAT
     1498      1508      1518      1528

AATACTTTTTCTTGTTTACATTTCTCTCCCATTGTTGTATTTCATTTA
     1546      1556      1566      1576

CCTATTGTTGTACTTCTTTCTTTTGTTGATGTCTTAGGTTTTACCTAT
     1594      1604      1614      1624

TTCTATGCATTTGTATTTAAAAAAAAAAAAAAAAA
     1642      1652      1662
```

FIGURE 2E

FIGURE 2F pCGP158

| Gly | Met | Met | Lys | Gln | Gly | Asp | Phe | Leu | Asp | Val | Leu |
|-----|-----|-----|-----|-----|-----|-----|-----|-----|-----|-----|-----|
| GGG | ATG | ATG | AAG | CAA | GGA | GAT | TTC | TTG | GAT | GTA | CTT |

| Leu | Asp | Gln | Cys | Asp | Glu | Glu | Gly | Ser | Gly | Phe | Asp |
| CTT | GAT | CAA | TGT | GAT | GAA | GAA | GGG | TCT | GGA | TTT | GAT |

| Arg | Gln | Thr | Ile | Lys | Pro | Leu | Ile | Leu | Asp | Leu | Phe |
| CGC | CAA | ACT | ATC | AAG | CCT | CTC | ATC | CTG | GAT | TTA | TTC |

| Ile | Ala | Gly | Ser | Asp | Thr | Ser | Ala | Ile | Thr | Thr | Glu |
| ATT | GCT | GGA | AGT | GAT | ACA | TCT | GCC | ATA | ACA | ACA | GAA |

| Trp | Ala | Met | Ala | Glu | Leu | Leu | Arg | Lys | Pro | Gln | Glu |
| TGG | GCA | ATG | GCA | GAA | CTA | CTT | CGA | AAA | CCT | CAA | GAA |

----------------------------------------------------
----------------------------------------------------

| Phe | Val | Asn | Ala | Trp | Ala | Ile | Gly | Arg | Asp | Pro | Lys |
| TTT | GTG | AAT | GCA | TGG | GCA | ATT | GGA | AGA | GAT | CCA | AAA |

| Tyr | Trp | Glu | Lys | Pro | Leu | Glu | Phe | Met | Pro | Glu | Arg |
| TAC | TGG | GAA | AAA | CCA | CTG | GAG | TTT | ATG | CCT | GAA | AGA |

| Phe | Leu | Lys | Cys | Ser | Leu | Asp | Tyr | Lys | Gly | Arg | --- |
| TTC | TTG | AAG | TGT | AGT | TTG | GAT | TAC | AAA | GGT | AGG | G-- |

| Phe | Glu | Tyr | Ile | Pro | Phe | Gly | Ala | Gly | Arg | Arg | Ile |
| TTT | GAG | TAT | ATA | CCA | TTT | GGC | GCA | GGT | CGA | AGA | ATT |

| Cys | Pro | Gly | Met | Pro | His | Cys | Asn | Lys | Asp | Gly | Glu |
| TGT | CCT | GGA | ATG | CCA | CAT | TGC | AAT | AAG | GAT | GGT | GAA |

| Phe | Asp | Ala | Gly | Phe | Asp | Tyr | Ser | Pro | Phe | Ser | Trp |
| TTT | GAT | GCT | GGC | TTC | GAT | TAT | TCA | CCA | TTT | AGT | TGG |

| Glu | Leu | Pro | --- | Gly | Met | Ala | Pro | Lys | --- | Leu | Asn |
| GAA | TTA | CCT | -AA | GGA | ATG | GCA | CCA | AAG | -AT | TTG | AAC |

| Met | Glu | Glu | Gln | Phe | Gly | Val | Thr | Leu | Arg | Lys | Ala |
| ATG | GAG | GAA | CAG | TTT | GGA | GTT | ACC | TTG | AGG | AAG | GCT |

| Ile | Pro | Leu | Ile | Ala | Ile | Pro | Ser | Met | Glu | Glu | Lys |
| ATT | CCC | CTT | ATT | GCC | ATT | CCC | AGT | ATG | GAA | GAA | AAG |

| Val | Ile | Phe |
| GTC | ATA | TTT | TAG CCCAAAAGCTATGCATTTTGTGTGTATGTTT

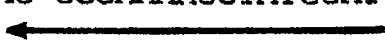

FIGURE 2G pCGP 160

```
    K   Q   I   N   A   L   L   V   E   I   F   G
    AAA CAG ATC AAT GCA TTG CTT GTG GAA ATA TTT GGA
    ─────────────────────────────────▶

A   G   T   E   S   T   T   A   T   S   Q   W
    GCT GGT ACA GAA TCT ACA ACT GCT ACA AGC CAA TGG

M   L   V   E   L   L   R   N   R   Q   A   L
    ATG CTT GTA GAA CTC CTT AGA AAT CGA CAA GCC TTG

─────────────   P   K   D   T   Q   V   M   V   N
    ─────────────CCC AAA GAC ACT CAA GTT ATG GTA AAC

E   W   A   I   A   Y   D   P   K   I   W   G
    GAG TGG GCG ATT GCG TAT GAT CCT AAG ATT TGG GGC

S   F   K   P   Q   R   F   I   D   S   K   I
    AGC TTC AAA CCC GAA AGG TTT ATC GAT TCA AAA ATA

D   P   L   D   H   K   G   Q   N   F   E   Y
    GAT CCT TTG GAC CAC AAA GGG CAA AAT TTT GAA TAT

F   P   F   G   S   G   R   R   I   C   A   G
    TTT CCT TTT GGT TCT GGA AGG AGA ATT TGT GCT GGA

E   P   L   A   S   R   V   I   P   L   A   V
    GAA CCT TTG GCT TCT AGG GTT ATT CCC TTA GCT GTT

A   S   M   I   H   K   F   ─────────
    GCT TCT ATG ATC CAT AAG TTT ─────────GATATCACTAT
                                ◀─────────
GTTAGAAGATCCACTCTCATCATTCCTAAGTTGAGAAGAGTGAGGAA

ATTAAAAGAAGCAGAAGATATGTTACTATAAAAACTCGTTATATATA

TATATATTGCTGTATCTATATATGTGTGAATGATCTGCTGCTCATGT

TGTGTTTTGTTGTTTGTGTACTATAGGTCATACCTAAGTTGATGAAA

TGTCTCTGAGAATATATACTCCTTATATAATAGGAGTAATTTACCGA

TAATTAATATTCCTGCGACAAAAAAAAAAAAAAAAA
``` pCGP454

FIGURE 2H

```
    -   R   E   S   M   E   D   V   R   L   L   G
   CT CGA GAA TCA ATG GAA GAT GTA AGA TTA CTA GGC
   ───────────▶

Y   H   I   P   A   K   T   R   L   F   I   N
   TAT CAC ATA CCT GCT AAA ACG AGA CTC TTT ATC AAT

A   W   T   M   G   R   D   P   L   T   W   E
   GCT TGG ACA ATG GGG AGA GAC CCA CTA ACA TGG GAA

N   P   E   E   Y   Q   P   E   R   F   L   N
   AAT CCA GAA GAG TAT CAG CCA GAG AGA TTC TTG AAT

R   D   T   D   V   K   G   V   N   F   E   F
   AGA GAT ACT GAT GTC AAA GGA GTA AAC TTT GAG TTC

I   P   F   G   A   G   R   S
   ATT CCC TTT GGC GCC GGC AGA AGC
                            ◀───────────
```

FIGURE 3A pCGP 602

```
CTTTCTACTAGCTACTTCGTTATATATATGTAAAATTGTGACTTT
     10        20        30        40

GAAAATCATTTAAATTATCATAAGGTTCATTTTATCTTGATCAAA
     55        65        75        85
```

```
                                         M  M  L
ATATTTACTTCGGCCATATACGTTTTCCTTTAGTCATGATGCTAC
    100       110       120       130
```

```
 L  T  E  L  G  A  A  T  S  I  F  L  I  A  H
TTACTGAGCTTGGTGCAGCAACTTCAATCTTTCTAATAGCACACA
    145       155       165       175
```

```
 I  I  I  S  T  L  I  S  K  T  T  G  R  H  L
TAATCATTTCAACTCTTATTTCAAAAACTACCGGCCGGCATCTAC
    190       200       210       220
```

```
 P  P  G  P  R  G  W  P  V  I  G  A  L  P  L
CGCCGGGGCCAAGAGGGTGGCCGGTGATCGGAGCACTTCCACTTT
    235       245       255       265
```

```
 L  G  A  M  P  H  V  S  L  A  K  M  A  K  K
TAGGAGCCATGCCACATGTTTCCTTAGCTAAAATGGCAAAAAAAT
    280       290       300       310
```

```
 Y  G  A  I  M  Y  L  K  V  G  T  C  G  M  A
ATGGAGCAATCATGTATCTCAAAGTTGGAACATGTGGCATGGCAG
    325       335       345       355
```

```
 V  A  S  T  P  D  A  A  K  A  F  L  K  T  L
TTGCTTCTACCCCTGATGCTGCTAAAGCATTCTTGAAAACACTTG
    370       380       390       400
```

```
 D  I  N  F  S  N  R  P  P  N  A  G  A  T  H
ATATCAACTTCTCCAATCGTCCACCTAATGCAGGTGCCACTCACT
    415       425       435       445
```

```
 L  A  Y  N  A  Q  D  M  V  F  A  H  Y  G  P
TAGCTTATAATGCTCAAGACATGGTTTTTGCACATTATGGACCAC
    460       470       480       490
```

```
 R  W  K  L  L  R  K  L  S  N  L  H  M  L  G
GATGGAAGTTGCTAAGGAAATTAAGCAACTTGCATATGCTAGGGG
    505       515       525       535
```

FIGURE 3B

```
  G   K   A   L   E   N   W   A   N   V   R   A   N   E   L
GAAAAGCCTTAGAGAATTGGGCAAATGTTCGTGCCAATGAGCTAG
        550         560         570         580

G   H   M   L   K   S   M   S   D   M   S   R   E   G   Q
GGCACATGCTAAAATCAATGTCCGATATGAGTCGAGAGGGCCAGA
        595         605         615         625

R   V   V   V   A   E   M   L   T   F   A   M   A   N   M
GGGTTGTGGTGGCGGAGATGTTGACATTTGCCATGGCCAATATGA
        640         650         660         670

I   G   Q   V   M   L   S   K   R   V   F   V   D   K   G
TCGGACAAGTGATGCTAAGCAAAAGAGTATTTGTAGATAAAGGTG
        685         695         705         715

V   E   V   N   E   F   K   D   M   V   V   E   L   M   T
TTGAGGTAAATGAATTTAAGGACATGGTTGTAGAGTTAATGACAA
        730         740         750         760

I   A   G   Y   F   N   I   G   D   F   I   P   C   L   A
TAGCAGGGTATTTCAACATTGGTGATTTTATTCCTTGTTTAGCTT
        775         785         795         805

W   M   D   L   Q   G   I   E   K   R   M   K   R   L   H
GGATGGATTTACAAGGGATAGAAAAACGAATGAAACGTTTACATA
        820         830         840         850

K   K   F   D   A   L   L   T   K   M   F   D   E   H   K
AGAAGTTTGATGCTTTATTGACAAAGATGTTTGATGAACACAAAG
        865         875         885         895

A   T   T   Y   E   R   K   G   K   P   D   F   L   D   V
CAACTACCTATGAACGTAAGGGGAAACCAGATTTTCTTGATGTTG
        910         920         930         940

V   M   E   N   G   D   N   S   E   G   E   R   L   S   T
TTATGGAAAATGGGGACAATTCTGAAGGAGAAAGACTCAGTACAA
        955         965         975         985

T   N   I   K   A   L   L   N   L   F   T   A   G   T
CCAACATCAAAGCACTTTTGCTGAATTTGTTCACAGCTGGTACGG
        1000        1010        1020        1030
```

FIGURE 3C

```
        D   T   S   S   S   A   I   E   W   A   L   A   E   M   M
       ACACTTCTTCTAGTGCAATAGAATGGGCACTTGCAGAAATGATGA
            1045        1055        1065        1075

K   N   P   A   I   L   K   K   A   Q   A   E   M   D   Q
       AGAACCCTGCCATTTTGAAAAAGCACAAGCAGAAATGGATCAAG
            1090        1100        1110        1120

V   I   G   R   N   R   R   L   L   E   S   D   I   P   N
       TCATTGGAAGAAATAGGCGTTTACTCGAATCCGATATCCCAAATC
            1135        1145        1155        1165

L   P   Y   L   R   A   I   C   K   E   T   F   R   K   H
       TCCCTTACCTCCGAGCAATTTGCAAAGAAACATTTCGAAAACACC
            1180        1190        1200        1210

P   S   T   P   L   N   L   P   R   I   S   N   E   P   C
       CTTCTACACCATTAAATCTTCCTAGGATCTCGAACGAACCATGCA
            1225        1235        1245        1255

I   V   D   G   Y   Y   I   P   K   N   T   R   L   S   V
       TAGTCGATGGTTATTACATACCAAAAAACACTAGGCTTAGTGTTA
            1270        1280        1290        1300

N   I   W   A   I   G   R   D   P   Q   V   W   E   N   P
       ACATATGGGCAATTGGAAGAGATCCCCAAGTTTGGGAAAATCCAC
            1315        1325        1335        1345

L   E   F   N   P   E   R   F   L   S   G   R   N   S   K
       TAGAGTTTAATCCCGAAAGATTCTTGAGTGGAAGAAACTCCAAGA
            1360        1370        1380        1390

I   D   P   R   G   N   D   F   E   L   I   P   F   G   A
       TTGATCCTCGAGGGAACGATTTTGAATTGATACCATTTGGTGCTG
            1405        1415        1425        1435

G   R   R   I   C   A   G   T   R   M   G   I   V   M   V
       GACGAAGAATTTGTGCAGGAACAAGAATGGGAATTGTAATGGTGG
            1450        1460        1470        1480

E   Y   I   L   G   T   L   V   H   S   F   D   W   K   L
       AATATATATTAGGAACTTTGGTTCATTCATTTGATTGGAAATTAC
            1495        1505        1515        1525
```

FIGURE 3D

```
P   S   E   V   I   E   L   N   M   E   E   A   F   G   L
CAAGTGAAGTTATTGAGTTGAATATGGAAGAAGCTTTTGGCTTAG
     1540       1550       1560       1570

A   L   Q   K   A   V   P   L   E   A   M   V   T   P   R
CTTTGCAGAAAGCTGTCCCTCTTGAAGCTATGGTTACTCCAAGGT
     1585       1595       1605       1615

L   Q   L   D   V   Y   V   P   *
TACAATTGGATGTTTATGTACCATAGCTATAGATGTGTATTGTGC
     1630       1640       1650       1660

TATAATTGCGCATGTTGTTGGTTGTAGCATGAGATATTAAAAGGA
     1675       1685       1695       1705

GTACATGAAGCGCATTGCATGAGTTTAACTTGTAGCTCCTTAATA
     1720       1730       1740       1750

TTTTAGGTATTTTTCAATTAATAAGTTCTTGTTGGTTGGGTAAAA
     1765       1775       1785       1795

AAAAAAAAAAAA
     1810
```

FIGURE 4A

1) pCGP161

CCAGACACCCACAAACTTCCATACCTTCAGGCTGTGATCAAGGAGACTCT
TCGTCTCCGGATGGCAATTCCTCTATTAGTCCCACACATG----------
----------------------AAACTTTACAGAAAACGTTCATCTTTTT
ATGTCATATCAAGTCTTCTTGGACTGGTTCGTTATTACACCTACCTATCT
GAATGTATTTTT

2) pCGP162

ACGAACATGGGAAAATCCAGAAGAGTATCAGCCAGAGAGATTCTTGAATA
GTGATATTGATGTCAAAGGACTAAACTTTGAGTTGATTCC----------
---ATGGCTAGTAGCTACTTCTTTCATGATATCTGTAATAAGTGTAGTGC
TCGACTCCTTCAGGCGAGTTGTGTGTTTAATTTCTCCAGTATC

3) pCGP163

AAGTTCTTTCCATCAGTTATCAAACAAACCATGAGGCTGCATCCCCCTCT
CCCTTTATTACTATTAAGGGAAAGCAAGGAATCTTGTGAA----------
--------GATAGGGAGCGGTTTACTCCCTTCGTGGCCTTACCATTACACT
AACAATGAATGGGCTTGGAAATAGTCTCAGATGTTTTAAAGAAAAC

4) pCGP165

GTGATTTTCCAAAAGAATCTCACTTGCTGCAGATGTCCTATGTTCAAGCC
TGTGTGAAGGAAACTCTTAGGTTGCATCCTCCGGCGCCAT----------
-----TATTTATTGAAGTTGAGAAACTTATGTATGAAAGTGTCATACAGA
ACTACTGCCCATGTGGTGTGTTTAGTACTTCTTTTTTTTGGGT

5) pCGP166

ATGTCCTATGTTCAAGCCTGTGTGCCGGAAACTCTTAGGTTGCATCCTCC
GGCGCCATTGCTACTTCCACATGCGTGCAATCGAAACATG----------
-------------------TCCCCCTGGATTTGTACACTAGATACAAGACTT
AGCGGTCCTGGTGTAATCTCAATTCTCATGTGGTTATAAACAGAAGTTCT
TCTGGTG

6) pCGP167

GAAACATTATCAATGAACATGTTAAGAATCGAGCACTCGGAAGCAAGGGA
AATGGTGCGTTTGGAGGTGAAGATTTGGTTGATGTTTTAC----------
--------GGTTGGGGTAAATTGGGGCCCCCCTTTTAAGGCTTTGGAATTT
CCACCTGGAAAAATGGACCCCATTTTCCTTTTCCTGTACCTCCAATT

FIGURE 4B

7) pCGP168

AAAACTGCAAACTAGCGATAACGCTGATGTTCTTGATGTGTTGTTGCATA
CTAGCGAGGAAGATCCAGAGGCAATCGACAGAATTCACAT--------

8) pCGP169

CAGTACACTCTTTGTGTTCATCATATCTCTTCACATTGCTCACAAGCTCG
ACCATGGCCGTCGGTAAGAACAAGAGGATTTCCAAAGGCA----------
-----AATACCACATTCTGATGATTCACTTGATATATGTGTACCTTTATG
TCATTTAATGGCACAACAATTCTGGGGACTTAGGTTCAAAGAAGC

9) pCGP171

CTGTAGGGTTACCGTTCATTGGAAATTTGCATCAATATGATACTTTAAAG
CCGCATATCTACTTCTGGAAACTTTCTAGGAAGTATGGAA----------
-----TACTTTCGGTTTTGAATTATGTATACATATATAAAACAAATGTGA
AATGTATACATATAATAAAATTGCTCTCATGATATACTTCTCTAT

10) pCGP173

TTCTGGAAATGTTTCTAGCTGGTACAGAGACATCTAGCAGCACAACAGAG
TGGGCACTAACTGAACTCCTTCGAAACCCAGAAACAATGG----------
-----ACAATTCTTACGCTGAATTTGTTGTTCGCCCTTTTATTTTCAGTT
TGATTGTATCCAAAGGATGTCGAATGAAATCATACTCTTTACCT

FIGURE 5A

CCGTTGCTGTCGAGAAAACAGAAAGAAGAGAAAA

35
```
ATG GAC TAC GTG AAT ATT TTG CTG GGA CTG TTT TTC ACT
Met Asp Tyr Val Asn Ile Leu Leu Gly Leu Phe Phe Thr

TGG TTC TTG GTG AAT GGA CTC ATG TCA CTT CGA AGA AGA
Trp Phe Leu Val Asn Gly Leu Met Ser Leu Arg Arg Arg
```

113
```
AAA ATC TCT AAG AAA CTT CCA CCA GGT CCA TTT CCT TTG
Lys Ile Ser Lys Lys Leu Pro Pro Gly Pro Phe Pro Leu

CCT ATC ATC GGA AAT CTT CAC TTA CTT GGT AAT CAT CCT
Pro Ile Ile Gly Asn Leu His Leu Leu Gly Asn His Pro
```

191
```
CAC AAA TCA CTT GCT CAA CTT GCA AAA ATT CAT GGT CCT
His Lys Ser Leu Ala Gln Leu Ala Lys Ile His Gly Pro

ATT ATG AAT CTC AAA TTA GGC CAA CTA AAC ACA GTG GTC
Ile Met Asn Leu Lys Leu Gly Gln Leu Asn Thr Val Val
```

269
```
ATT TCA TCA TCA GTC GTG GCA AGA GAA GTC TTG CAA AAA
Ile Ser Ser Ser Val Val Ala Arg Glu Val Leu Gln Lys

CAA GAC TTA ACA TTT TCC AAT AGG TTT GTC CCG GAC GTA
Gln Asp Leu Thr Phe Ser Asn Arg Phe Val Pro Asp Val
```

347
```
GTC CAT GTC CGA AAT CAC TCC GAT TTT TCT GTT GTT TGG
Val His Val Arg Asn His Ser Asp Phe Ser Val Val Trp

TTA CCA GTC AAT TCT CGA TGG AAA ACG CTT CGC AAA ATC
Leu Pro Val Asn Ser Arg Trp Lys Thr Leu Arg Lys Ile
```

FIGURE 5B

```
425
ATG AAC TCT AGC ATC TTT TCT GGT AAC AAG CTT GAT GGT
Met Asn Ser Ser Ile Phe Ser Gly Asn Lys Leu Asp Gly

AAT CAA CAT CTG AGG TCT AAA AAG GTC CAA GAG TTA ATT
Asn Gln His Leu Arg Ser Lys Lys Val Gln Glu Leu Ile

503
GAT TAT TGT CAA AAG TGT GCC AAG AAT GGC GAA GCA GTG
Asp Tyr Cys Gln Lys Cys Ala Lys Asn Gly Glu Ala Val

GAT ATA GGA AGA GCA ACT TTT GGA ACT ACT TTG AAT TTG
Asp Ile Gly Arg Ala Thr Phe Gly Thr Thr Leu Asn Leu

581
CTA TCC AAC ACC ATT TTC TCT AAA GAT TTG ACT AAT CCG
Leu Ser Asn Thr Ile Phe Ser Lys Asp Leu Thr Asn Pro

TTT TCT GAT TCT GCT AAA GAG TTT AAG GAA TTG GTT TGG
Phe Ser Asp Ser Ala Lys Glu Phe Lys Glu Leu Val Trp

659
AAC ATT ATG GTT GAG GCT GGA AAA CCC AAT TTG GTG GAC
Asn Ile Met Val Glu Ala Gly Lys Pro Asn Leu Val Asp

TAC TTT CCT TTC CTT GAG AAA ATT GAT CCG CAA GGT ATA
Tyr Phe Pro Phe Leu Glu Lys Ile Asp Pro Gln Gly Ile

737
AAG CGA CGC ATG ACT AAT AAT TTT ACT AAG TTT CTT GGC
Lys Arg Arg Met Thr Asn Asn Phe Thr Lys Phe Leu Gly

CTT ATC AGC GGT TTG ATT GAT GAC CGG TTA AAG GAA AGG
Leu Ile Ser Gly Leu Ile Asp Asp Arg Leu Lys Glu Arg
```

FIGURE 5C

```
815
AAT CTA AGG GAC AAT GCA AAT ATT GAT GTT TTA GAC GCC
Asn Leu Arg Asp Asn Ala Asn Ile Asp Val Leu Asp Ala

CTT CTC AAC ATT AGC CAA GAG AAC CCA GAA GAG ATT GAC
Leu Leu Asn Ile Ser Gln Glu Asn Pro Glu Glu Ile Asp 893                                         primer191
AGG AAT CAA ATC GAG CAG TTG TGT CTG GAC TTG TTT GCA
Arg Asn Gln Ile Glu Gln Leu Cys Leu Asp Leu Phe Ala primer190
GCA GGG ACT GAT ACT ACA TCG AAT ACC TTG GAG TGG GCA
Ala Gly Thr Asp Thr Thr Ser Asn Thr Leu Glu Trp Ala 971
ATG GCA GAA CTA CTT CAG AAT CCA CAC ACA TTG CAG AAA
Met Ala Glu Leu Leu Gln Asn Pro His Thr Leu Gln Lys GCA CAA GAA GAA CTT GCA CAA GTC ATT GGT AAA GGC AAA
Ala Gln Glu Glu Leu Ala Gln Val Ile Gly Lys Gly Lys 1049
CAA GTA GAA GAA GCA GAT GTT GGA CGA CTA CCT TAC TTG
Gln Val Glu Glu Ala Asp Val Gly Arg Leu Pro Tyr Leu CGA TGC ATA GTG AAA GAA ACC TTA CGA ATA CAC CCA GCG
Arg Cys Ile Val Lys Glu Thr Leu Arg Ile His Pro Ala 1127
GCT CCT CTC TTA ATT CCA CGT AAA GTG GAG GAA GAC GTT
Ala Pro Leu Leu Ile Pro Arg Lys Val Glu Glu Asp Val GAG TTG TCT ACC TAT ATT ATT CCA AAG GAT TCA CAA GTT
Glu Leu Ser Thr Tyr Ile Ile Pro Lys Asp Ser Gln Val
```

FIGURE 5D

```
1205
CTA GTG AAC GTA TGG GCA ATT GGA CGC AAC TCT GAT CTA
Leu Val Asn Val Trp Ala Ile Gly Arg Asn Ser Asp Leu

TGG GAA AAT CCT TTG GTC TTT AAG CCA GAA AGG TTT TGG
Trp Glu Asn Pro Leu Val Phe Lys Pro Glu Arg Phe Trp

1283
GAG TCA GAA ATA GAT ATC CGA GGT CGA GAT TTT GAA CTC
Glu Ser Glu Ile Asp Ile Arg Gly Arg Asp Phe Glu Leu

ATT CCA TTT GGT GCT GGT CGA AGA ATT TGC CCT GGA TTG
Ile Pro Phe Gly Ala Gly Arg Arg Ile Cys Pro Gly Leu

1361
CCT TTG GCT ATG AGG ATG ATT CCA GTA GCA CTA GGT TCA
Pro Leu Ala Met Arg Met Ile Pro Val Ala Leu Gly Ser

TTG CTA AAC TCA TTT AAT TGG AAA CTA TAT GGT GGA ATT
Leu Leu Asn Ser Phe Asn Trp Lys Leu Tyr Gly Gly Ile

1439
GCA CCT AAA GAT TTG GAC ATG CAG GAA AAG TTT GGC ATT
Ala Pro Lys Asp Leu Asp Met Gln Glu Lys Phe Gly Ile

ACC TTG GCG AAA GCC CAA CCT CTG CTA GCT ATC CCA ACT
Thr Leu Ala Lys Ala Gln Pro Leu Leu Ala Ile Pro Thr

1517
CCC CTG TAG CTATAGGGATAAATTAAGTTGAGGTTTTAAGTTACTAGT
Pro Leu

AGATTCTATTGCAGCTATAGGATTTCTTTCACCATCACGTATGCTTTACCG

TTGGATGATGGAAAGAAATATCTATAGCTTTGGGTTTGTTTAGTTTGCACA

TAAAAATTGAATGAATGGAATACCATGGAGTTATAAGAAATAATAAGACTA

TGATTCTTACCCTACTTGAACAATGACATGGCTATTTCAC
```

Sequence of pCGP635 insert

```
                                                                                          TT
Leu Glu Trp Ala Met Ala Glu Ile Leu Arg His Pro Arg Val Cys Arg Lys Met Gln Asn
TTG GAG TGG GCA ATG GCC GAA ATC TTG AGG CAT CCC AGA GTT TGT AGA AAA ATG CAA AAT
3

Glu Ala Met Glu Ile Ala Asn Gly Lys Pro His Ile Thr Glu Ser Asp Leu Asp Lys Met
GAG GCG ATG GAG ATT GCT AAT GGC AAA CCA CAC ATC ACA GAA AGT GAT TTA GAT AAA ATG
63

His Tyr Leu Lys Ala Val Ile Lys Glu Thr Leu Arg Leu Leu Pro Pro Ile Pro Leu Leu
CAC TAC TTG AAA GCA GTG ATC AAA GAG ACA CTT CGG CTA CAT CCG CCA ATA CCA TTA CTC
123

Ser Pro Arg Glu Ser Thr Glu Asp Val Lys Ile Met Glu Ser Asp Ile Glu Val Lys Lys
TCC CCT CGT GAA TCA ACT GAA GAT GTT AAG ATA ATG GAA TCT GAC ATA GAA GTC AAA AAA
183

Leu Trp Ser Leu Ser Met Leu Gly Gln Ser Gln Thr Gln Gln Ser Val Ser Gly Met Asn Gln
CTA TGG TCT TTA TCA ATG CTT GGG CAA TCG CAG ACC CAG CAG AGT GGG ATG AAC CAA
243

Glu Phe Arg Pro Glu Arg Phe Met Asn Ser Ser Val Asp Phe Lys Gly His Leu Phe Gln
GAG TTT CGA CCG GAG AGA TTC ATG AAT TCT TCT GTG GAT TTC AAA GGT CAT CTC TTT CAA
303

Leu Leu Pro Phe Gly Ala Gly Arg Arg
TTA CTC CCC TTC GGA GCC GGC CGC AGA T
363
```

FIGURE 8

Sequence of pCGP772 insert

```
    Ala Glu Leu Leu Arg Asn Pro Glu Lys Met
TG  GCG GAA CTA CTG CGC AAC CCC GAG AAA ATG
         10          20          30

Ala Lys Ala Gln Asp Glu Ile Asp Arg Ile Val
GCA AAA GCA CAA GAC GAA ATA GAC CGA ATA GTA
        40          50          60

Gly Asp Lys Asn Lys Ser Phe Gln Glu Thr Asp
GGC GAC AAG AAC AAA TCG TTC CAA GAG ACA GAC
    70          80          90

Ile Ser Lys Leu Pro Tyr Ile Gln Ala Val Val
ATC TCA AAG TTA CCG TAC ATT CAA GCG GTT GTT
100         110         120         130

Lys Glu Thr Leu Arg Leu His Pro Pro Gly Pro
AAA GAA ACA TTA AGG CTA CAC CCG CCT GGA CCG
        140         150         160

Phe Leu Ile Pro His Lys Ala Glu Lys Asp Val
TTC CTA ATA CCC CAC AAA GCC GAA AAG GAC GTA
        170         180         190

Asn Leu Ser Arg Phe Phe Ile Pro Glu Asp Ala
AAC TTA AGC CGG TTT TTC ATC CCC GAG GAC GCC
        200         210         220

Gln Val Trp Val Asn Val Trp Ala Ile Gly Arg
CAA GTG TGG GTC AAT GTA TGG GCC ATT GGT CGT
230         240         250         260
```

FIGURE 9A

```
Asp Pro Ser Val Trp Arg Val Pro Leu Thr Leu
GAT CCA AGC GTG TGG CGG GTC CCA CTT ACA TTG
        270         280         290

Cys Pro Glu Arg Phe Leu Glu Asn Asp Ile Asp
TGT CCT GAA CGG TTT TTG GAA AAC GAC ATC GAT
        300         310         320

Phe Lys Gly Thr Asp Phe Glu Leu Ile Pro Phe
TTC AAA GGT ACA GAT TTC GAG CTG ATT CCC TTT
    330         340         350         360

Gly Ala Gly Arg Ile
GGC GCC GGC CGC ATC
        370
```

FIGURE 9B

Sequence of pCGP773 insert

```
    Met Ala Glu Leu Leu Arg Asn Pro Glu Lys Leu
A   ATG GCA GAG CTG CTC CGT AAC CCA GAA AAA CTG
             10              20              30

Lys Lys Ala Gln Val Glu Leu Gln Glu Ile Ile
    AAG AAA GCA CAA GTA GAG CTT CAA GAA ATC ATC
             40              50              60

Gly Arg Gly Asn Thr Leu Glu Glu Ser Asp Ile
    GGC AGA GGA AAC ACA TTA GAG GAA TCT GAC ATC
         70              80              90              100

Ser Arg Leu Pro Tyr Leu Gln Ala Ile Ile Lys
    AGT CGA TTG CCA TAT TTA CAG GCT ATC ATT AAG
                 110             120             130

Glu Thr Phe Arg Leu His Pro Gly Leu Pro Leu
    GAA ACA TTT CGG CTA CAC CCA GGA CTG CCA TTA
                 140             150             160

Leu Leu Pro Arg Lys Val Gly Ser Asp Val Gln
    TTG CTA CCT AGG AAA GTT GGT TCA GAC GTT CAG
                 170             180             190

Leu Phe Gly Phe Thr Val Pro Lys Asn Ala Gln
    CTC TTT GGG TTT ACA GTA CCC AAA AAT GCA CAA
    200             210             220             230

Val Ile Ile Asn Ala Trp Ala Ile Gly Arg Asp
    GTC ATA ATC AAC GCC TGG GCA ATT GGG AGA GAC
                 240             250             260
```

FIGURE 10 A

```
Pro Asp Cys Trp Gln Lys Pro Asn Ser Phe Glu
CCA GAT TGT TGG CAG AAA CCC AAC TCA TTT GAG
    270         280         290

Pro Glu Arg Phe Leu Gly Ser Gln Ile Asp Val
CCA GAA AGG TTC CTT GGG TCA CAA ATT GAT GTG
 300         310         320         330

Lys Gly Arg Asp Phe Glu Leu Ile Pro Phe Gly
AAG GGT CGT GAT TTT GAG CTA ATT CCC TTT GGC
        340         350         360

Ala Gly Arg Ser Ile Cys Ala
GCC GGC CGC AGC ATC TGT GCC G
    370         380
```

FIGURE 10 B

Partial sequence of pCGP854 insert

PRIMER 190 ---->

```
TTG GAG TGG GCA ATG GCA GAA CTT CTA CGC AAC CCG CAC ACC ATG
Leu Glu Trp Ala Met Ala Glu Leu Leu Arg Asn Pro His Thr Met
 1

GCC AAA GCA AAA GAG GAG CTT AAA GAC GTT ATC GGC AAA GAA AAA
Ala Lys Ala Lys Glu Glu Leu Lys Asp Val Ile Gly Lys Glu Lys
46

CTT GTA GAT GAA GCT GAC ATT TTC GAG ACT
Leu Val Asp Glu Ala Asp Ile Phe Glu Thr
91
```

FIGURE 11

GENETIC SEQUENCES ENCODING FLAVONOID PATHWAY ENZYMES AND USES THEREFOR

The present invention relates generally to genetic sequences encoding flavonoid pathway metabolising enzymes and more particularly to flavonoid 3'-hydroxylase or fragments or derivatives thereof and their use in the manipulation of pigmentation in plants and other organisms.

The flower industry strives to develop new and different varieties of flowering plants. An effective way to create such novel varieties is through the manipulation of flower colour. Classical breeding techniques have been used with some success to produce a wide range of colours for most of the commercial varieties of flowers. This approach has been limited, however, by the constraints of a particular species' gene pool and for this reason it is rare for a single species to have a full spectrum of coloured varieties. In addition, traditional breeding techniques lack precision. The aesthetic appeal of the flower is a combination of many factors such as form, scent and colour; modification of one character through hybridization can often be at the expense of an equally valuable feature. The ability to engineer precise colour changes in cutflower and ornamental species would offer significant commercial opportunities in an industry which has rapid product turnover and where novelty is an important market characteristic.

Flower colour is predominantly due to two types of pigment: flavonoids and carotenoids. Flavonoids contribute to a range of colours from yellow to red to blue. Carotenoids impart an orange or yellow tinge and are commonly the major pigment in yellow or orange flowers. The flavonoid molecules which make the major contribution to flower colour are the anthocyanins which are glycosylated derivatives of cyanidin, delphinidin, petunidin, peonidin, malvidin and pelargonidin, and are localised in the vacuole. The different anthocyanins can produce marked differences in colour. Flower colour is also influenced by co-pigmentation with colourless flavonoids, metal complexation, glycosylation, acylation and vacuolar pH (Forkmann, 1991).

Figure 1B:
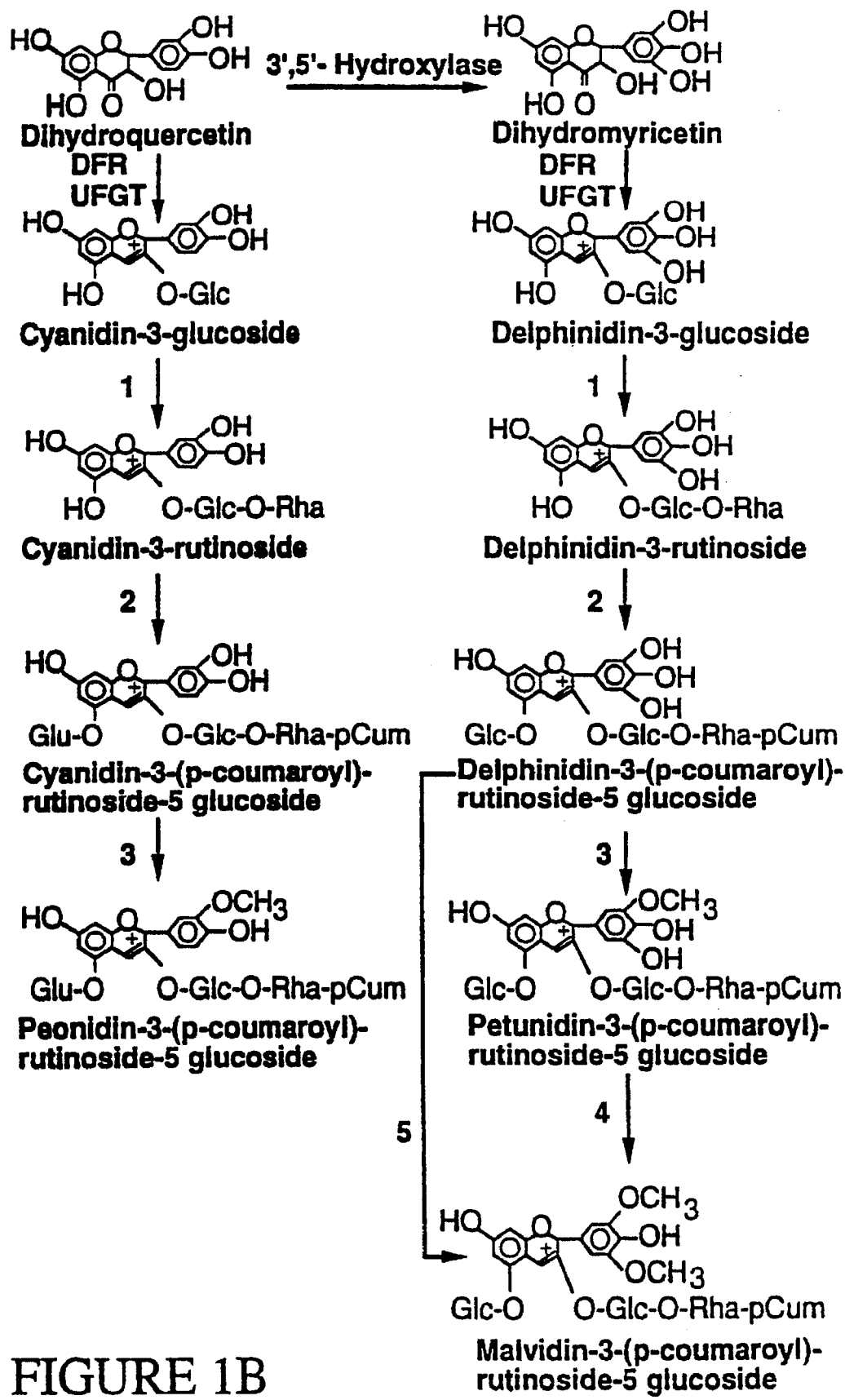

The biosynthetic pathway for the flavonoid pigments (hereinafter referred to as the "flavonoid pathway") is well established and is shown in FIG. 1 (Ebel and Hahlbrock, 1988; Hahlbrock and Grisebach, 1979; Wiering and De Vlaming, 1984; Schram et al., 1984; Stafford, 1990). The first committed step in the pathway involves the condensation of three molecules of malonyl-CoA with one molecule of p-coumaroyl-CoA. This reaction is catalysed by the enzyme chalcone synthase (CHS). The product of this reaction, 2',4,4',6', tetrahydroxy-chalcone, is normally rapidly isomerized to produce naringenin by the enzyme chalcone flavanone isomerase (CHI). Naringenin is subsequently hydroxylated at the 3 position of the central ring by flavanone 3-hydroxylase (F3H) to produce dihydrokaempferol (DHK).

The pattern of hydroxylation of the B-ring of DHK plays a key role in determining petal colour. The B-ring can be hydroxylated at either the 3', or both the 3' and 5' positions, to produce dihydroquercetin (DHQ) and dihydromyricetin (DHM), respectively. Two key enzymes involved in this pathway are flavonoid 3'-hydroxylase and flavonoid 3',5'-hydroxylase, both of the cytochrome P450 class. Cytochrome P450 enzymes are widespread in nature and genes have been isolated and sequenced from vertebrates, insects, yeasts, fungi, bacteria and plants.

Flavonoid 3'-hydroxylase acts on DHK to produce DHQ and on naringenin to produce eriodictyol. Reduction and glycosylation of DHQ produces the cyanidin-glycoside and peonidin-glycoside pigments which, in many plant species (for example rose, carnation and chrysanthemum), contribute to red and pink flower colour. The synthesis of these anthocyanins can also result in other flower colours. For example, blue cornflowers contain cyanin. The ability to control flavonoid 3'-hydroxylase activity, or other enzymes involved in the flavonoid pathway, in flowering plants would provide a means to manipulate petal colour. Different coloured versions of a single cultivar could thereby be generated and in some instances a single species would be able to produce a broader spectrum of colours.

In accordance with the present invention, the genetic sequences encoding flavonoid 3'-hydroxylase have been identified and cloned. These recombinant sequences permit the modulation of hydroxylation of substrates such as DHK and naringenin, leading to a modification of anthocyanin composition, thereby providing a means to manipulate petal colour. The presence of the flavonoid 3'-hydroxylase would allow the diversion of the metabolic pathway from DHK to anthocyanin derivatives of anthocyanidins such as cyanidin and peonidin, thereby providing a means to manipulate petal colour by modulation of the level of 3'-hydroxylation. Accordingly, the present invention relates to the altering of flavonoid 3'-hydroxylase activity in plants, which encompasses elevating or reducing levels of existing flavonoid 3'-hydroxylase activity by introducing the sequences of the present invention. Reduction in levels of flavonoid 3'-hydroxylase activity may also be referred to as down-regulation. Moreover, the present invention extends beyond flowers to fruit and vegetable plants and to leaves of, for example, ornamental plants.

Accordingly, one aspect of the present invention provides a nucleic acid isolate comprising a sequence of nucleotides encoding, or complementary to a sequence encoding, flavonoid 3'-hydroxylase enzyme (hereinafter referred to as 3'-hydroxylase) or a functional derivative of the enzyme.

By the term "nucleic acid isolate" is meant a genetic sequence in a non-naturally-occurring condition. Generally, this means isolated away from its natural state or synthesized or derived in a non-naturally-occurring environment. More specifically, it includes nucleic acid molecules formed or maintained in vitro, including genomic DNA fragments, recombinant or synthetic molecules and nucleic acids in combination with heterologous nucleic acids. It also extends to the genomic DNA or cDNA or part thereof encoding 3'-hydroxylase or part thereof in reverse orientation relative to its or another promoter. It further extends to naturally-occurring sequences following at least a partial purification relative to other nucleic acid sequences.

The term "genetic sequences" is used herein in its most general sense and encompasses any contiguous series of nucleotide bases specifying directly, or via a complementary series of bases, a sequence of amino acids in a 3'-hydroxylase. Such a sequence of amino acids may constitute a full-length 3'-hydroxylase or an active truncated form thereof or may correspond to a particular region such as an N-terminal, C-terminal or internal portion of the enzyme. The nucleic acid sequences contemplated herein also encompass oligonucleotides useful as genetic probes or as "antisense" molecules capable of regulating expression of the corresponding gene in a plant. An "antisense molecule" as used herein may also encompass a gene construct comprising the structural genomic or cDNA gene or part thereof in reverse orientation relative to its or another promoter.

In one embodiment the nucleic acid sequence encoding 3'-hydroxylase or various functional derivatives thereof are used to reduce the activity of an endogenous 3'-hydroxylase, or alternatively the nucleic acid sequence encoding this enzyme or various derivatives or parts thereof are used in the antisense orientation to reduce activity of the 3'-hydroxylase. Although not wishing to limit the present invention to any one theory, it is possible that an antisense 3'-hydroxylase transcript or fragment or part thereof (for example, an oligonucleotide molecule) would form a duplex with all or part of the naturally occurring mRNA specified for the enzyme thus preventing accumulation of or translation from the mRNA into active enzyme. In a further alternative, ribozymes could be used to inactivate target nucleic acid sequences.

Reference herein to the altering of flavonoid 3'-hydroxylase activity relates to an elevation or reduction in activity of up to 30% or more preferably of 30–50%, or even more preferably 50–75% or still more preferably 75% or greater above or below the normal endogenous or existing levels of activity. The level of activity can be readily assayed using a modified version of the method described by Stotz and Forkmann (1982) (see Example 1).

The nucleic acids of the present invention may be a ribonucleic acid or deoxyribonucleic acids, single or double stranded and linear or covalently closed circular molecules. Preferably, the nucleic acid molecule is cDNA. The present invention also extends to other nucleic acid molecules which hybridize under low, preferably under medium and most preferably under high stringency conditions with the nucleic acid molecules of the present invention and in particular to the sequence of nucleotides set forth in FIG. 5 or a part or region thereof. In its most preferred embodiment, the present invention extends to a nucleic acid molecule having a nucleotide sequence set forth in FIG. 5 or to a molecule having at least 40%, more preferably at least 45%, even more preferably at least 55%, still more preferably at least 65–70%, and yet even more preferably greater than 85% similarity at the level of nucleotide or amino acid sequence to at least one or more regions of the sequence set forth in FIG. 5 and wherein the nucleic acid encodes or is complementary to a sequence which encodes an enzyme having 3'-hydroxylase activity. It should be noted, however, that nucleotide or amino acid sequences may have similarities below the above given percentages and yet still encode 3'-hydroxylase activity and such molecules may still be considered in the scope of the present invention where they have regions of sequence conservation. The present invention further extends to nucleic acid molecules in the form of oligonucleotide primers or probes capable of hybridizing to a portion of the nucleic acid molecules contemplated above, and in particular those set forth in FIG. 5, under low, preferably under medium and most preferably under high stringency conditions. Preferably the portion corresponds to the 5' or the 3' end of the gene. For convenience the 5' end is considered herein to define a region substantially between the start codon of the structural genetic sequence to a centre portion of the gene, and the 3' end is considered herein to define a region substantially between the centre portion of the gene and the terminating codon of the structural genetic sequence. It is clear, therefore, that oligonucleotides or probes may hybridize to the 5' end or the 3' end or to a region common to both the 5' and the 3' ends. The present invention extends to all such probes. Preferred oligonucleotides are set forth in Example 1.

The nucleic acid or its complementary form may encode the full-length enzyme or a part or derivative thereof. By "derivative" is meant any single or multiple amino acid substitutions, deletions, and/or additions relative to the naturally-occurring enzyme and which retains 3'-hydroxylase activity. In this regard, the nucleic acid includes the naturally-occurring nucleotide sequence encoding 3'-hydroxylase or may contain single or multiple nucleotide substitutions, deletions and/or additions to said naturally-occurring sequence. The nucleic acid of the present invention or its complementary form may also encode a "part" of the 3'-hydroxylase, whether active or inactive, and such a nucleic acid molecule may be useful as an oligonucleotide probe, primer for polymerase chain reactions or in various mutagenic techniques, or for the generation of antisense molecules.

Amino acid insertional derivatives of the 3'-hydroxylase of the present invention include amino and/or carboxyl terminal fusions as well as intra-sequence insertions of single or multiple amino acids. Insertional amino acid sequence variants are those in which one or more amino acid residues are introduced into a predetermined site in the protein although random insertion is also possible with suitable screening of the resulting product. Deletional variants are characterised by the removal of one or more amino acids from the sequence. Substitutional amino acid variants are those in which at least one residue in the sequence has been removed and a different residue inserted in its place. Typical substitutions are those made in accordance with Table 1 overleaf.

Where the 3'-hydroxylase is derivatised by amino acid substitution, the amino acids are generally replaced by other amino acids having like properties, such as hydrophobicity, hydrophilicity, electronegativity, bulky side chains and the like. Amino acid substitutions are typically of single residues. Amino acid insertions will usually be in the order of about 1–10 amino acid residues and deletions will range from about 1–20 residues. Preferably, deletions or insertions are made in adjacent pairs, i.e. a deletion of two residues or insertion of two residues.

The amino acid variants referred to above may readily be made using peptide synthetic techniques well known in the art, such as solid phase peptide synthesis (Merrifield, 1964) and the like, or by recombinant DNA manipulations. Techniques for making substitution mutations at predetermined sites in DNA having known or partially known sequence are well known and include, for example, M13 mutagenesis. The manipulation of DNA sequence to produce variant proteins which manifest as substitutional, insertional or deletional variants are conveniently described, for example, in Sambrook et al. (1989).

TABLE 1

Suitable residues for amino acid substitutions

| Original Residue | Exemplary Substitutions |
| --- | --- |
| Ala | Ser |
| Arg | Lys |
| Asn | Gln; His |
| Asp | Glu |
| Cys | Ser |
| Gln | Asn |
| Glu | Asp |
| Gly | Pro |
| His | Asn; Gln |
| Ile | Leu; Val |
| Leu | Ile; Val |
| Lys | Arg; Gln; Glu |
| Met | Leu; Ile |
| Phe | Met; Leu; Lyr |
| Ser | Thr |
| Thr | Ser |

TABLE 1-continued

Suitable residues for amino acid substitutions

| Original Residue | Exemplary Substitutions |
|---|---|
| Trp | Tyr |
| Tyr | Trp; Phe |
| Val | Ile; Leu |

Other examples of recombinant or synthetic mutants and derivatives of the 3'-hydroxylase of the present invention include single or multiple substitutions, deletions and/or additions of any molecule associated with the enzyme such as carbohydrates, lipids and/or proteins or polypeptides.

The terms "analogues" and "derivatives" also extend to any functional chemical equivalent of the 3'-hydroxylase and also to any amino acid derivative described above. For convenience, reference to "3'-hydroxylase" herein includes reference to any mutants, derivatives, analogues, homologues or fragments thereof.

The present invention is exemplified using nucleic acid sequences derived from petunia since this represents the most convenient and preferred source of material to date. However, one skilled in the art will immediately appreciate that similar sequences can be isolated from any number of sources such as other plants or certain microorganisms. Examples of other plants include, but are not limited to, carnation, chrysanthemum, rose, maize, snapdragon, tobacco, cornflower, pelargonium and morning glory. All such nucleic acid sequences encoding directly or indirectly a flavonoid pathway enzyme and in particular 3'-hydroxylase, regardless of their source, are encompassed by the present invention.

The nucleic acid molecules contemplated herein may exist in either orientation alone or in combination with a vector molecule, for example an expression-vector. The term vector molecule is used in its broadest sense to include any intermediate vehicle for the nucleic acid molecule, capable of facilitating transfer of the nucleic acid into the plant cell and/or facilitating integration into the plant genome. An intermediate vehicle may, for example, be adapted for use in electroporation, microprojectile bombardment, Agrobacterium-mediated transfer or insertion via DNA or RNA viruses. The intermediate vehicle and/or the nucleic acid molecule contained therein may or may not need to be stably integrated into the plant genome. Such vector molecules may also replicate and/or express in prokaryotic cells. Preferably, the vector molecules or parts thereof are capable of integration into the plant genome. The nucleic acid molecule may additionally contain a promoter sequence capable of directing expression of the nucleic acid molecule in a plant cell. The nucleic acid molecule and promoter may also be introduced into the cell by any number of means such as those described above.

In accordance with the present invention, a nucleic acid sequence encoding 3'-hydroxylase or a derivative or part thereof may be introduced into and expressed in a plant in either orientation thereby providing a means either to convert DHK and/or other suitable substrates, if synthesised in the plant cell, ultimately into anthocyanin derivatives of anthocyanidins such as cyanidin and/or peonidin, or alternatively to inhibit such conversion of metabolites by reducing or eliminating endogenous or existing 3'-hydroxylase activity. The production of anthocyanins contributes to the production of a red or blue flower colour. Expression of the nucleic acid sequence in either orientation in the plant may be constitutive, inducible or developmental, and may also be tissue-specific. The word expression is used in its broadest sense to include production of RNA or of both RNA and protein. It also extends to partial expression of a nucleic acid molecule.

According to this aspect of the present invention there is provided a method for producing a transgenic plant capable of synthesizing 3'-hydroxylase or active mutants or derivatives thereof, said method comprising stably transforming a cell of a suitable plant with a nucleic acid molecule which comprises a sequence of nucleotides encoding said 3'-hydroxylase, under conditions permitting the eventual expression of said nucleic acid molecule, regenerating a transgenic plant from the cell and growing said transgenic plant for a time and under conditions sufficient to permit the expression of the nucleic acid. The transgenic plant may thereby produce elevated levels of 3'-hydroxylase activity relative to the amount expressed in a comparable non-transgenic plant.

Another aspect of the present invention contemplates a method for producing a transgenic plant with reduced endogenous or existing 3'-hydroxylase activity, said method comprising stably transforming a cell of a suitable plant with a nucleic acid molecule which comprises a sequence of nucleotides encoding or complementary to a sequence encoding 3'-hydroxylase, regenerating a transgenic plant from the cell and where necessary growing said transgenic plant under conditions sufficient to permit the expression of the nucleic acid.

Yet another aspect of the present invention contemplates a method for producing a genetically modified plant with reduced endogenous or existing 3'-hydroxylase activity, said method comprising altering the 3'-hydroxylase gene through modification of the endogenous sequences via homologous recombination from an appropriately altered 3'-hydroxylase gene or derivative or part thereof introduced into the plant cell, and regenerating the genetically modified plant from the cell.

In a preferred embodiment, the present invention contemplates a method for producing a transgenic flowering plant exhibiting altered inflorescence properties, said method comprising stably transforming a cell of a suitable plant with a nucleic acid sequence of the present invention, regenerating a transgenic plant from the cell and growing said transgenic plant for a time and under conditions sufficient to permit the expression of the nucleic acid sequence into the 3'-hydroxylase enzyme. Alternatively, said method may comprise stably transforming a cell of a suitable plant with a nucleic acid sequence of the present invention or its complementary sequence, regenerating a transgenic plant from the cell and growing said transgenic plant for a time and under conditions sufficient to alter the level of activity of the endogenous or existing 3'-hydroxylase. Preferably the altered level would be less than the endogenous or existing level of 3'-hydroxylase activity in a comparable non-transgenic plant. Without wishing to limit the present invention, one theory of mode of action is that reduction of the endogenous 3'-hydroxylase activity requires the expression of the introduced nucleic acid sequence or its complementary sequence. However, expression of the introduced genetic sequence or its complement may not be required to achieve the desired effect: namely, a flowering plant exhibiting altered inflorescence properties.

In a related embodiment, the present invention contemplates a method for producing a flowering plant exhibiting altered inflorescence properties, said method comprising alteration of the 3'-hydroxylase gene through modification of the endogenous sequences via homologous recombination from an appropriately altered 3'-hydroxylase gene or derivative or part thereof introduced into the plant cell, and regenerating the genetically modified plant from the cell.

The nucleic acid molecule of the present invention may or may not be developmentally regulated. Preferably, the altered inflorescence includes the production of red flowers or other colour shades depending on the physiological conditions of the recipient plant. By "recipient plant" is meant a plant capable of producing a substrate for the 3'-hydroxylase enzyme, or producing the 3'-hydroxylase enzyme itself, and possessing the appropriate physiological properties and genotype required for the development of the colour desired. This may include but is not limited to petunia, carnation, chrysanthemum, rose, snapdragon, tobacco, cornflower, pelargonium, lisianthus and morning glory.

Accordingly, the present invention extends to a method for producing a transgenic plant capable of expressing a recombinant gene encoding 3'-hydroxylase or part thereof or which carries a nucleic acid sequence which is substantially complementary to all or a part of a mRNA molecule optionally transcribable where required to effect regulation of a 3'-hydroxylase, said method comprising stably transforming a cell of a suitable plant with the nucleic acid isolate comprising a sequence of nucleotides encoding, or complementary to a sequence encoding, 3'-hydroxylase or a derivative or part thereof, where necessary under conditions permitting the eventual expression of said nucleic acid isolate, and regenerating a transgenic plant from the cell.

One skilled in the art will immediately recognise the variations applicable to the methods of the present invention, such as increasing or decreasing the expression of the enzyme naturally present in a target plant leading to differing shades of colours such as different shades of red.

The present invention, therefore, extends to all transgenic plants containing all or part of the nucleic acid sequence of the present invention and/or any homologues or related forms thereof or antisense forms of any of these and in particular those transgenic plants which exhibit altered inflorescence properties. The transgenic plants may contain an introduced nucleic acid molecule comprising a nucleotide sequence encoding or complementary to a sequence encoding 3'-hydroxylase. Generally the nucleic acid would be stably introduced into the plant genome, although the present invention also extends to the introduction of the 3'-hydroxylase nucleotide sequence within an autonomously-replicating nucleic acid sequence such as a DNA or RNA virus capable of replicating within the plant cell. The invention also extends to seeds from such transgenic plants. Such seeds, especially if coloured, will be useful as proprietary tags for plants.

A further aspect of the present invention is directed to recombinant forms of 3'-hydroxylase. The recombinant forms of the enzymes will provide a source of material for research to develop, for example, more active enzymes and may be useful in developing in vitro systems for production of coloured compounds.

Still a further aspect of the present invention contemplates the use of the genetic sequences described herein in the manufacture of a genetic construct capable of expressing a 3'-hydroxylase enzyme or down-regulating an endogenous 3'-hydroxylase in a plant.

The present invention is further described by reference to the following non-limiting Figures and Example.

In the Figures:

FIGS. 1A and B are is a schematic representation of the biosynthesis pathway for the flavonoid pigments. Enzymes involved in the first part of the pathway have been indicated as follows: PAL=Phenylalanine ammonia-lyase; C4H= Cinnamate 4-hydroxylase; 4CL=4-coumarate: CoA ligase; CHS=Chalcone synthase; CHI=Chalcone flavanone isomerase; F3H=Flavanone 3-hydroxylase; DFR= Dihydroflavonol-4-reductase; UFGT=UDP-glucose: flavonoid-3-O-glucosyl-transferase. The later steps correspond to conversions that occur in P. hybrida flowers and include: 1=addition of a rhamnose sugar to the glucosyl residue of cyanidin-3-glucoside and delphinidin-3-glucoside; 2=acylation and 5-O-glucosylation; 3=3' methylation; 4=5' methylation; 5=3',5' methylation.

Figure 2A:
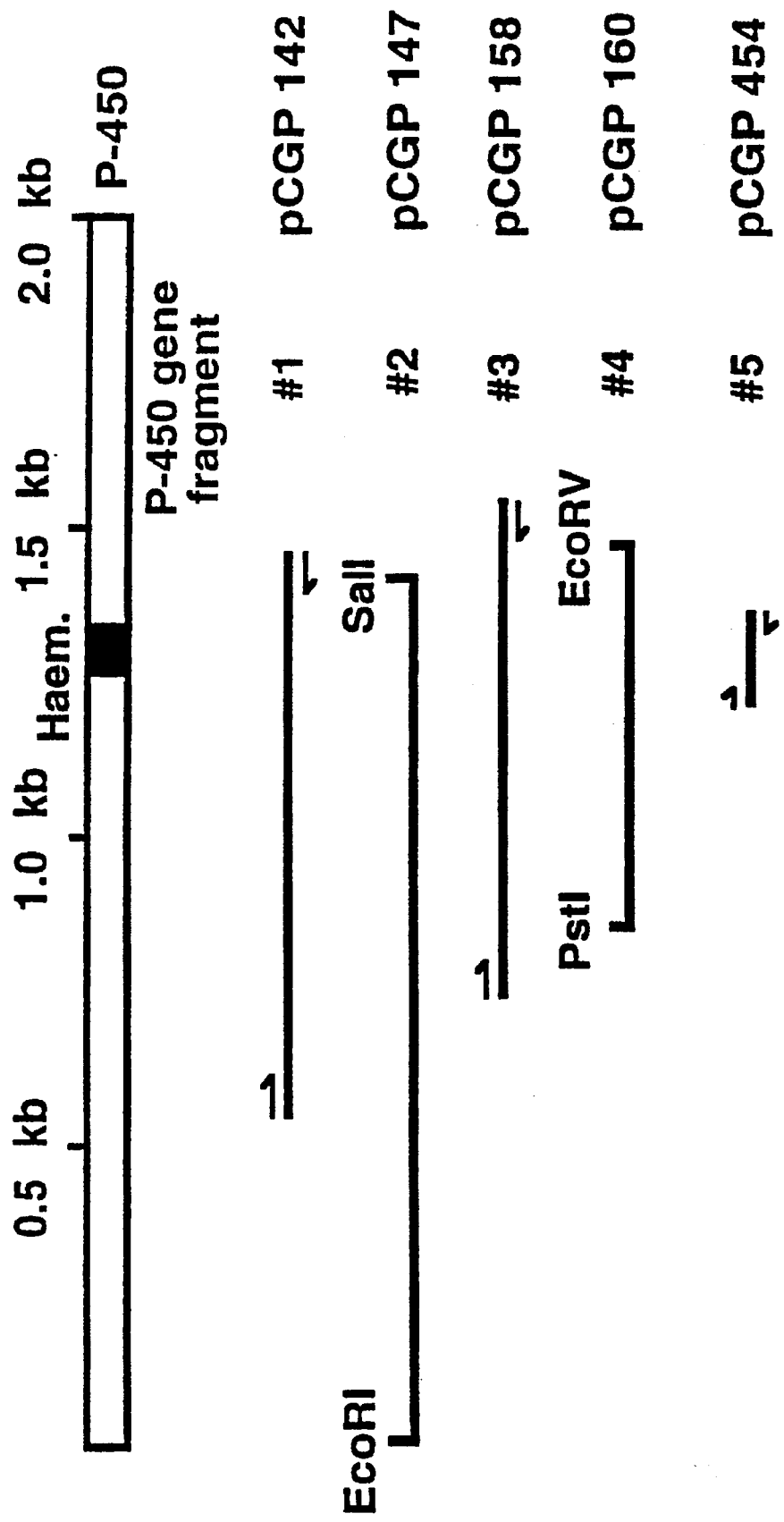

FIG. 2(A) is a schematic representation of DNA fragments used to probe cDNA library #1 to identify cytochrome P450 homologues. P450: generalized cytochrome P450 cDNA clone with the haem-binding domain (Haem) indicated by the shaded box; pCGP142: a 980 bp fragment was obtained by PCR with oligos 1 and 2 using pCGP142 DNA as template; pCGP147: a 1.3 kb fragment was isolated from a SalI-EcoRI digest of pCGP147; pCGP158: a 900 bp fragment was obtained by PCR with oligos 3 and 4 using pCGP158 DNA as template; pCGP160: a 600 bp fragment was isolated from a PstI-EcoRV digest of pCGP160; pCGP454: fragment was obtained by PCR with oligos 3 and 5 using pCGP454 DNA as template. All purified fragments were labelled with $^{32}$P-dCTP as described in Example 1.

FIGS. 2(B) to (H) show partial nucleotide sequences and the corresponding predicted amino acid translation products for the cDNA inserts from (i) pCGP142 (SEQ ID NOS:27, 28), (ii) pCGP147 (SEQ ID NOS:29,30), (iii) pCGP158 (SEQ ID NOS:31,32), (iv) pCGP160 (SEQ ID NOS:33,34) and (v) pCGP454 (SEQ ID NOS:35,36). The regions used to probe cDNA library #1 to isolate related clones have been delineated by arrowheads.

FIGS. 3(A) to (D) is the nucleotide sequence (SEQ ID NO:37) and predicted amino acid sequence (SEQ ID NO:38) for the cDNA insert from pCGP602. Two probes that included the sequences between the internal HincII-EcoRV and EcoRV-HindIII sites were used to identify related sequences in a group of cytochrome P450 homologues.

FIGS. 4(A) and 4(B) show partial nucleotide sequence for the cDNA inserts from: 4(A): 1) pCGP161 (SEQ ID NO:39); 2) pCGP162 (SEQ ID NO:40); 3) pCGP163 (SEQ ID NO:41); 4) pCGP165 (SEQ ID NO:42); 5) pCGP166 (SEQ ID NO:43); 6) pCGP167 (SEQ ID NO:44), and 4(B): 7 pCGP168 (SEQ ID NO:45); 8) pCGP169 (SEQ ID NO:46); 9) pCGP171 (SEQ ID NO:47) and 10) pCGP173 (SEQ ID NO:48). A mixed probe that included the cDNA inserts of all these clones was used to screen cDNA library #2 for related sequences.

FIGS. 5A–D are the nucleotide sequence (SEQ ID NO:49) and predicted amino acid sequence (SEQ ID NO:50) for the cDNA insert from pCGP619.

Figure 6:
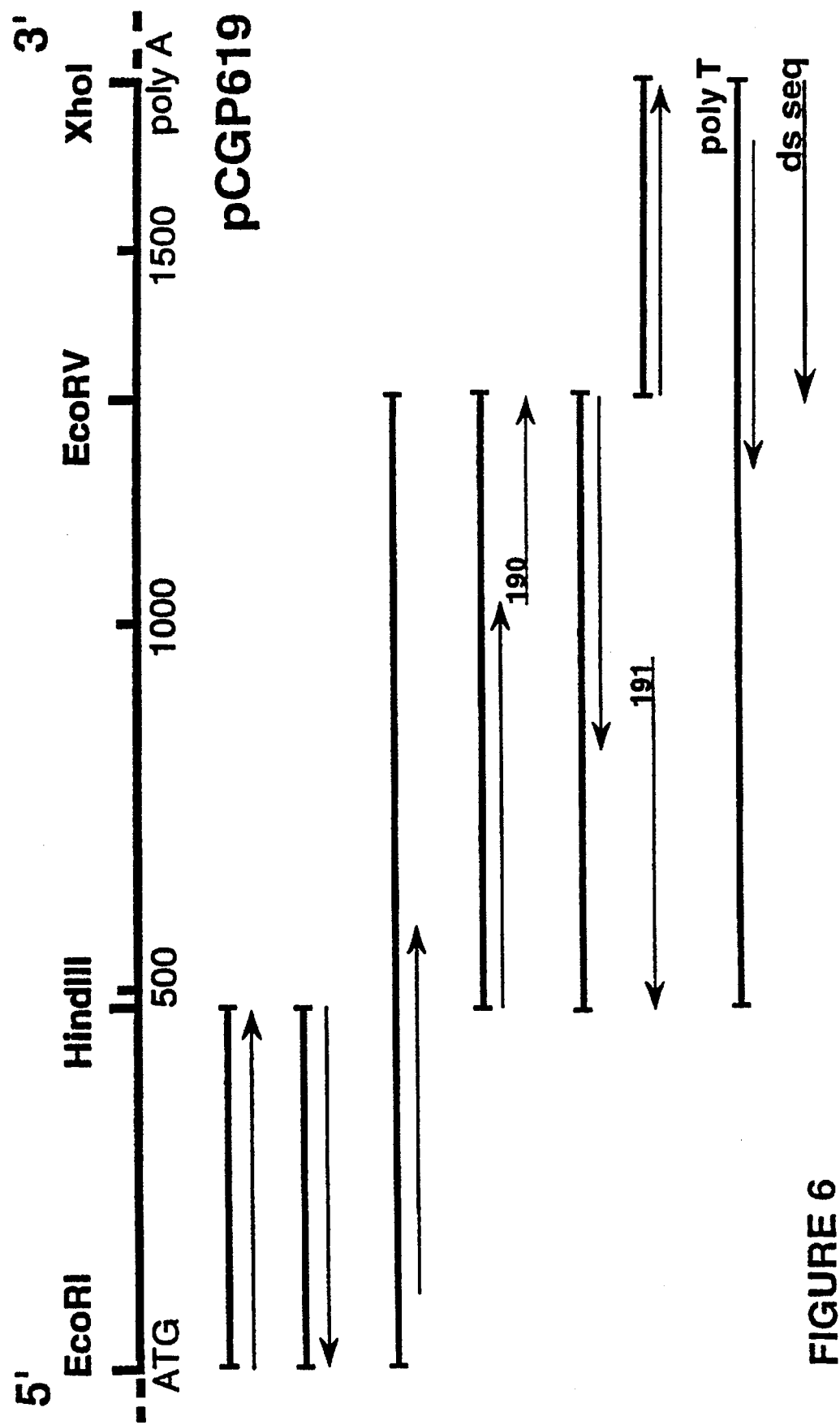

FIG. 6 shows a diagrammatic representation of a restriction enzyme map of pCGP619. Partial lengths of the cDNA insert are indicated by the bolder lines with solid ends (as opposed to arrows). These were subcloned into M13-mp18 and mp19 and sequenced using oligonucleotide primer sequences, as indicated, to obtain overlapping sequence information. The extent and direction of sequence information obtained from each subcloned piece is shown by lines with arrowheads. Primer –40 was used unless otherwise specified. 190=primer sequence 190; 191=primer sequence 191; poly T=poly T oligonucleotide was used as primer; ds seq=sequence was read with double-stranded DNA; ATG indicates the methionine initiation codon and the total length of the clone in base pairs is also indicated.

Figure 7:
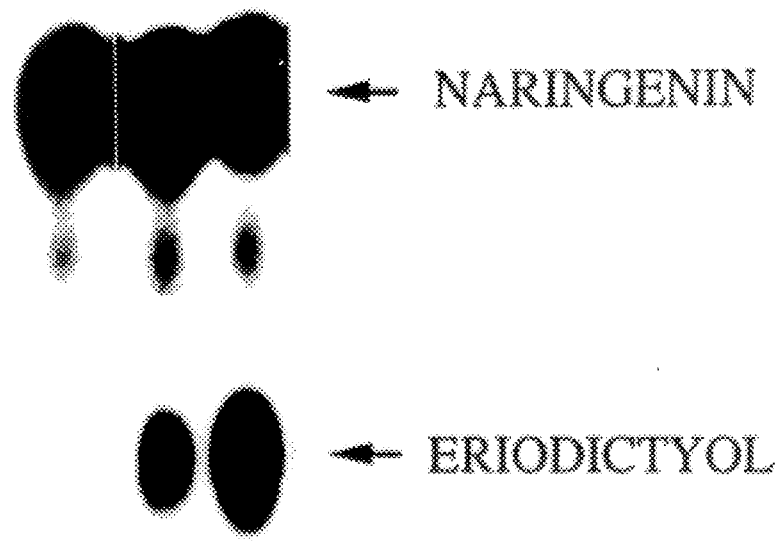

FIG. 7 shows a 3'-hydroxylase assay of yeast extracts using $^3$H-naringenin as substrate. The autoradiograph shows conversion of $^3$H-naringenin to the 3'-hydroxylated derivative eriodictyol by an extract of yeast transformed with the plasmid pCGP621 (1, 2). No 3'-hydroxylase activity was detected in untransformed yeast (C).

FIG. 8 shows nucleotide sequence (SEQ ID NO:51) and predicted amino acid sequence (SEQ ID NO:52) for the insert from pCGP635. These sequences may be used as probes for the isolation of putative rose 3'-hydroxylase cDNA clones.

FIGS. 9A and B show nucleotide sequence (SEQ ID NO:53) and predicted amino acid sequence (SEQ ID NO:54) for the insert from pCGP772. These sequences may be used as probes for the isolation of putative carnation 3'-hydroxylase cDNA clones.

FIGS. 10A and B show nucleotide sequence (SEQ ID NO:55) and predicted amino acid sequence (SEQ ID NO:56) for the insert from pCGP773. These sequences may be used as probes for the isolation of carnation putative 3'-hydroxylase cDNA clones.

FIG. 11 shows partial nucleotide sequence (SEQ ID NO:57) and predicted amino acid sequence (SEQ ID NO:58) for insert from pCGP854. These sequences were used as a probe to select a putative 3'-hydroxylase cDNA clone. Underlined amino acids are identical to those of the cDNA insert from pCGP619 between positions 971 and 1091.

The disarmed microorganism Agrobacterium tumefaciens strain AGL0 containing the plasmid pCGP809 was deposited with the Australian Government Analytical Laboratories, 1 Suakin Street, Pymble, New South Wales, 2037, Australia on Mar. 24, 1993 and was given Accession Number

EXAMPLE 1

Isolation of 3'-Hydroxylase and Related Nucleic Acid Sequences

1. Materials and Methods

Chemicals Enzymes and Radioisotopes

Eriodictyol was obtained from Carl Roth KG and naringenin was obtained from Sigma. [$^3$H]-Naringenin (5.7 Ci/mmole) was obtained from Amersham. All enzymes were obtained from commercial sources and used according to the manufacturer's recommendations.

Bacterial Strains

The Escherichia coli strains used were:

DH5α supE44, Δ(lacZYA-ArgF)U169, φ80lacZΔM15, hsdR17 ($r_k-$, $m_k+$),
  recA1, endA1, gyrA96, thi-1, relA1, deoR. (Hanahan, 1983 and BRL, 1986).

XL1-Blue supE44, hsdR17 ($r_k-$, $m_k+$), recA1, endA1, gyrA96, thi-1, relA1,
lac-, [F'proAB, lacI$^q$, lacZΔM15, Tn10(tet$^r$)] (Bullock et al., 1987).

PLK-F' recA, hsdR17 ($r_k-$, $m_k+$), mcrA$^-$, mcrB$^-$, lac$^-$, supE44, galK2, galT22,
  metB1, [F' proAB, lacI$^q$, lacZΔM15, Tn10 (tet$^r$)] (Stratagene).

SOLR e14$^-$ (mcrA), Δ(mcrCB-hsdSMR-mrr)171, sbcC, recB, recJ,
umuC::Tn5(kan$^r$), uvrC,lac, gyrA96, thi-1, relA1, [F'proAB,
lacI$^q$ZΔM15], Su$^-$ (non-suppressing) (Stratagene)

The disarmed Agrobacterium tumefaciens strain AGL0 (Lazo et al., 1991) was obtained from R Ludwig (Department of Biology, University of California, Santa Cruz).

The cloning vector pBluescript was obtained from Stratagene.

Transformation of E. coli and A. tumefaciens

Transformation of the E. coli strain DH5a cells was performed according to the method of Inoue et al. (1990).

The plasmid pCGP809 was introduced into the Agrobacterium tumefaciens strain AGL0 by adding 5 mg of plasmid DNA to 100 mL of competent AGL0 cells prepared by inoculating a 50 mL MG/L (Garfinkel and Nester, 1980) culture and growing for 16 h with shaking at 28° C. The cells were then pelleted and resuspended in 0.5 mL of 85% (v/v) 100 mM CACl$_2$/15% (v/v) glycerol. The DNA-Agrobacterium mixture was frozen by incubation in liquid N$_2$ for 2 min and then allowed to thaw by incubation at 37° C. for 5 min. The DNA/bacterial mixture was then placed on ice for a further 10 min. The cells were then mixed with 1 mL of MG/L media and incubated with shaking for 16 h at 28° C. Cells of A. tumefaciens carrying pCGP809 were selected on MG/L agar plates containing 100 mg/mL gentamycin. The presence of pCGP809 was confirmed by Southern analysis of DNA isolated from the gentamycin-resistant transformants.

Plant Material

Seed of the Petunia F$_1$ hybrid "Old Glory Blue" (OGB) was obtained from Ball Seed, USA.

Chrysanthemum morifolium cultivars were obtained from Baguley Flower and Plant Growers, Victoria.

Flowers of Dianthus caryophyllus cv. Laguna and Rosa hybrida cv. Kardinal were obtained from Van Wyk and Son Flower Supply, Victoria.

Plants were grown in specialised growth rooms with a 14 hr day length at a light intensity of 10,000 lux minimum and a temperature of 22° to 26° C.

Five stages of Petunia flower development were defined as follows:

| Stage 1: | Unpigmented, closed bud (<25 mm in length). |
| Stage 2: | Pigmented, closed bud (25–35 mm in length). |
| Stage 3: | Dark purple bud with emerging corolla (>35 mm in length). |
| Stage 4: | Dark purple opened flower pre-anther dehiscence (>50 mm in length). |
| Stage 5: | Fully opened flower with all anthers dehisced. |

Stages of Chrysanthemum flower development were defined as follows:

| Stage 0: | No visible flower bud. |
| Stage 1: | Flower bud visible: florets completely covered by the bracts. |
| Stage 2: | Flower buds opening: tips of florets visible. |
| Stage 3: | Florets tightly overlapped. |
| Stage 4: | Tips of nearly all florets exposed; outer florets opening but none horizontal. |
| Stage 5: | Outer florets horizontal. |
| Stage 6: | Flower approaching maturity. |

Stages of Dianthus caryophyllus flower development were defined as follows:

| Stage 1: | No visible flower bud. |
| Stage 2: | Flower buds opening: tips of florets visible. |
| Stage 3: | Tips of nearly all florets exposed; outer florets opening, none horizontal. |
| Stage 4: | Outer florets horizontal. |

Stages of Rosa hybrida flower development were defined as follows:

| | |
|---|---|
| Stage 1: | Unpigmented, tightly closed bud (10–12 mm high; 5 mm wide). |
| Stage 2: | Pigmented, tightly closed bud (15 mm high; 9 mm wide). |
| Stage 3: | Pigmented, closed bud; sepals just beginning to open (20–25 mm high; 13–15 mm wide) |
| Stage 4: | Flower bud beginning to open; petals heavily pigmented; sepals have separated (bud is 25–30 mm high and 18 mm wide). |
| Stage 5: | Sepals completely unfolded; some curling. Petals are heavily pigmented and unfolding (bud is 30–33 mm high and 20 mm wide). |

Construction of cDNA Library #1

Twenty grams of stage 3 to 4 Petunia cv. OGB flower limbs tissue was homogenised in 100 mL of PEB (200 mM Tris-HCl (pH 8.6), 60 mM KCl, 30 mM $MgCl_2$, 25 mM EGTA) containing 10 mM vanadyl ribonucleoside complex. Cell debris was removed by filtering the homogenate through sterile Miracloth (Calbiochem). The filtrate was layered on top of a step gradient of 6 mL of PEB containing 25% (w/v) sucrose, 250 units InhibitAce (5-Prime 3-Prime), and 6 mL of PEB containing 50% (w/v) sucrose and 250 units InhibitAce in Ultra-Clear™ Quick-Seal™ (Beckman) centrifuge tubes. The tubes were centrifuged for 3.5 h at 26,000 rpm in a 70 Ti rotor. Membrane-bound polysomes were collected from the 25% sucrose/50% sucrose interface and added to a 4M guanidium isothiocyanate solution. RNA was isolated from the denatured polysomes by pelleting through a 5.7M CsCl cushion, as described by Turpen and Griffith (1986).

A Uni-ZAP™ XR vector kit (Stratagene) was used to construct a directional cDNA library in λZAP using 25 µg of the polysomal RNA as template. The primary library, which contained 250,000 plaque forming units (pfu), was amplified by overnight growth on NZY plates (Sambrook et al., 1989) and the amplified phage stock was eluted in PSB (100 mM NaCl, 8 mM $MgSO_4$, 50 mM Tris-HCl (pH 7.5), 0.01% (w/v) gelatin) as described by Sambrook et al., (1989).

Construction of cDNA Library #2

Total RNA was isolated from the petal tissue of P. hybrida cv. OGB stage 3 to 4 flowers using the method of Turpen and Griffith (1986). Poly(A)$^+$ RNA was selected from the total RNA by three cycles of oligo-dT cellulose chromatography (Aviv and Leder, 1972).

Two micrograms of poly(A)$^+$ RNA were reverse transcribed in a 20 µL volume containing 1×Superscript™ reaction buffer, 10 mM dithiothreitol (DTT), 500 µM dATP, 500 µM dGTP, 500 µM dTTP, 500 µM 5-methyl-dCTP, 0.75 µg oligonucleotide #6 and 2 µL Superscript™ reverse transcriptase (BRL). The reaction mix was incubated at 37° C. for 50 min, 44° C. for 10 min, then placed on ice.

Second strand reaction mix (140 µL) was added to the first strand reaction. The second strand reaction mix consisted of 21 mM Tris-HCl, 104 mM KCl, 5.3 mM $MgCl_2$, 171 µM β-NAD, 11.4 mM $(NH_4)_2SO_4$, 214 µM dATP, 642 µM dCTP, 214 µM dGTP, 214 µM dTTP, 4 mM DTT, 10 µCi $^{32}$P-dCTP (3000 Ci/mMole), 15 units E. coli DNA ligase, 40 units DNA polymerase (Boehringer) and 0.8 units RNAse H. The final mixture was incubated for 150 min at 16° C. To make the double-stranded cDNA blunt-ended, 10 units T4 DNA polymerase was added, and the reaction continued for a further 15 min at 16° C. The reaction was stopped and the cDNA purified by phenol/chloroform extraction, followed by chloroform extraction and ethanol precipitation.

EcoRI adaptors (Promega) were ligated with the cDNA and then kinased using conditions recommended by the manufacturer. The enzymes were denatured by heat (70° C., 20 min) and the DNA was purified by phenol/chloroform extraction and ethanol precipitation. The cDNA was digested with 50 units XhoI (Boehringer) in a reaction volume of 100 µL, using conditions recommended by the manufacturer. The enzyme was heat killed (70° C., 20 min) and the mixture passed through an S400 spun column (Pharmacia) which had been equilibrated in STE buffer (Sambrook et al., 1989).

The eluate was phenol/chloroform extracted and ethanol precipitated. After microcentrifugation at 4° C. for 30 min the cDNA pellet was rinsed with 70% (v/v) ethanol, air dried and resuspended in 10 µL of TE buffer (10 mM Tris-HCl (pH 7.5), 1 mM EDTA).

NA-45 membrane (Schleicher and Schuell) was used to isolate cDNA in the size range of 1.3 to 2.5 kb from a 7.5 µL sample that had been electrophoresed through a 1% (w/v) agarose gel.

The size fractionated cDNA was ligated with 1 µg λZAPII EcoRI/XhoI/CIAP treated vector (Stratagene) in 5 µL reaction buffer consisting of 50 mM Tris-HCl (pH 7.0), 10 mM $MgCl_2$, 10 mM DTT, 1 mM ATP and 2 units T4 DNA ligase. The reaction was performed at 4° C. for 2 days.

After leaving at room temperature for 2 h, the ligation reaction mixture was packaged using the Packagene system (Promega). The total number of recombinants was 270,000 pfu.

An amount of 150,000 pfu of the packaged cDNA was plated at 10,000 pfu per 15 cm diameter plate after transfecting PLK-F cells. The plates were incubated at 37° C. for 8 h, then stored overnight at 4° C. Duplicate lifts were taken onto Colony/Plaque Screen™ filters (DuPont) and treated as recommended by the manufacturer.

Construction of cDNA Library #3

Total RNA was isolated from the petal tissue of Chrysanthemum morifolium cv. Dark Pink Pompom (Reference Number 5999), stages 1, 2 and 3 flowers, again using the method of Turpen and Griffith (1986). Poly(A)$^+$ RNA was selected from the total RNA, as for P. hybrida, by three cycles of oligo-dT cellulose chromatography (Aviv and Leder, 1972). Two micrograms of poly(A)$^+$ RNA were used as template for cDNA synthesis, as outlined above for P. hybrida.

Following fractionation and ligation, the cDNA reaction mixture was packaged using the Packagene system (Promega). The total number of recombinants was 37,000 pfu.

An amount of 300,000 pfu (of amplified library) of the packaged cDNA was plated at 20,000 pfu per 15 cm diameter plate after transfecting XL1-Blue cells. The plates were incubated at 37° C. for 8 h, then stored overnight at 4° C. Duplicate lifts were taken onto Colony/Plaque Screen™ filters (DuPont) and treated as recommended by the manufacturer.

Preparation of PCR Templates

1. Plasmid DNA

DNA was isolated using an alkaline lysis procedure (Sambrook et al.; 1989). Plasmid DNA was further purified by banding on a CsCl gradient. This DNA was used as template for PCR.

2. Chrysanthemum Genomic DNA

For isolation of total DNA, 5 g of Chrysanthemum petal tissue was frozen in liquid nitrogen and ground to a fine powder in a cold mortar and pestle. Ground tissue was extracted in 5 mL of phenol:chloroform, followed by 5 mL of NTMES buffer (0.01M NaCl; 0.1M Tris pH 8.5; 5 mM $MgCl_2$; 1 mM EDTA; 1% SDS). The aqueous phase was re-extracted with 5 mL of phenol:chloroform and the aqueous phase collected after centrifugation. DNA was spooled from this solution after addition of 0.5 mL 3M NaAc, pH 5.8 and two volumes of ethanol. The final pellet was resuspended in 2 mL TE buffer and the concentration determined prior to use in PCR.

3. Dianthus cDNA

Total RNA was isolated from the petal tissue of *D. caryophyllus* cv. Laguna stage 3 flowers, likewise using the method of Turpen and Griffith (1986). Poly(A)$^+$ RNA was selected from the total RNA by Oligotex dT-30 (Takana, Japan) following the manufacturer's protocol, and two micrograms were reverse transcribed using Superscript™ reverse transcriptase as recommended by the manufacturer. The cDNA was dissolved in 10 mL TE buffer. For PCR reactions, 5 mL were used as template. Conditions for PCR are described below.

4. Rosa cDNA

Total RNA was prepared from the buds of *Rosa hybrida* cv. Kardinal stage 1. At this stage, buds were 1.0–1.2 cm high and approximately 0.5 cm wide. They were completely closed and no pigment was visible when the sepals were dissected away.

Frozen tissue (1–3 g) was ground in liquid nitrogen with a mortar and pestle, placed in 25 mL pre-chilled Buffer A [0.2M boric acid, 10 mM EDTA (sodium salt) (pH 7.6)] and homogenized briefly. The extract was mixed on a rotary shaker until it reached room temperature and an equal volume of phenol/chloroform (1:1 v/v), equilibrated with Buffer A, was added. After mixing for a further 10 min, the RNA preparation was centrifuged at 10,000×g for 10 min at 20° C. The upper aqueous phase was retained and the phenol interface re-extracted as above. The aqueous phases were pooled and adjusted to 0.1M sodium acetate (pH 6.0), 2.5 volumes 95% ethanol were added and the mixture was stored at −20° C. overnight.

The preparation was centrifuged at 10,000×g for 10 min at 4° C., the pellet dissolved gently in 20 mL Buffer B [25 mM boric acid, 1.25 mM EDTA (sodium salt), 0.1M NaCl (pH 7.6)] and 0.4 volumes 2-butoxyethanol (2BE) were added. This solution was incubated on ice for 30 min. It was then centrifuged at 10,000×g for 10 min at 0° C. and the supernatant carefully collected. After addition of 1.0 volume of 2BE and incubation on ice for a further 30 min, the supernatant was again centrifuged at 10,000×g for 10 min at 0° C. The resulting pellet was gently washed with Buffer A:2BE (1:1 v/v), then with 70% (v/v) ethanol, 0.1M potassium acetate and finally with 95% ethanol. The pellet was air dried and dissolved in 1 mL diethyl pyrocarbonate (DEPC) -treated water. This was adjusted to 3M lithium chloride, left on ice for 60 min and centrifuged at 10.000×g for 10 min at 0° C. The pellet was washed twice with 3M LiCl and then with 70% ethanol, 0.1M potassium acetate.

The resulting RNA pellet was dissolved in 400 mL DEPC-treated water and extracted with an equal volume of phenol/chloroform. The RNA mix was then centrifuged at 10,000×g for 5 min at 20° C., the aqueous phase collected and made to 0.1M sodium acetate, and a further 2.5 volumes of 95% ethanol were added. After 30 min incubation on ice, the mix was centrifuged at 13,000 rpm (5,000×g) for 20 min at 20° C. and the RNA pellet resuspended gently in 400 mL DEPC-treated water.

Poly (A)$^+$ RNA was selected from the total RNA by Oligotex dT-30 (Takana, Japan) following the manufacturer's protocol.

Double-stranded cDNA was synthesized from 2 mg poly (A)$^+$ RNA using the same method as described above for the construction of the Petunia cDNA library #2. The cDNA was dissolved in 10 mL TE buffer.

Synthesis of Oligonucleotides

Oligonucleotides and primers were synthesized on an Applied Biosystems PCR-Mate DNA synthesizer using methods recommended by the manufacturer. The oligonucleotides and primers synthesized were, 5'-3':

| | |
|---|---|
| Oligo 1 (SEQ ID NO:1): | GTTCAATTCGGAATGATG |
| Oligo 2 (SEQ ID NO:2): | GCTGCACTTAATCCATAT |
| Oligo 3 (SEQ ID NO:3): | GGATGACTCAAACAGCTATGACCATG |
| Oligo 4 (SEQ ID NO:4): | TGCATAGCTTTTGGG |
| Oligo 5 (SEQ ID NO:5): | CCIGG(A/G)CAIATIC(G/T)(C/T)(C/T)TICCIGCICC(A/G)AAIGG |
| Oligo 6 (SEQ ID NO:6): | GAGAGAGAGAGAGAGAGAG ATCTCGAGTTTTTTTTTTTTTTTTTT |
| Oligo 7 (SEQ ID NO:7): | CCIGC(A/G)CAIATIC(G/T)IC(T/G)ICCIGCICC(A/G)AAIGG |
| primer −40 (SEQ ID NO:8) | GTTTTCCCAGTCACGAC |
| primer 190 (SEQ ID NO:9) | TTGGAGTGGGCAATGGC |
| primer 191 (SEQ ID NO:10 | CTGCTGCAAACAAGTCC |
| poly-T (SEQ ID NO:11) | TTTTTTTTTTTTTTTTTT(AGC) |

The basis for the design of oligo 5 was as follows: Amino acid sequences from the putative haem-binding domain of an avocado cytochrome P450 (Bozak et al., 1990) and the corresponding sequences encoded by the two petunia cytochrome P450 homologues pCGP142 and pCGP147 were aligned:

avocado(SEQ ID NO:12) P F G A G R R G C P G
pCGP142(SEQ ID NO:13) P F G A G K R I C P G
pCGP147(SEQ ID NO:14) P F G S G R R I C P G The consensus amino acid sequence of the haem-binding region for the three plant cytochromes P450 could thereby be seen to be:

(SEQ ID NO:15) P F G A(S) G R(K) R I(G) C P G

Possible permutations of nucleotide sequence that could encode the amino acids found in the haem-binding domain of the three cytochrome P450 molecules could then be deduced:

(SEQ ID NO:16)
5'- CCX TTT GGX GCX GGX AGX CGX ATX TGT CCX GGX -3'
         C        AG       CA  A   GG       C
                                   T

X indicates nucleotide positions where all four nucleotides (A,C,G and T) can be used. Oligo 5 was designed to complement a subset of the consensus sequence derived from the three plant cytochromes P450. Deoxyinosine (I) was used predominantly when base degeneracy was greater than three. The resulting oligonucleotide sequence was as shown above.

Polymerase Chain Reactions
1. Amplification of Cloned Cytochrome P450 Sequences

For amplification of cloned Petunia cytochrome P450 sequences, PCR mixes contained 100 ng of plasmid template, 10 mM Tris-HCl (pH 8.3), 50 mM KCl, 1.25 mM $MgCl_2$, 0.2 mM each dNTP, 1.0 µM each primer and 0.5 unit AmpliTaq DNA Polymerase (Cetus). Reaction mixes (100 µl) were cycled 30 times between 95° C. for 1 min, 42° C. for 1 min and 72° C. for 2 min.

2. Amplification of Dianthus Sequences Related to Petunia 3'-hydroxylase

PCR mixes contained 100 ng of cDNA template, 10 mM Tris-HCl (pH 8.3), 50 mM KCl, 1.5 mM $MgCl_2$, 0.001% (w/v) gelatin, 0.2 mM each dNTP, 1.0 µM each primer and 5 units AmpliTaq DNA Polymerase (Cetus). Reaction mixes (100 ml) were cycled firstly through 95° C. for 3 min, 55° C. for 1 min and 72° C. for 1 min, then through a further 39 cycles between 95° C., 55° C. and 72° C. each for 1 min. Amplified products were gel-purified using Seaplaque low melting agarose (FMC). The mixture was heated until the agarose melted and extracted with TE-saturated phenol. The aqueous phase was then extracted with phenol/chloroform and the amplified products precipated with ethanol. Following gel-purification, the amplified products were cloned directly into the ddT-tailed pBluescript vector described by Holton and Graham (1991).

3. Amplification of Chrysanthemum Sequences Related to Petunia 3'-hydroxylase

Chrysanthemum reaction mixes contained 200 ng of genomic DNA template, 10 mM Tris-HCl (pH 8.3), 50 mM KCl, 2.5 mM $MgCl_2$, 0.001% (w/v) gelatin, 0.2 mM each dNTP, 1.0 µM each primer and 5 units AmpliTaq DNA Polymerase (Cetus). Reaction volumes of 50 mL were cycled 35 times between 95° C., 55° C. and 72° C., each for 90 s. Amplified products were gel-purified using Geneclean (Bio 101 Inc.) and cloned directly into the ddT-tailed pBluescript vector described by Holton and Graham (1991).

4. Amplification of Rosa Sequences Related to Petunia 3'-hydroxylase

Rosa reaction mixes contained 1 µL of a 10-fold dilution of ds cDNA prepared as described above, 10 mM Tris-HCl (pH 8.3), 50 mM KCl, 2.5 mM $MgCl_2$, 0.001% (w/v) gelatin, 0.2 mM each dNTP, 1.0 µM each primer and 5 units AmpliTaq DNA Polymerase (Cetus). Reaction volumes of 50 mL were cycled 30 times between 95° C. for 1 min, 55° C. for 1 min and 72° C. for 3 min. Amplified products were gel-purified using Geneclean (Bio 101 Inc.) and cloned directly into the ddT-tailed pBluescript vector described by Holton and Graham (1991).

Screening of cDNA Libraries

Duplicate plaque lifts from cDNA library #2 were hybridized and washed as follows: High stringency conditions (hybridization: 50% (v/v) formamide, 6×SSC, 1% (w/v) SDS at 42° C. for 16 h and washing: 2×SSC, 1% SDS at 65° C. for 2×15 min followed by 0.2×SSC, 1% SDS at 65° C. for 2×15 min) were used to detect sibling clones and low stringency conditions (hybridization: 20% formamide, 6×SSC, 1% SDS at 42° C. for 16 h and washing: 6×SSC, 1% SDS at 65° C. for 1 h) were used to detect related sequences.

Lifts from cDNA library #3 were hybridized and washed as follows: For the primary screening, using the Petunia 3'-hydroxylase cDNA EcoRI-XhoI insert from pCGP619 (see FIG. 6), hybridization conditions were 20% (v/v) formamide, 1M NaCl, 10% (w/v) dextransulphate at 37° C. for 16 h and washing conditions were 0.1×SSC, 1% (w/v) SDS at room temperature. For the secondary screening, using the EcoRI-XhoI insert from pCGP854, conditions were identical except that the hybridization reaction took place at 42° C. for 16 h.

$^{32}$P-Labelling of DNA Probes

DNA fragments (50 to 100 ng) were radioactively labelled with 50 µCi of [α-$^{32}$P]-dCTP using an oligolabelling kit (Bresatec). Unincorporated [α-$^{32}$P]-dCTP was removed by chromatography on a Sephadex G-50 (Fine) column.

DNA Sequence Analysis

DNA sequencing was performed essentially by the method of Sanger et al. (1977) using the Sequenase enzyme (USB, version 2.1). The complete sequence of clones pCGP602 and pCGP619 was determined by compilation of sequence from different M13 −mp18 and −mp19 (Norrander et al., 1983; Yanisch-Perron, 1985) subclones obtained using standard cloning procedures (Sambrook et al., 1989). For some regions it was necessary to synthesise specific oligonucleotide primers to obtain overlapping sequence data, including primers −40, 190 191 and poly-T.

A restriction map of pCGP619 showing the position of several of these sequences may be seen in FIG. 6.

Homology searches against Genbank, SWISS-PROT and EMBL databases were performed using the FASTA and TFASTA programs (Pearson and Lipman, 1988).

3'-Hydroxylase Assay

3'-Hydroxylase enzyme activity was measured using a modified version of the method described by Stotz and Forkmann (1982). The assay reaction mixture typically contained 100 µL of yeast extract, 5 µL of 50 mM NADPH in assay buffer (100 mM potassium phosphate (pH 8.0), 1 mM EDTA and 20 mM 2-mercaptoethanol) and 10 µCi of [$^3$H]-naringenin and was made up to a final volume of 210 µL with the assay buffer. Following incubation at 23° C. for 2–16 h, the reaction mixture was extracted with 0.5 mL of ethylacetate. The ethylacetate phase was dried under vacuum and then resuspended in 10 µL of ethylacetate. The tritiated flavonoid molecules were separated on cellulose thin layer plates (Merck Art 5577, Germany) using a chloroform: acetic acid: water (10:9:1 v/v) solvent system. At the completion of the chromatography the TLC plates were sprayed with 7% 2,5-diphenyloxazol in diethyl ether. The reaction products were localised by autoradiography and identified by comparison to non-radioactive naringenin and eriodictyol standards which were run alongside the reaction products and visualised under UV light.

Construction of pCGP621

A 1.8 kb EcoRI-XhoI fragment that included the entire cDNA insert from pCGP619 was ligated with the 8 kb EcoRI-SalI fragment from pYHCC101 (Tanaka et al., 1988). The resulting plasmid, pCGP621, contained the pCGP619 cDNA fragment ligated in a sense orientation behind the yeast glyceraldehyde-3-phosphate dehydrogenase promoter.

Yeast Transformation

The yeast strain G-1315 (Mat α, trpl) (Ashikari et al., 1989) was transformed with pCGP621 according to Ito et al. (1983). The transformants were selected by their ability to restore G-1315 to tryptophan prototrophy.

Preparation of Yeast Extracts for Assay of 3'-hydroxylase Activity

A single isolate of G-1315/pCGP621 was used to inoculate 20 ml of YNBC [1.2% (w/v) yeast nitrogen base without amino acids (Difco), 2% (w/v) glucose and 0.3% (w/v) casamino acid (Difco)] which was subsequently incubated for 2 days at 30° C. Cells were collected by centrifugation, washed once with TE buffer, once with buffer A [10 mM Tris-HCl (pH 7.5), 0.65M sorbitol, 0.1 mM DTT, 0.1 mM EDTA], and then resuspended in buffer B [10 mM Tris-HCl, (pH 7.5), 1.2M sorbitol, 0.1 mM DTT, 0.1 mM EDTA]

containing zymolyase (0.1 mg/mL) (Seikagakukogyo, Japan). Following incubation for 1 h at 30° C. the cells were pelleted by centrifugation and resuspended in 400 μL of buffer A. The cell suspension was then vortexed with glass beads (diameter=0.4 mm) for 2 min and a 100 μL sample was assayed for activity.

Construction of pCGP293

The expression binary vector pCGP293 was derived from the Ti binary vector pCGN1559 (McBride and Summerfelt, 1990). Plasmid pCGN1559 was digested with KpnI and the overhanging 3' ends were removed with T4 DNA polymerase according to standard protocols (Sambrook et al., 1989). The vector was then further digested with XbaI and the resulting 5' overhang was repaired using the Klenow fragment of DNA polymerase I. The vector was then re-ligated to give pCGP67. A 1.97 kb PstI fragment containing the Mac promoter, mas terminator and various cloning sites (Comai et al., 1990) was isolated from pCGP40 and inserted into the PstI site of pCGP67 to give pCGP293.

Plasmid pCGP40 was constructed by removing the GUS gene (Jefferson et al., 1987) as a BamHI-SacI fragment from pCGN7334 and replacing it with the BamHI-SacI fragment from pBluescribe M13⁻ that includes the multicloning site. Plasmid pCGN7334 (obtained from Calgene Inc., Calif., USA), was constructed by inserting the fragment containing the Mac-GUS-mas gene fusion into the XhoI site of pCGN7329 (Comai et al., 1990).

Construction of pCGP809

Plasmid pCGP809 was constructed by cloning the cDNA insert from pCGP619 in a sense orientation behind the Mac promoter (Comai et al., 1990) of pCGP293. The 1.8 kb BamHI-KpnI fragment containing the cDNA insert was isolated from pCGP619 and ligated with a BamHI-KpnI digest of pCGP293. Correct insertion of the insert in pCGP809 was established by restriction analysis of DNA isolated from gentamycin-resistant transformants.

Petunia Transformation a. Plant Material

Petunia hybrida (Skr4×Sw63) seeds were sterilized in 1.25% (w/v) sodium hypochlorite for 10 minutes and rinsed three times in sterile water. Sterilized seeds were soaked in 100 mg/L gibberellic acid ($GA_3$) solution for 16 to 20 h. They were then germinated for 2 weeks on 10% (w/v) MS (Murashige and Skoog, 1962) medium supplemented with 1% (v/v) sucrose and 0.8% (w/v) Difco Bacto agar. Young seedlings were transferred to MS medium supplemented with 3% (w/v) sucrose for 3 weeks before being transferred to Jiffy peat pellets (Jiffy Products Ltd, Norway), kept under mist and illuminated (135 μE. mercury halide light, 22° C.) for 2 to 3 weeks. These young plants were then transferred to a growth cabinet (68 μE. cool white fluorescent light, 25° C.). For co-cultivation, young leaves were harvested and sterilized in 1.35% (w/v) sodium hypochlorite for 2 min followed by rinsing three times in sterile water. Leaf tissue was then cut into 25 mm² squares and precultured on MS media supplemented with 0.05 mg/L kinetin and 1.0 mg/L 2,4-dichlorophenoxyacetic acid (2,4-D) for 24 h.

b. Co-cultivation of Agrobacterium and Petunia Tissue

*Agrobacterium tumefaciens* strain AGL0 (Lazo et al., 1991) containing the binary vector pCGP809 was maintained at 4° C. on MG/L (Garfinkel and Nester, 1980) agar plates with 100 mg/L gentamycin. A single colony was grown overnight in liquid medium containing 1% (w/v) Bacto-peptone, 0.5% (w/v) Bacto-yeast extract and 1% (w/v) NaCl. A final concentration of $5 \times 10^8$ cells/mL was prepared the next day by dilution in liquid MS medium containing 3% (w/v) sucrose (BPM). Leaf discs were dipped for 5 min into BPM containing AGL0/pCGP809. The leaf discs were then blotted dry and placed on co-cultivation media for 4 days. The co-cultivation medium consisted of SH medium (Schenk and Hilderbrandt, 1972) supplemented with 0.05 mg/L kinetin and 1.0 mg/L 2,4-D and included a feeder layer of tobacco cell suspension spread over the co-cultivation medium with a filter paper placed on top of the tobacco cell suspension.

c. Recovery of Transgenic Petunia Plants

After co-cultivation, the leaf discs were transferred to selection media consisting of fresh MS medium supplemented with 3% (w/v) sucrose, 2 mg/L a-benzylaminopurine (BAP), 100 mg/L kanamycin, 350 mg/L cefotaxime, 0.3% (w/v) Gelrite Gellan Gum (Schweizerhall). After 3 weeks, regenerating explants were transferred to fresh medium. Adventitious shoots which survived the kanamycin selection were isolated and transferred to BPM containing 100 mg/L kanamycin and 350 mg/L cefotaxime for root induction. All cultures were maintained under a 16 h photoperiod (60 μE. cool white fluorescent light) at 23±2° C. When roots reached 2–3 cm in length the transgenic petunia plantlets were transferred to autoclaved Debco 51410/2 potting mix in 8 cm tubes. After 4 weeks plants were replanted into 15 cm pots using the same potting mix and maintained at 23° C. under a 14 h photoperiod (300 μE. mercury halide light).

2. Results

Isolation of Cytochrome P450 Homologues From cDNA Library #1

The isolation of five petunia cDNA clones that have regions of sequence similarity with cytochrome P450 enzymes has been described previously (International Patent Application No. PCT/AU92/00334). Partial sequences of these clones, designated pCGP142, pCGP147, pCGP158, pCGP160 and pCGP454, are shown in FIG. 2. A mixed probe of $^{32}$P-labelled DNA fragments that included the coding regions of these five cytochrome P450 homologues (see FIGS. 2A and B) was used to screen 50,000 recombinants from cDNA library #1 for related sequences. A total of 152 hybridizing clones were detected under low stringency hybridization and washing conditions. A further 13 different cytochrome P450 homologues were identified by sequence analysis of DNA isolated from the hybridizing clones.

One of these clones, designated pCGP174, was shown to correspond to the Hf1 locus of Petunia (see International Patent Application No. PCT/AU92/00334). The nucleotide sequence of a full-length version of this clone, pCGP602, isolated from cDNA library #2 is shown in FIG. 3. Ten of the thirteen other cytochrome P450 homologues isolated in the screen, pCGP161, pCGP162, pCGP163, pCGP165, pCGP166, pCGP167, pCGP168, pCGP169, pCGP171 and pCGP173 were used as a mixed probe to screen cDNA library #2 for further cytochrome P450 homologues (see next section).

Isolation of the Cytochrome P450 Homologue pCGP619 from Petunia

A mixed probe of $^{32}$P-labelled cDNA inserts from pCGP161, pCGP162, pCGP163, pCGP165, pCGP166, pCGP167, pCGP168, pCGP169, pCGP171 and pCGP173 (FIG. 4) was used to screen $1.5 \times 10^5$ recombinants from cDNA library #2. Over 200 hybridizing clones were detected with low stringency hybridization and washing in 2×SSC and 1% SDS, at 65° C. Twenty-five of these clones hybridized to probes that included the internal HincII-EcoRV and EcoRV-HindIII fragments of pCGP602 (FIG. 3) under low stringency conditions, but not under high stringency conditions. Sequence analysis of this group of clones revealed that seventeen were siblings of pCGP602 (shown previously to correspond to the Hf1 locus of petunia—International Patent Application No. PCT/AU92/00334) and six were siblings of another petunia cDNA clone encoded by the Hf2 locus (International Patent Application No. PCT/AU92/00334). One clone showed no sequence homology to cytochromes P450, and one, designated pCGP619, showed 57% and 39% sequence homology to pCGP602 at the nucleotide and amino acid levels, respectively. The complete nucleotide sequence and deduced amino acid sequence of the pCGP619 cDNA are shown in FIG. 5, and the restriction map outlining the sequencing strategy is shown in FIG. 6.

Expression of pCGP619 cDNA in Yeast

The cDNA insert from pCGP619 was ligated in a sense orientation behind the glyceraldehyde-3-phosphate dehydrogenase promoter in the yeast vector pYHCC101. The resulting construct, designated pCGP621, was then transformed into the yeast strain G-1315 (Ashikari et al., 1989). 3'-Hydroxylase activity was detected in extracts of G-1315/pCGP621, but not in extracts of the non-transgenic yeast (FIG. 7). From this it was concluded that the cDNA insert from pCGP619 encoded a 3'-hydroxylase.

Expression of a 3'-hydroxylase cDNA in Petunia

The binary plasmid construct designated pCGP809 was introduced into the $F_1$ petunia hybrid Skr4×Sw63 using Agrobacterium-mediated gene transfer. Leaf discs of Skr4×Sw63 were co-cultivated with AGL0/pCGP809 and integration of the pCGP619 cDNA insert in the Skr4×Sw63 genome was confirmed by Southern analysis of plants obtained after kanamycin selection.

The expression of the introduced 3'-hydroxylase cDNA in the Skr4×Sw63 hybrid had a noticeable effect on flower colour. In parts of the petals of Skr4×Sw63 the colour changed from light pink to red. The colour change observed may be described in terms of the numbers from the Royal Horticultural Society's Colour Chart as having shifted from 55D–56C/D to 54A–55A. Other biochemical and physiological conditions will affect the individual outcome and the citing of the specific colour change achieved by expression of the 3'-hydroxylase cDNA in transgenic plants should not be interpreted as limiting the possible range of colour changes which may be observed.

Generation of Mutants and Derivatives of Flavonoid 3'-hydroxylase

Using standard mutagenic techniques as hereinbefore disclosed, a range of mutants, derivatives and parts of flavonoid 3'-hydroxylase are obtainable, which may be useful in accordance with the present invention. For specific descriptions and protocols for such mutagenic techniques reference can conveniently be made to Sambrook et al. (1989). Examples of mutants, derivatives and parts of 3'-hydroxylase which are isolatable and contemplated herein include the following:

| 5' | GCT | AAA | GAG | TTT | AAG | GAA | 3' | | | | | (SEQ ID NO:17) |
|---|---|---|---|---|---|---|---|---|---|---|---|---|
| | Ala | Lys | Glu | Phe | Lys | Glu | | | | | | (SEQ ID NO:18) |
| 5' | AAG | AAA | CTT | CCA | CCA | GGT | CCA | TTT | 3' | | | (SEQ ID NO:19) |
| | Lys | Lys | Leu | Pro | Pro | Gly | Pro | Phe | | | | (SEQ ID NO:20) |
| 5' | TTG | GAG | TGG | GCA | ATG | GC | 3' | | | | | (SEQ ID NO:21) |
| | Leu | Glu | Trp | Ala | Met | Ala | | | | | | (SEQ ID NO:22) |
| 5' | G | GAC | TTG | TTT | GCA | GCA | GG | 3' | | | | (SEQ ID NO:23) |
| | | Asp | Leu | Phe | Ala | Ala | Gly | | | | | (SEQ ID NO:24) |
| 5' | CCA | TTT | GGT | GCT | GGT | CGA | AGA | ATT | TGC | CCT | GG 3' | (SEQ ID NO:25) |
| | Pro | Phe | Gly | Ala | Gly | Arg | Arg | Ile | Cys | Pro | Gly | (SEQ ID NO:26) |

Detection of Related Sequences in Plant Species Other Than Petunia

Using standard Southern analysis techniques, a "nursery blot" was prepared of DNA isolated from a variety of plant species, including apple, carnation, cornflower, morning glory and rose to screen for genetic sequences related to the petunia 3'-hydroxylase. Results clearly showed the presence of related genetic sequences in all the plants tested. The nursery blot comprised lanes 1–5 containing approximately 10 mg DNA from each of the above-mentioned species, respectively. The probe DNA used was the HindIII-EcoRV fragment from pCGP619. Southern analysis was conducted over a range of stringency conditions. Suitable stringency conditions indicating the presence of a number of similar sequences in each species were overnight incubation in 50% formamide, 1M NaCl, 1% SDS, 10% dextran sulphate at 42° C., followed by 3×30 min washes in 2×SSC, 1% SDS at 60° C.

Isolation of a Cytochrome P450-homologous PCR Product From Rosa

Double-stranded rose petal cDNA, synthesized as described in Materials and Methods, was used as the template for amplification of sequences related to the petunia 3'-hydroxylase using oligonucleotides 7 and 190. A PCR product of approximately 400 bp was ligated into pBluescript and one of the recombinant plasmids recovered was designated pCGP635. The nucleotide sequence and deduced amino acid sequence of the pCGP635 insert are shown in FIG. 8. This insert shows 60% similarity at the nucleotide level to the Petunia pCGP619 cDNA.

Isolation of Cytochrome P450-homologous PCR Products From Dianthus

Single-stranded carnation petal cDNA synthesized as described in Materials and Methods, was used as the template for amplification of sequences related to the petunia 3'-hydroxylase using oligonucleotides 7 and 190. A PCR product of approximately 400 bp was ligated into pBluescript. Sequence analysis of the recombinant plasmids revealed that two different cytochrome P450 homologues had been amplified and cloned. Representative clones of these two molecules were designated pCGP772 and pCGP773. The nucleotide sequence and deduced amino acid sequence of each insert are shown in FIGS. 9 and 10, respectively. Comparison of the deduced amino acid sequences with that of other cytochrome P450s yielded the following results:

|  | pCGP772 | pCGP773 |
|---|---|---|
| pCGP619 | 59.2% | 64.8% |
| pCGP158 (Haem binding area) | 62.9% | 61.1% |
| pCGP168 (Haem binding area) | 59.5% |  |
| Avocado cytochrome P450 |  | 57.8% |

Isolation of a Cytochrome P450-homologous PCR Product From Chrysanthemum

Chrysanthemum genomic DNA isolated as described in the Materials and Methods was used as the template for amplification of sequences related to the petunia 3'-hydroxylase using oligonucleotides 7 and 190. A PCR product of approximately 400 bp was ligated into the ddT-tailed pBluescript and one of the recombinant plasmids recovered was designated pCGP854. The nucleotide sequence and deduced amino acid sequence of 120 of these base pairs are shown in FIG. 11. This sequence was compared with that from the Petunia cDNA clone pCGP619, shown in FIG. 5, and shows 73% and 65% similarity at the DNA and amino acid level, respectively, to the segment of sequence between positions 971 and 1091.

Isolation of a Chrysanthemum Petal cDNA Clone With Sequence Similarity to the Petunia 3'-hydroxylase The cDNA insert from pCGP619 was used to screen cDNA library #3 for related sequences. Using the hybridization and washing conditions described in the Materials and Methods, 64 hybridizing clones were detected. Twelve of these clones also hybridized to the insert from pCGP854. Sequence analysis of a putative full-length clone that hybridized to both the pCGP619 and pCGP854 probes revealed that it included an identical sequence to that of the PCR product sequence shown in FIG. 11 and therefore encodes a putative chrysanthemum 3'-hydroxylase.

Expression of a Chrysanthemum Petal cDNA Clone in Yeast

The petal cDNA clone can be ligated in a sense orientation behind the glyceraldehyde-3-phosphate dehydrogenase promoter in the yeast vector pYHCC101. The resulting construct is then transformed into the yeast strain G-1315 (Ashikari et al., 1989). Activity of the 3'-hydroxylase can be detected in extracts of G-1315 plus construct, but not in extracts of non-transgenic yeast. From this result it can be concluded that the cDNA insert encodes a 3'-hydroxylase.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

REFERENCES

Ashikari, T., Kiuchi-Goto, N., Tanaka, Y., Shibano, Y., Amachi, T., and Yoshizumi, H. Appl. Microbiol. Biotechnol. 30: 515–520, 1989.

Aviv, H. and Leder, P., Proc. Natl. Acad. Sci. USA 69: 1408–1412, 1972.

Bethesda Research Laboratories. BRL pUC host: E. coli DH5a™ competent cells. Bethesda Res. Lab. Focus. 8(2): 9, 1986.

Bozak, K. R., Yu, H., Sirevag, R. and Christoffersen, R. E., Proc. Natl. Acad. Sci. USA 87: 3904–3908, 1990.

Bullock, W. O., Fernandez, J. M. and Short, J. M. Biotechniques 5: 376, 1987.

Comai, L., Moran, P. and Maslyar, D., Plant Molecular Biology 15: 373–381, 1990.

Ebel, J. and Hahlbrock, K., In The Flavonoids: Advances in Research Since 1980. Harborne, J. B. (Ed.), Academic Press, New York, USA, 641–679, 1988.

Forkmann, G. Plant Breeding 106: 1–26, 1991.

Garfinkel, D. J. and Nester, E. W. J. Bacteriol. 144: 732–743, 1980.

Hahlbrock, K. and Grisebach, H. Annu. Rev. Plant Physiol. 30: 105–130, 1979.

Hanahan, D. J. Mol. Biol. 166: 557, 1983.

Holton, T. A. and Graham, M. W. Nucleic Acids Research 19: 1156, 1991.

Inoue, H., Nojima, H. and Okayama, H. Gene 96: 23–28, 1990.

Ito, H., Fukuda, Y., Murata, K. and Kimura, A. J. Bacteriol., 153: 163–168, 1983.

Jefferson, R. A., Kavanagh, T. A. and Bevan, M. W. EMBO J. 6(13): 3901–3907, 1987.

Lazo, G. R., Pascal, A. S. and Ludwig, R. A. Bio/technology 9: 963–967, 1991.

McBride, K. E. and Sumerfelt, K. R. Plant Molecular Biology 14: 269–276 1990.

Merrifield, J. Am. Chem. Soc. 85: 2149, 1964.

Murashige, T. and Skoog, F. Physiol. Plant 15: 73–97, 1962.

Norrander, J., Kemp, T. and Messing, J. Gene 26: 101, 1983.

Pearson, W. R. and Lipman, D. J. Proc. Natl. Acad. Sci. USA 85: 2444–2448, 1988.

Sambrook, J., Fritsch, E. F. and Maniatis, T. Molecular Cloning: A Laboratory Manual (2nd edition). Cold Spring Harbor Laboratory Press, USA, 1989.

Sanger, F., Nicklen, S. and Coulson, A. Proc. Natl. Acad. Sci. USA 74: 5463–5467, 1977.

Schenk, R. U. and Hilderbrandt, A. C. Can. J. Bot. 50: 199–204, 1972.

Schram, A. W., Jonsson, L. M. V. and Bennink, G. J. H. Biochemistry of flavonoid synthesis in Petunia hybrida. In: Petunia Sink, K. C. (Ed.) Springer-Verlag, Berlin, Germany pp 68–75, 1984.

Stafford, H. A. Flavonoid Metabolism. CRC Press, Inc. Boca Raton, Fla., USA, 1990.

Stotz, G. and Forkmann, G. Z. Naturforsch 37c: 19–23, 1982.

Tanaka, Y., Ashikari, T., Shibano, Y., Amachi, T., Yoshizumi, H. and Matsubara, H. J. Biochem. 103: 954–961, 1988.

Turpen, T. H. and Griffith, O. M. BioTechniques 4: 11–15, 1986.

Wiering, H. and De Vlaming, P. Inheritance and Biochemistry of Pigments. In: Petunia Sink, K. C. (Ed.), Springer-Verlag, Berlin, Germany pp 49–65, 1984.

Yanisch-Perron, C., Vieira, J. and Messing, J. Gene 33: 103, 1985.

We claim:

1. An isolated nucleic acid encoding an enzyme having flavonoid 3'-hydroxylase activity and capable of hydroxylating dihydrokaempferol (DHK), said isolated nucleic acid selected from the group consisting of:

(a) an isolated nucleic acid having the nucleic acid sequence substantially as set forth in SEQ ID NO: 49;

(b) a nucleotide sequence capable of hybridizing to the nucleotide sequence of SEQ ID NO: 49, or a sequence complementary to SEQ ID NO: 49, under hybridization washing conditions of 6×SSC and 1% w/v SDS at 65° C.; and (c) a nucleotide sequence which is at least 50% identical to the nucleotide sequence of SEQ ID NO:49.

2. An isolated nucleic acid according to claim 1 wherein said isolated nucleic acid encodes an enzyme having an amino acid sequence substantially as set forth in SEQ ID NO:50.

3. An isolated nucleic acid according to claim 1 wherein said isolated nucleic acid encodes an enzyme having at least a 29% similarity to SEQ. ID NO:50.

4. An isolated nucleic acid according to any one of claims 1–3 wherein said isolated nucleic acid is genomic DNA or cDNA.

5. An isolated nucleic acid according to any one of claims 1–3 wherein said isolated nucleic acid is contained within a plasmid.

6. An isolated nucleic acid according to claim 4 wherein the plasmid is pCGP619.

* * * * *

SEQUENCE LISTING ( 1 ) GENERAL INFORMATION:

( i i i ) NUMBER OF SEQUENCES: 58

( 2 ) INFORMATION FOR SEQ ID NO:1:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

GTTCAATTCG GAATGATG                                       18

( 2 ) INFORMATION FOR SEQ ID NO:2:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

GCTGCACTTA ATCCATAT                                       18

( 2 ) INFORMATION FOR SEQ ID NO:3:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

GGATGACTCA AACAGCTATG ACCATG                           26

( 2 ) INFORMATION FOR SEQ ID NO:4:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

TGCATAGCTT TTGGG                                               15

( 2 ) INFORMATION FOR SEQ ID NO:5:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: modified_base ( B ) LOCATION: 3..4
            ( D ) OTHER INFORMATION: /mod_base=i ( i x ) FEATURE:
            ( A ) NAME/KEY: modified_base
            ( B ) LOCATION: 9..10
            ( D ) OTHER INFORMATION: /mod_base=i ( i x ) FEATURE:
            ( A ) NAME/KEY: modified_base
            ( B ) LOCATION: 12..13
            ( D ) OTHER INFORMATION: /mod_base=i ( i x ) FEATURE:
            ( A ) NAME/KEY: modified_base
            ( B ) LOCATION: 18..19
            ( D ) OTHER INFORMATION: /mod_base=i ( i x ) FEATURE:
            ( A ) NAME/KEY: modified_base
            ( B ) LOCATION: 21..22
            ( D ) OTHER INFORMATION: /mod_base=i ( i x ) FEATURE:
            ( A ) NAME/KEY: modified_base
            ( B ) LOCATION: 24..25
            ( D ) OTHER INFORMATION: /mod_base=i ( i x ) FEATURE:
            ( A ) NAME/KEY: modified_base
            ( B ) LOCATION: 30..31
            ( D ) OTHER INFORMATION: /mod_base=i ( x i ) SEQUENCE DESCRIPTION: SEQ ID NO:5:

CCNGGRCANA TNCK Y Y TNCC NGCNCCRAAN GG                32

( 2 ) INFORMATION FOR SEQ ID NO:6:

( i ) SEQUENCE CHARACTERISTICS:
            ( A ) LENGTH: 45 base pairs
            ( B ) TYPE: nucleic acid
            ( C ) STRANDEDNESS: single
            ( D ) TOPOLOGY: linear ( i i ) MOLECULE TYPE: DNA (genomic)

( x i ) SEQUENCE DESCRIPTION: SEQ ID NO:6:

GAGAGAGAGA GAGAGAGAGA TCTCGAGTTT TTTTTTTTT TTTTT                45

( 2 ) INFORMATION FOR SEQ ID NO:7:

( i ) SEQUENCE CHARACTERISTICS:
            ( A ) LENGTH: 32 base pairs
            ( B ) TYPE: nucleic acid
            ( C ) STRANDEDNESS: single
            ( D ) TOPOLOGY: linear ( i i ) MOLECULE TYPE: DNA (genomic)

( i x ) FEATURE:
            ( A ) NAME/KEY: modified_base
            ( B ) LOCATION: 3..4
            ( D ) OTHER INFORMATION: /mod_base=i ( i x ) FEATURE:
            ( A ) NAME/KEY: modified_base
            ( B ) LOCATION: 9..10
            ( D ) OTHER INFORMATION: /mod_base=i ( i x ) FEATURE:
            ( A ) NAME/KEY: modified_base
            ( B ) LOCATION: 12..13
            ( D ) OTHER INFORMATION: /mod_base=i ( i x ) FEATURE:
            ( A ) NAME/KEY: modified_base (B) LOCATION: 15..16
(D) OTHER INFORMATION: /mod_base=i (ix) FEATURE:
(A) NAME/KEY: modified_base
(B) LOCATION: 18..19
(D) OTHER INFORMATION: /mod_base=i (ix) FEATURE:
(A) NAME/KEY: modified_base
(B) LOCATION: 21..22
(D) OTHER INFORMATION: /mod_base=i (ix) FEATURE:
(A) NAME/KEY: modified_base
(B) LOCATION: 24..25
(D) OTHER INFORMATION: /mod_base=i (ix) FEATURE:
(A) NAME/KEY: modified_base
(B) LOCATION: 30..31
(D) OTHER INFORMATION: /mod_base=i (xi) SEQUENCE DESCRIPTION: SEQ ID NO:7:

CCNGCRCANA TNCKNCKNCC NGCNCCRAAN GG    32

(2) INFORMATION FOR SEQ ID NO:8:

(i) SEQUENCE CHARACTERISTICS:
(A) LENGTH: 17 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:8:

GTTTTCCCAG TCACGAC    17

(2) INFORMATION FOR SEQ ID NO:9:

(i) SEQUENCE CHARACTERISTICS:
(A) LENGTH: 17 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:9:

TTGGAGTGGG CAATGGC    17

(2) INFORMATION FOR SEQ ID NO:10:

(i) SEQUENCE CHARACTERISTICS:
(A) LENGTH: 17 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:10:

CTGCTGCAAA CAAGTCC    17

(2) INFORMATION FOR SEQ ID NO:11:

(i) SEQUENCE CHARACTERISTICS:
(A) LENGTH: 20 base pairs
(B) TYPE: nucleic acid
(C) STRANDEDNESS: single
(D) TOPOLOGY: linear ( i i ) MOLECULE TYPE: DNA (genomic)

( x i ) SEQUENCE DESCRIPTION: SEQ ID NO:11:

TTTTTTTTT TTTTTTAGC 20

( 2 ) INFORMATION FOR SEQ ID NO:12:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:12:

Pro Phe Gly Ala Gly Arg Arg Gly Cys Pro Gly
1               5                   10

( 2 ) INFORMATION FOR SEQ ID NO:13:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:13:

Pro Phe Gly Ala Gly Lys Arg Ile Cys Pro Gly
1               5                   10

( 2 ) INFORMATION FOR SEQ ID NO:14:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:14:

Pro Phe Gly Ser Gly Arg Arg Ile Cys Pro Gly
1               5                   10

( 2 ) INFORMATION FOR SEQ ID NO:15:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:15:

Pro Phe Gly Ala Ser Gly Arg Lys Arg Ile Gly Cys Pro Gly
1               5                   10

( 2 ) INFORMATION FOR SEQ ID NO:16:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear (i i) MOLECULE TYPE: DNA (genomic)

(x i) SEQUENCE DESCRIPTION: SEQ ID NO:16:

CCNTTTGGNG CNGGNAGNCG NATNTGTCCN GGN    33

(2) INFORMATION FOR SEQ ID NO:17:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (i i) MOLECULE TYPE: DNA (genomic)

(i x) FEATURE:
        (A) NAME/KEY: CDS
        (B) LOCATION: 1..18

(x i) SEQUENCE DESCRIPTION: SEQ ID NO:17:

GCT AAA GAG TTT AAG GAA    18
Ala Lys Glu Phe Lys Glu
 1              5

(2) INFORMATION FOR SEQ ID NO:18:

(i) SEQUENCE CHARACTERISTICS:
        (A) LENGTH: 6 amino acids
        (B) TYPE: amino acid
        (D) TOPOLOGY: linear (i i) MOLECULE TYPE: protein (x i) SEQUENCE DESCRIPTION: SEQ ID NO:18:

Ala Lys Glu Phe Lys Glu
 1              5

(2) INFORMATION FOR SEQ ID NO:19:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (i i) MOLECULE TYPE: DNA (genomic)

(i x) FEATURE:
        (A) NAME/KEY: CDS
        (B) LOCATION: 1..24

(x i) SEQUENCE DESCRIPTION: SEQ ID NO:19:

AAG AAA CTT CCA CCA GGT CCA TTT    24
Lys Lys Leu Pro Pro Gly Pro Phe
 1              5

(2) INFORMATION FOR SEQ ID NO:20:

(i) SEQUENCE CHARACTERISTICS:
        (A) LENGTH: 8 amino acids
        (B) TYPE: amino acid
        (D) TOPOLOGY: linear (i i) MOLECULE TYPE: protein (x i) SEQUENCE DESCRIPTION: SEQ ID NO:20:

Lys Lys Leu Pro Pro Gly Pro Phe
 1              5

(2) INFORMATION FOR SEQ ID NO:21:

( i ) SEQUENCE CHARACTERISTICS:
   ( A ) LENGTH: 17 base pairs
   ( B ) TYPE: nucleic acid
   ( C ) STRANDEDNESS: single
   ( D ) TOPOLOGY: linear ( i i ) MOLECULE TYPE: DNA (genomic)

( i x ) FEATURE:
   ( A ) NAME/KEY: CDS
   ( B ) LOCATION: 1..17

( x i ) SEQUENCE DESCRIPTION: SEQ ID NO:21:

TTG GAG TGG GCA ATG GC                                                17
Leu Glu Trp Ala Met
 1               5

( 2 ) INFORMATION FOR SEQ ID NO:22:

( i ) SEQUENCE CHARACTERISTICS:
      ( A ) LENGTH: 5 amino acids
      ( B ) TYPE: amino acid
      ( D ) TOPOLOGY: linear ( i i ) MOLECULE TYPE: protein ( x i ) SEQUENCE DESCRIPTION: SEQ ID NO:22:

Leu Glu Trp Ala Met
 1               5

( 2 ) INFORMATION FOR SEQ ID NO:23:

( i ) SEQUENCE CHARACTERISTICS:
      ( A ) LENGTH: 18 base pairs
      ( B ) TYPE: nucleic acid
      ( C ) STRANDEDNESS: single
      ( D ) TOPOLOGY: linear ( i i ) MOLECULE TYPE: DNA (genomic)

( i x ) FEATURE:
      ( A ) NAME/KEY: CDS
      ( B ) LOCATION: 2..18

( x i ) SEQUENCE DESCRIPTION: SEQ ID NO:23:

G GAC TTG TTT GCA GCA GG                                              18
  Asp Leu Phe Ala Ala
   1               5

( 2 ) INFORMATION FOR SEQ ID NO:24:

( i ) SEQUENCE CHARACTERISTICS:
      ( A ) LENGTH: 5 amino acids
      ( B ) TYPE: amino acid
      ( D ) TOPOLOGY: linear ( i i ) MOLECULE TYPE: protein ( x i ) SEQUENCE DESCRIPTION: SEQ ID NO:24:

Asp Leu Phe Ala Ala
 1               5

( 2 ) INFORMATION FOR SEQ ID NO:25:

( i ) SEQUENCE CHARACTERISTICS:
      ( A ) LENGTH: 32 base pairs
      ( B ) TYPE: nucleic acid
      ( C ) STRANDEDNESS: single
      ( D ) TOPOLOGY: linear ( i i ) MOLECULE TYPE: DNA (genomic)

( i x ) FEATURE:
    ( A ) NAME/KEY: CDS
    ( B ) LOCATION: 1..32

( x i ) SEQUENCE DESCRIPTION: SEQ ID NO:25:

```
CCA TTT GGT GCT GGT CGA AGA ATT TGC CCT GG                              32
Pro Phe Gly Ala Gly Arg Arg Ile Cys Pro
  1           5                  10
```

( 2 ) INFORMATION FOR SEQ ID NO:26:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: protein ( x i ) SEQUENCE DESCRIPTION: SEQ ID NO:26:

```
Pro Phe Gly Ala Gly Arg Arg Ile Cys Pro
  1           5                  10
```

( 2 ) INFORMATION FOR SEQ ID NO:27:

( i ) SEQUENCE CHARACTERISTICS:
        ( A ) LENGTH: 733 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( A ) NAME/KEY: CDS
        ( B ) LOCATION: 1..402

( x i ) SEQUENCE DESCRIPTION: SEQ ID NO:27:

```
TTT AGT TCA ATT CGG AAT GAT GAG ATT TCG AGT CTC ATT TCA TCA ATT         48
Phe Ser Ser Ile Arg Asn Asp Glu Ile Ser Ser Leu Ile Ser Ser Ile
  1           5                  10                  15

CAT TCC ATG AAC GGT TCT GTT GTC AAC ATG ACA CAA AAG ATT CTT TGT         96
His Ser Met Asn Gly Ser Val Val Asn Met Thr Gln Lys Ile Leu Cys
             20                  25                  30

TTT ACA AAC TCT GTG ACT TGT AGA ACA GCT TTC GGG AAA GTA TAC AAA        144
Phe Thr Asn Ser Val Thr Cys Arg Thr Ala Phe Gly Lys Val Tyr Lys
         35                  40                  45

AAT CAA AAT GAA TTG ATA AAC TTG ATG AGG GAA GTA CTG GAA TTA GTA        192
Asn Gln Asn Glu Leu Ile Asn Leu Met Arg Glu Val Leu Glu Leu Val
     50                  55                  60

GGA GGA TTT GAT TTT GAA AAT TCT CCG GTT GAG TTT ATT GGA AAT CAC        240
Gly Gly Phe Asp Phe Glu Asn Ser Pro Val Glu Phe Ile Gly Asn His
 65                  70                  75                  80

TTT GAG CTT GTT CCG TTT GGT GCA GGA AAA AGG ATT TGT CCA GGA ATG        288
Phe Glu Leu Val Pro Phe Gly Ala Gly Lys Arg Ile Cys Pro Gly Met
                 85                  90                  95

CAA TTT GGT TTA GCT AAT ATT AGA CAT CCT TTG GCT CGA TTC CTC TAC        336
Gln Phe Gly Leu Ala Asn Ile Arg His Pro Leu Ala Arg Phe Leu Tyr
            100                 105                 110

CAT TTT AAC TGG GCG CTT CCA TAT GAA ACT AAT CCT GAA GAT TTA GAT        384
His Phe Asn Trp Ala Leu Pro Tyr Glu Thr Asn Pro Glu Asp Leu Asp
        115                 120                 125

AGT CTG AAA AAT ATG GAT TAAGTGCAGC AAAAGAGAAA GATCTATACT               432
Ser Leu Lys Asn Met Asp
    130
```

```
TAATTGCCGT AGATCACAAA GAAGGTGATA TATAAATTCT GATGTTCTGC TTTAAATGGT       492

GAAAGTCATA CTCTACACAA TGCTTCATCT CCTTAATTTG AGTTTGGTGT ACATTTGTGT       552

CTCCCTTTTA GCTTTGAATT TCACCTTGAA AAATGATCAC ATTTTCTTTT TCTGTTACTC       612

CAATTAAGAT ATATGTTGTG GTTGGTCAAT TATGCCATAT TTATCAAAAG ATCAAATCAA       672

TTCCCTCGTT GATAAGTATA GATTATAAAA CTGATTAATG AATCAAAAAA AAAAAAAAA       732

A                                                                      733
```

( 2 ) INFORMATION FOR SEQ ID NO:28:

( i ) SEQUENCE CHARACTERISTICS:
        ( A ) LENGTH: 134 amino acids
        ( B ) TYPE: amino acid
        ( D ) TOPOLOGY: linear ( i i ) MOLECULE TYPE: protein ( x i ) SEQUENCE DESCRIPTION: SEQ ID NO:28:

```
Phe  Ser  Ser  Ile  Arg  Asn  Asp  Glu  Ile  Ser  Ser  Leu  Ile  Ser  Ser  Ile
 1              5                        10                       15

His  Ser  Met  Asn  Gly  Ser  Val  Val  Asn  Met  Thr  Gln  Lys  Ile  Leu  Cys
           20                        25                       30

Phe  Thr  Asn  Ser  Val  Thr  Cys  Arg  Thr  Ala  Phe  Gly  Lys  Val  Tyr  Lys
                35                        40                       45

Asn  Gln  Asn  Glu  Leu  Ile  Asn  Leu  Met  Arg  Glu  Val  Leu  Glu  Leu  Val
      50                        55                       60

Gly  Gly  Phe  Asp  Phe  Glu  Asn  Ser  Pro  Val  Glu  Phe  Ile  Gly  Asn  His
 65                        70                        75                      80

Phe  Glu  Leu  Val  Pro  Phe  Gly  Ala  Gly  Lys  Arg  Ile  Cys  Pro  Gly  Met
                     85                        90                       95

Gln  Phe  Gly  Leu  Ala  Asn  Ile  Arg  His  Pro  Leu  Ala  Arg  Phe  Leu  Tyr
               100                       105                      110

His  Phe  Asn  Trp  Ala  Leu  Pro  Tyr  Glu  Thr  Asn  Pro  Glu  Asp  Leu  Asp
          115                       120                      125

Ser  Leu  Lys  Asn  Met  Asp
          130
```

( 2 ) INFORMATION FOR SEQ ID NO:29:

( i ) SEQUENCE CHARACTERISTICS:
        ( A ) LENGTH: 1665 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( A ) NAME/KEY: CDS
        ( B ) LOCATION: 3..1432

( x i ) SEQUENCE DESCRIPTION: SEQ ID NO:29:

```
TG  CAA  TTT  TTC  AAC  TTG  GTT  TCC  TTT  CTC  CTT  ATT  GTA  TTT  TCC  CTC         47
    Gln  Phe  Phe  Asn  Leu  Val  Ser  Phe  Leu  Leu  Ile  Val  Phe  Ser  Leu
     1              5                        10                       15

ATT  TCA  TTA  AGA  AAA  TGG  AAG  AAA  TCC  AAT  TGT  CAA  ACC  AAA  AAA  TTG        95
Ile  Ser  Leu  Arg  Lys  Trp  Lys  Lys  Ser  Asn  Cys  Gln  Thr  Lys  Lys  Leu
                20                        25                       30

CCT  CCA  GGC  CCA  TGG  AAA  GTA  CCT  TTT  CTT  GGA  AGC  TTG  CTT  CAT  ATG       143
Pro  Pro  Gly  Pro  Trp  Lys  Val  Pro  Phe  Leu  Gly  Ser  Leu  Leu  His  Met
                35                        40                       45
```

| | | | | | | | | | | | | | | | | |
|---|---|---|---|---|---|---|---|---|---|---|---|---|---|---|---|---|
| GTA | GGT | GGA | CTT | CCA | CAC | CAT | GTC | CTT | AGA | GAT | TTA | GCC | AAA | AAA | TAT | 191 |
| Val | Gly | Gly | Leu | Pro | His | His | Val | Leu | Arg | Asp | Leu | Ala | Lys | Lys | Tyr | |
| | | 50 | | | | 55 | | | | | 60 | | | | | |
| GGA | CCA | ATT | ATG | CAC | CTT | CAA | CTA | GGT | AAA | ATT | TCT | GCC | GTT | GTA | GTT | 239 |
| Gly | Pro | Ile | Met | His | Leu | Gln | Leu | Gly | Lys | Ile | Ser | Ala | Val | Val | Val | |
| | 65 | | | | | 70 | | | | | 75 | | | | | |
| ACT | TCT | CCT | GAG | ATG | GCA | AGA | AAA | GTA | CTA | AAA | ACT | CAT | GAC | CTT | GCA | 287 |
| Thr | Ser | Pro | Glu | Met | Ala | Arg | Lys | Val | Leu | Lys | Thr | His | Asp | Leu | Ala | |
| 80 | | | | | 85 | | | | | 90 | | | | | 95 | |
| TTT | GCA | TAT | AGG | CCT | AAA | CTT | CTA | GGC | ATT | GAG | ATT | GTC | TGC | TAT | AAT | 335 |
| Phe | Ala | Tyr | Arg | Pro | Lys | Leu | Leu | Gly | Ile | Glu | Ile | Val | Cys | Tyr | Asn | |
| | | | | 100 | | | | | 105 | | | | | 110 | | |
| AGT | TCA | GAC | ATT | GCC | TTT | TCC | CCG | TAT | GGT | GAT | TAC | TGG | AGG | CAA | ATG | 383 |
| Ser | Ser | Asp | Ile | Ala | Phe | Ser | Pro | Tyr | Gly | Asp | Tyr | Trp | Arg | Gln | Met | |
| | | | 115 | | | | | 120 | | | | | 125 | | | |
| CGT | AAA | ATT | TGT | GTA | TTG | GAA | GTG | CTT | AGT | GCC | AAA | AAT | GTC | CGG | TCA | 431 |
| Arg | Lys | Ile | Cys | Val | Leu | Glu | Val | Leu | Ser | Ala | Lys | Asn | Val | Arg | Ser | |
| | | 130 | | | | | 135 | | | | | 140 | | | | |
| TTT | AAC | TCG | ATT | AGA | CGA | GAT | GAA | ATA | CTT | CTT | ATG | ATC | GAT | TTT | TTG | 479 |
| Phe | Asn | Ser | Ile | Arg | Arg | Asp | Glu | Ile | Leu | Leu | Met | Ile | Asp | Phe | Leu | |
| | 145 | | | | | 150 | | | | | 155 | | | | | |
| CGA | TCA | TCT | TCT | GGT | AAG | CCA | GTT | AAT | ATA | ACA | GAA | AGG | ATC | TTT | TCA | 527 |
| Arg | Ser | Ser | Ser | Gly | Lys | Pro | Val | Asn | Ile | Thr | Glu | Arg | Ile | Phe | Ser | |
| 160 | | | | | 165 | | | | | 170 | | | | | 175 | |
| TTC | ACA | AGC | TCT | ATG | ATT | TGT | AGA | TCA | GTA | TTT | GGG | AAA | AGA | ATA | AAG | 575 |
| Phe | Thr | Ser | Ser | Met | Ile | Cys | Arg | Ser | Val | Phe | Gly | Lys | Arg | Ile | Lys | |
| | | | | 180 | | | | | 185 | | | | | 190 | | |
| GAG | AAA | GAC | GAA | TGT | ATA | CGA | CAT | GTG | AAA | AAA | ATG | ACA | GGC | TTA | ATA | 623 |
| Glu | Lys | Asp | Glu | Cys | Ile | Arg | His | Val | Lys | Lys | Met | Thr | Gly | Leu | Ile | |
| | | | 195 | | | | | 200 | | | | | 205 | | | |
| GAT | GGG | TTC | GAT | GTG | GCT | GAC | ATA | TTC | CCT | TCG | TTG | AGG | TTT | CTT | CAT | 671 |
| Asp | Gly | Phe | Asp | Val | Ala | Asp | Ile | Phe | Pro | Ser | Leu | Arg | Phe | Leu | His | |
| | | 210 | | | | | 215 | | | | | 220 | | | | |
| GTA | CTA | ATC | GGT | ATG | AAG | GGT | AAA | ATT | ATG | GAT | GTT | CAT | CGT | AAG | GTA | 719 |
| Val | Leu | Ile | Gly | Met | Lys | Gly | Lys | Ile | Met | Asp | Val | His | Arg | Lys | Val | |
| | 225 | | | | | 230 | | | | | 235 | | | | | |
| GAT | GCT | ATT | GTT | GAG | GAA | GTC | ATG | AAT | GAG | CAC | AAA | GAA | ACT | CTT | CGA | 767 |
| Asp | Ala | Ile | Val | Glu | Glu | Val | Met | Asn | Glu | His | Lys | Glu | Thr | Leu | Arg | |
| 240 | | | | | 245 | | | | | 250 | | | | | 255 | |
| ACT | GGC | AAG | ACC | AAT | GGT | GAA | GTG | GGA | GGA | GAA | GAT | TTA | ATT | GAT | GTA | 815 |
| Thr | Gly | Lys | Thr | Asn | Gly | Glu | Val | Gly | Gly | Glu | Asp | Leu | Ile | Asp | Val | |
| | | | | 260 | | | | | 265 | | | | | 270 | | |
| TTG | CTA | AGA | CTT | AAG | GAA | GAG | GGA | GAC | CTT | CAA | CTT | CCA | ATC | ACA | AAT | 863 |
| Leu | Leu | Arg | Leu | Lys | Glu | Glu | Gly | Asp | Leu | Gln | Leu | Pro | Ile | Thr | Asn | |
| | | | 275 | | | | | 280 | | | | | 285 | | | |
| GAC | AAC | ATC | AAA | GCC | ATT | TTT | AAT | GAC | ATG | TTT | GCT | GCG | GGA | ACA | GAA | 911 |
| Asp | Asn | Ile | Lys | Ala | Ile | Phe | Asn | Asp | Met | Phe | Ala | Ala | Gly | Thr | Glu | |
| | | 290 | | | | | 295 | | | | | 300 | | | | |
| ACT | TCA | TCA | ACA | ACA | ATT | AAC | TGG | GCC | ATG | GTA | GAA | CTG | ATG | AAA | AAT | 959 |
| Thr | Ser | Ser | Thr | Thr | Ile | Asn | Trp | Ala | Met | Val | Glu | Leu | Met | Lys | Asn | |
| | 305 | | | | | 310 | | | | | 315 | | | | | |
| CCA | AGT | GTA | TTC | GCG | AAA | GCT | CAA | GCA | GAG | GTA | AGA | GAA | GTC | TTC | AAA | 1007 |
| Pro | Ser | Val | Phe | Ala | Lys | Ala | Gln | Ala | Glu | Val | Arg | Glu | Val | Phe | Lys | |
| 320 | | | | | 325 | | | | | 330 | | | | | 335 | |
| GGG | AAA | GAA | ACT | TTC | GAT | GAA | GAT | GAT | ATC | GAG | GAG | CTG | AAT | TAC | CTT | 1055 |
| Gly | Lys | Glu | Thr | Phe | Asp | Glu | Asp | Asp | Ile | Glu | Glu | Leu | Asn | Tyr | Leu | |
| | | | | 340 | | | | | 345 | | | | | 350 | | |
| AAG | TTA | GTC | ATT | AGA | GAA | ACT | TTA | AGA | CTC | CAC | CCT | CCA | CTT | CCA | CTT | 1103 |
| Lys | Leu | Val | Ile | Arg | Glu | Thr | Leu | Arg | Leu | His | Pro | Pro | Leu | Pro | Leu | |
| | | | 355 | | | | | 360 | | | | | 365 | | | |

-continued

| | | | | | | | | | | | | | | | | |
|---|---|---|---|---|---|---|---|---|---|---|---|---|---|---|---|---|
| TTG | CTT | CCA | AGA | GAA | TGT | CGG | AGA | GAA | ACA | GAA | ATA | AAT | GGC | TAC | ACT | 1151 |
| Leu | Leu | Pro | Arg | Glu | Cys | Arg | Arg | Glu | Thr | Glu | Ile | Asn | Gly | Tyr | Thr | |
| | | 370 | | | | | 375 | | | | | 380 | | | | |
| ATT | CCT | TTA | AAT | ACC | AAA | GTC | ATA | GTT | AAT | GTT | TGG | GCT | ATT | GGA | AGA | 1199 |
| Ile | Pro | Leu | Asn | Thr | Lys | Val | Ile | Val | Asn | Val | Trp | Ala | Ile | Gly | Arg | |
| | | 385 | | | | | 390 | | | | | 395 | | | | |
| GAT | CCA | AAA | TAT | TGG | GAT | GAT | GCA | GAA | AGC | TTT | AAG | CCT | GAG | AGA | TTT | 1247 |
| Asp | Pro | Lys | Tyr | Trp | Asp | Asp | Ala | Glu | Ser | Phe | Lys | Pro | Glu | Arg | Phe | |
| 400 | | | | | 405 | | | | | 410 | | | | | 415 | |
| GAA | CAT | AAC | TCT | TTG | AAT | TTT | GCT | GGC | AAT | AAT | TTT | GAA | TAT | CTT | CCT | 1295 |
| Glu | His | Asn | Ser | Leu | Asn | Phe | Ala | Gly | Asn | Asn | Phe | Glu | Tyr | Leu | Pro | |
| | | | | 420 | | | | | 425 | | | | | 430 | | |
| TTT | GGT | AGT | GGA | AGG | AGG | ATT | TGC | CCC | GGA | ATA | TCA | TTT | GGT | TTA | GCT | 1343 |
| Phe | Gly | Ser | Gly | Arg | Arg | Ile | Cys | Pro | Gly | Ile | Ser | Phe | Gly | Leu | Ala | |
| | | | 435 | | | | | 440 | | | | | 445 | | | |
| AAT | GTT | TAT | CAT | CCA | TTG | GCT | CAA | TTG | TTG | TAT | CAT | TTC | GAT | TGG | AGA | 1391 |
| Asn | Val | Tyr | His | Pro | Leu | Ala | Gln | Leu | Leu | Tyr | His | Phe | Asp | Trp | Arg | |
| | | 450 | | | | | 455 | | | | | 460 | | | | |
| CTT | CCT | ACT | GGG | GTC | GAC | CCA | AAT | GAC | TTT | GAA | TTG | ACT | AG | TTAGCTGGAG | | 1442 |
| Leu | Pro | Thr | Gly | Val | Asp | Pro | Asn | Asp | Phe | Glu | Leu | Thr | | | | |
| | | 465 | | | | 470 | | | | | 475 | | | | | |

TAACTACTGG TAGGAAAAGA GACCTTTACT TGATTTTCAC TCCTTATTCA CCTTCTCTAA 1502

AGTGATTAAA TGGGCAAATT TTAATTTGAA ATAATACTTT TCTTGTTTA CATTTCTCTC 1562

CCATTGTTGT ATTTCATTTA CCTATTGTTG TACTTCTTTC TTTTGTTGAT GTCTTAGGTT 1622

TTACCTATTT CTATGCATTT GTATTTAAAA AAAAAAAAAA AAA 1665

( 2 ) INFORMATION FOR SEQ ID NO:30:

( i ) SEQUENCE CHARACTERISTICS:
        ( A ) LENGTH: 476 amino acids
        ( B ) TYPE: amino acid
        ( D ) TOPOLOGY: linear ( i i ) MOLECULE TYPE: protein ( x i ) SEQUENCE DESCRIPTION: SEQ ID NO:30:

| | | | | | | | | | | | | | | | |
|---|---|---|---|---|---|---|---|---|---|---|---|---|---|---|---|
| Gln | Phe | Phe | Asn | Leu | Val | Ser | Phe | Leu | Leu | Ile | Val | Phe | Ser | Leu | Ile |
| 1 | | | | 5 | | | | | 10 | | | | | 15 | |
| Ser | Leu | Arg | Lys | Trp | Lys | Lys | Ser | Asn | Cys | Gln | Thr | Lys | Lys | Leu | Pro |
| | | | 20 | | | | | 25 | | | | | 30 | | |
| Pro | Gly | Pro | Trp | Lys | Val | Pro | Phe | Leu | Gly | Ser | Leu | Leu | His | Met | Val |
| | | | 35 | | | | | 40 | | | | | 45 | | |
| Gly | Gly | Leu | Pro | His | His | Val | Leu | Arg | Asp | Leu | Ala | Lys | Lys | Tyr | Gly |
| | 50 | | | | | 55 | | | | | 60 | | | | |
| Pro | Ile | Met | His | Leu | Gln | Leu | Gly | Lys | Ile | Ser | Ala | Val | Val | Val | Thr |
| 65 | | | | | 70 | | | | | 75 | | | | | 80 |
| Ser | Pro | Glu | Met | Ala | Arg | Lys | Val | Leu | Lys | Thr | His | Asp | Leu | Ala | Phe |
| | | | | 85 | | | | | 90 | | | | | 95 | |
| Ala | Tyr | Arg | Pro | Lys | Leu | Leu | Gly | Ile | Glu | Ile | Val | Cys | Tyr | Asn | Ser |
| | | | 100 | | | | | 105 | | | | | 110 | | |
| Ser | Asp | Ile | Ala | Phe | Ser | Pro | Tyr | Gly | Asp | Tyr | Trp | Arg | Gln | Met | Arg |
| | | | 115 | | | | | 120 | | | | | 125 | | |
| Lys | Ile | Cys | Val | Leu | Glu | Val | Leu | Ser | Ala | Lys | Asn | Val | Arg | Ser | Phe |
| | | 130 | | | | | 135 | | | | | 140 | | | |
| Asn | Ser | Ile | Arg | Arg | Asp | Glu | Ile | Leu | Leu | Met | Ile | Asp | Phe | Leu | Arg |
| 145 | | | | | 150 | | | | | 155 | | | | | 160 |
| Ser | Ser | Ser | Gly | Lys | Pro | Val | Asn | Ile | Thr | Glu | Arg | Ile | Phe | Ser | Phe |
| | | | | 165 | | | | | 170 | | | | | 175 | |

| Thr | Ser | Ser | Met | Ile | Cys | Arg | Ser | Val | Phe | Gly | Lys | Arg | Ile | Lys | Glu |
| | | | 180 | | | | 185 | | | | | | 190 | | |

| Lys | Asp | Glu | Cys | Ile | Arg | His | Val | Lys | Lys | Met | Thr | Gly | Leu | Ile | Asp |
| | | 195 | | | | | 200 | | | | | 205 | | | |

| Gly | Phe | Asp | Val | Ala | Asp | Ile | Phe | Pro | Ser | Leu | Arg | Phe | Leu | His | Val |
| | 210 | | | | 215 | | | | | | 220 | | | | |

| Leu | Ile | Gly | Met | Lys | Gly | Lys | Ile | Met | Asp | Val | His | Arg | Lys | Val | Asp |
| 225 | | | | | 230 | | | | | 235 | | | | | 240 |

| Ala | Ile | Val | Glu | Glu | Val | Met | Asn | Glu | His | Lys | Glu | Thr | Leu | Arg | Thr |
| | | | | 245 | | | | | 250 | | | | | 255 | |

| Gly | Lys | Thr | Asn | Gly | Glu | Val | Gly | Gly | Glu | Asp | Leu | Ile | Asp | Val | Leu |
| | | | 260 | | | | | 265 | | | | | 270 | | |

| Leu | Arg | Leu | Lys | Glu | Glu | Gly | Asp | Leu | Gln | Leu | Pro | Ile | Thr | Asn | Asp |
| | | | 275 | | | | 280 | | | | | 285 | | | |

| Asn | Ile | Lys | Ala | Ile | Phe | Asn | Asp | Met | Phe | Ala | Ala | Gly | Thr | Glu | Thr |
| | | 290 | | | | | 295 | | | | | 300 | | | |

| Ser | Ser | Thr | Thr | Ile | Asn | Trp | Ala | Met | Val | Glu | Leu | Met | Lys | Asn | Pro |
| 305 | | | | | 310 | | | | | 315 | | | | | 320 |

| Ser | Val | Phe | Ala | Lys | Ala | Gln | Ala | Glu | Val | Arg | Glu | Val | Phe | Lys | Gly |
| | | | | 325 | | | | | 330 | | | | | 335 | |

| Lys | Glu | Thr | Phe | Asp | Glu | Asp | Asp | Ile | Glu | Glu | Leu | Asn | Tyr | Leu | Lys |
| | | | 340 | | | | | 345 | | | | | 350 | | |

| Leu | Val | Ile | Arg | Glu | Thr | Leu | Arg | Leu | His | Pro | Pro | Leu | Pro | Leu | Leu |
| | | | 355 | | | | 360 | | | | | 365 | | | |

| Leu | Pro | Arg | Glu | Cys | Arg | Arg | Glu | Thr | Glu | Ile | Asn | Gly | Tyr | Thr | Ile |
| | 370 | | | | | 375 | | | | | 380 | | | | |

| Pro | Leu | Asn | Thr | Lys | Val | Ile | Val | Asn | Val | Trp | Ala | Ile | Gly | Arg | Asp |
| 385 | | | | | 390 | | | | | 395 | | | | | 400 |

| Pro | Lys | Tyr | Trp | Asp | Asp | Ala | Glu | Ser | Phe | Lys | Pro | Glu | Arg | Phe | Glu |
| | | | | 405 | | | | | 410 | | | | | 415 | |

| His | Asn | Ser | Leu | Asn | Phe | Ala | Gly | Asn | Asn | Phe | Glu | Tyr | Leu | Pro | Phe |
| | | | 420 | | | | | 425 | | | | | 430 | | |

| Gly | Ser | Gly | Arg | Arg | Ile | Cys | Pro | Gly | Ile | Ser | Phe | Gly | Leu | Ala | Asn |
| | | 435 | | | | | 440 | | | | | 445 | | | |

| Val | Tyr | His | Pro | Leu | Ala | Gln | Leu | Leu | Tyr | His | Phe | Asp | Trp | Arg | Leu |
| | 450 | | | | | 455 | | | | | 460 | | | | |

| Pro | Thr | Gly | Val | Asp | Pro | Asn | Asp | Phe | Glu | Leu | Thr |
| 465 | | | | | 470 | | | | | 475 | |

( 2 ) INFORMATION FOR SEQ ID NO:31:

( i ) SEQUENCE CHARACTERISTICS:
        ( A ) LENGTH: 547 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( A ) NAME/KEY: CDS
        ( B ) LOCATION: 1..514

( x i ) SEQUENCE DESCRIPTION: SEQ ID NO:31:

| GGG | ATG | ATG | AAG | CAA | GGA | GAT | TTC | TTG | GAT | GTA | CTT | CTT | GAT | CAA | TGT | 48 |
| Gly | Met | Met | Lys | Gln | Gly | Asp | Phe | Leu | Asp | Val | Leu | Leu | Asp | Gln | Cys | |
| 1 | | | | 5 | | | | | 10 | | | | | 15 | | |

| GAT | GAA | GAA | GGG | TCT | GGA | TTT | GAT | CGC | CAA | ACT | ATC | AAG | CCT | CTC | ATC | 96 |

-continued

```
Asp Glu Glu Gly Ser Gly Phe Asp Arg Gln Thr Ile Lys Pro Leu Ile
         20                  25                  30

CTG GAT TTA TTC ATT GCT GGA AGT GAT ACA TCT GCC ATA ACA ACA GAA        144
Leu Asp Leu Phe Ile Ala Gly Ser Asp Thr Ser Ala Ile Thr Thr Glu
         35                  40                  45

TGG GCA ATG GCA GAA CTA CTT CGA AAA CCT CAA GAA TTT GTG AAT GCA        192
Trp Ala Met Ala Glu Leu Leu Arg Lys Pro Gln Glu Phe Val Asn Ala
     50                  55                  60

TGG GCA ATT GGA AGA GAT CCA AAA TAC TGG GAA AAA CCA CTG GAG TTT        240
Trp Ala Ile Gly Arg Asp Pro Lys Tyr Trp Glu Lys Pro Leu Glu Phe
 65                  70                  75                  80

ATG CCT GAA AGA TTC TTG AAG TGT AGT TTG GAT TAC AAA GGT AGG GNN        288
Met Pro Glu Arg Phe Leu Lys Cys Ser Leu Asp Tyr Lys Gly Arg Xaa
                 85                  90                  95

TTT GAG TAT ATA CCA TTT GGC GCA GGT CGA AGA ATT TGT CCT GGA ATG        336
Phe Glu Tyr Ile Pro Phe Gly Ala Gly Arg Arg Ile Cys Pro Gly Met
             100                 105                 110

CCA CAT TGC AAT AAG GAT GGT GAA TTT GAT GCT GGC TTC GAT TAT TCA        384
Pro His Cys Asn Lys Asp Gly Glu Phe Asp Ala Gly Phe Asp Tyr Ser
             115                 120                 125

CCA TTT AGT TGG GAA TTA CCT NAA GGA ATG GCA CCA AAG NAT TTG AAC        432
Pro Phe Ser Trp Glu Leu Pro Xaa Gly Met Ala Pro Lys Xaa Leu Asn
         130                 135                 140

ATG GAG GAA CAG TTT GGA GTT ACC TTG AGG AAG GCT ATT CCC CTT ATT        480
Met Glu Glu Gln Phe Gly Val Thr Leu Arg Lys Ala Ile Pro Leu Ile
145                 150                 155                 160

GCC ATT CCC AGT ATG GAA GAA AAG GTC ATA TTT T AGCCCAAAAG               524
Ala Ile Pro Ser Met Glu Glu Lys Val Ile Phe
                 165                 170

CTATGCATTT TGTGTGTATG TTT                                              547
```

(2) INFORMATION FOR SEQ ID NO:32:

(i) SEQUENCE CHARACTERISTICS:
      (A) LENGTH: 171 amino acids
      (B) TYPE: amino acid
      (D) TOPOLOGY: linear (ii) MOLECULE TYPE: protein (xi) SEQUENCE DESCRIPTION: SEQ ID NO:32:

```
Gly Met Met Lys Gln Gly Asp Phe Leu Asp Val Leu Leu Asp Gln Cys
 1               5                  10                  15

Asp Glu Glu Gly Ser Gly Phe Asp Arg Gln Thr Ile Lys Pro Leu Ile
         20                  25                  30

Leu Asp Leu Phe Ile Ala Gly Ser Asp Thr Ser Ala Ile Thr Thr Glu
         35                  40                  45

Trp Ala Met Ala Glu Leu Leu Arg Lys Pro Gln Glu Phe Val Asn Ala
     50                  55                  60

Trp Ala Ile Gly Arg Asp Pro Lys Tyr Trp Glu Lys Pro Leu Glu Phe
 65                  70                  75                  80

Met Pro Glu Arg Phe Leu Lys Cys Ser Leu Asp Tyr Lys Gly Arg Xaa
                 85                  90                  95

Phe Glu Tyr Ile Pro Phe Gly Ala Gly Arg Arg Ile Cys Pro Gly Met
             100                 105                 110

Pro His Cys Asn Lys Asp Gly Glu Phe Asp Ala Gly Phe Asp Tyr Ser
             115                 120                 125

Pro Phe Ser Trp Glu Leu Pro Xaa Gly Met Ala Pro Lys Xaa Leu Asn
         130                 135                 140
```

```
Met  Glu  Gln  Phe  Gly  Val  Thr  Leu  Arg  Lys  Ala  Ile  Pro  Leu  Ile
145            150                 155                 160

Ala  Ile  Pro  Ser  Met  Glu  Glu  Lys  Val  Ile  Phe
               165                 170
```

(2) INFORMATION FOR SEQ ID NO:33:

(i) SEQUENCE CHARACTERISTICS:
        (A) LENGTH: 618 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: CDS
        (B) LOCATION: 1..336

(xi) SEQUENCE DESCRIPTION: SEQ ID NO:33:

```
AAA  CAG  ATC  AAT  GCA  TTG  CTT  GTG  GAA  ATA  TTT  GGA  GCT  GGT  ACA  GAA     48
Lys  Gln  Ile  Asn  Ala  Leu  Leu  Val  Glu  Ile  Phe  Gly  Ala  Gly  Thr  Glu
 1                    5                      10                      15

TCT  ACA  ACT  GCT  ACA  AGC  CAA  TGG  ATG  CTT  GTA  GAA  CTC  CTT  AGA  AAT     96
Ser  Thr  Thr  Ala  Thr  Ser  Gln  Trp  Met  Leu  Val  Glu  Leu  Leu  Arg  Asn
                20                      25                      30

CGA  CAA  GCC  TTG  CCC  AAA  GAC  ACT  CAA  GTT  ATG  GTA  AAC  GAG  TGG  GCG    144
Arg  Gln  Ala  Leu  Pro  Lys  Asp  Thr  Gln  Val  Met  Val  Asn  Glu  Trp  Ala
           35                      40                      45

ATT  GCG  TAT  GAT  CCT  AAG  ATT  TGG  GGC  AGC  TTC  AAA  CCC  GAA  AGG  TTT    192
Ile  Ala  Tyr  Asp  Pro  Lys  Ile  Trp  Gly  Ser  Phe  Lys  Pro  Glu  Arg  Phe
      50                      55                      60

ATC  GAT  TCA  AAA  ATA  GAT  CCT  TTG  GAC  CAC  AAA  GGG  CAA  AAT  TTT  GAA    240
Ile  Asp  Ser  Lys  Ile  Asp  Pro  Leu  Asp  His  Lys  Gly  Gln  Asn  Phe  Glu
 65                      70                      75                      80

TAT  TTT  CCT  TTT  GGT  TCT  GGA  AGG  AGA  ATT  TGT  GCT  GGA  GAA  CCT  TTG    288
Tyr  Phe  Pro  Phe  Gly  Ser  Gly  Arg  Arg  Ile  Cys  Ala  Gly  Glu  Pro  Leu
                     85                      90                      95

GCT  TCT  AGG  GTT  ATT  CCC  TTA  GCT  GTT  GCT  TCT  ATG  ATC  CAT  AAG  TTT    336
Ala  Ser  Arg  Val  Ile  Pro  Leu  Ala  Val  Ala  Ser  Met  Ile  His  Lys  Phe
               100                     105                     110

GATATCACTA  TGTTAGAAGA  TCCACTCTCA  TCATTCCTAA  GTTGAAGAA   GTGAGGAAAT    396

TAAAAGAAGC  AGAAGATATG  TTACTATAAA  AACTCGTTAT  ATATATATAT  ATTGCTGTAT    456

CTATATATGT  GTGAATGATC  TGCTGCTCAT  GTTGTGTTTT  GTTGTTTGTG  TACTATAGGT    516

CATACCTAAG  TTGATGAAAT  GTCTCTGAGA  ATATATACTC  CTTATATAAT  AGGAGTAATT    576

TACCGATAAT  TAATATTCCT  GCGACAAAAA  AAAAAAAAA   AA                       618
```

(2) INFORMATION FOR SEQ ID NO:34:

(i) SEQUENCE CHARACTERISTICS:
        (A) LENGTH: 112 amino acids
        (B) TYPE: amino acid
        (D) TOPOLOGY: linear (ii) MOLECULE TYPE: protein (xi) SEQUENCE DESCRIPTION: SEQ ID NO:34:

```
Lys  Gln  Ile  Asn  Ala  Leu  Leu  Val  Glu  Ile  Phe  Gly  Ala  Gly  Thr  Glu
 1                    5                      10                      15

Ser  Thr  Thr  Ala  Thr  Ser  Gln  Trp  Met  Leu  Val  Glu  Leu  Leu  Arg  Asn
                20                      25                      30

Arg  Gln  Ala  Leu  Pro  Lys  Asp  Thr  Gln  Val  Met  Val  Asn  Glu  Trp  Ala
```

```
            35                          40                          45

Ile  Ala  Tyr  Asp  Pro  Lys  Ile  Trp  Gly  Ser  Phe  Lys  Pro  Glu  Arg  Phe
          50                          55                          60

Ile  Asp  Ser  Lys  Ile  Asp  Pro  Leu  Asp  His  Lys  Gly  Gln  Asn  Phe  Glu
65                          70                          75                          80

Tyr  Phe  Pro  Phe  Gly  Ser  Gly  Arg  Arg  Ile  Cys  Ala  Gly  Glu  Pro  Leu
                    85                          90                          95

Ala  Ser  Arg  Val  Ile  Pro  Leu  Ala  Val  Ala  Ser  Met  Ile  His  Lys  Phe
               100                         105                         110
```

( 2 ) INFORMATION FOR SEQ ID NO:35:

( i ) SEQUENCE CHARACTERISTICS:
        ( A ) LENGTH: 203 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( A ) NAME/KEY: CDS
        ( B ) LOCATION: 3..203

( x i ) SEQUENCE DESCRIPTION: SEQ ID NO:35:

```
CT  CGA  GAA  TCA  ATG  GAA  GAT  GTA  AGA  TTA  CTA  GGC  TAT  CAC  ATA  CCT      47
    Arg  Glu  Ser  Met  Glu  Asp  Val  Arg  Leu  Leu  Gly  Tyr  His  Ile  Pro
     1                   5                        10                        15

GCT  AAA  ACG  AGA  CTC  TTT  ATC  AAT  GCT  TGG  ACA  ATG  GGG  AGA  GAC  CCA      95
Ala  Lys  Thr  Arg  Leu  Phe  Ile  Asn  Ala  Trp  Thr  Met  Gly  Arg  Asp  Pro
                    20                        25                        30

CTA  ACA  TGG  GAA  AAT  CCA  GAA  GAG  TAT  CAG  CCA  GAG  AGA  TTC  TTG  AAT     143
Leu  Thr  Trp  Glu  Asn  Pro  Glu  Glu  Tyr  Gln  Pro  Glu  Arg  Phe  Leu  Asn
               35                        40                        45

AGA  GAT  ACT  GAT  GTC  AAA  GGA  GTA  AAC  TTT  GAG  TTC  ATT  CCC  TTT  GGC     191
Arg  Asp  Thr  Asp  Val  Lys  Gly  Val  Asn  Phe  Glu  Phe  Ile  Pro  Phe  Gly
          50                        55                        60

GCC  GGC  AGA  AGC                                                                 203
Ala  Gly  Arg  Ser
          65
```

( 2 ) INFORMATION FOR SEQ ID NO:36:

( i ) SEQUENCE CHARACTERISTICS:
        ( A ) LENGTH: 67 amino acids
        ( B ) TYPE: amino acid
        ( D ) TOPOLOGY: linear ( i i ) MOLECULE TYPE: protein ( x i ) SEQUENCE DESCRIPTION: SEQ ID NO:36:

```
Arg  Glu  Ser  Met  Glu  Asp  Val  Arg  Leu  Leu  Gly  Tyr  His  Ile  Pro  Ala
 1                   5                        10                        15

Lys  Thr  Arg  Leu  Phe  Ile  Asn  Ala  Trp  Thr  Met  Gly  Arg  Asp  Pro  Leu
                    20                        25                        30

Thr  Trp  Glu  Asn  Pro  Glu  Glu  Tyr  Gln  Pro  Glu  Arg  Phe  Leu  Asn  Arg
               35                        40                        45

Asp  Thr  Asp  Val  Lys  Gly  Val  Asn  Phe  Glu  Phe  Ile  Pro  Phe  Gly  Ala
          50                        55                        60

Gly  Arg  Ser
 65
```

( 2 ) INFORMATION FOR SEQ ID NO:37:

( i ) SEQUENCE CHARACTERISTICS:
   ( A ) LENGTH: 1812 base pairs
   ( B ) TYPE: nucleic acid
   ( C ) STRANDEDNESS: single
   ( D ) TOPOLOGY: linear ( i i ) MOLECULE TYPE: DNA ( i x ) FEATURE:
   ( A ) NAME/KEY: CDS
   ( B ) LOCATION: 126..1643

( x i ) SEQUENCE DESCRIPTION: SEQ ID NO:37:

```
CTTTCTACTA GCTACTTCGT TATATATATG TAAAATTGTG ACTTTGAAAA TCATTTAAAT      60

TATCATAAGG TTCATTTTAT CTTGATCAAA ATATTTACTT CGGCCATATA CGTTTTCCTT     120

TAGTC ATG ATG CTA CTT ACT GAG CTT GGT GCA GCA ACT TCA ATC TTT        167
      Met Met Leu Leu Thr Glu Leu Gly Ala Ala Thr Ser Ile Phe
        1           5                  10

CTA ATA GCA CAC ATA ATC ATT TCA ACT CTT ATT TCA AAA ACT ACC GGC      215
Leu Ile Ala His Ile Ile Ile Ser Thr Leu Ile Ser Lys Thr Thr Gly
 15              20                  25                  30

CGG CAT CTA CCG CCG GGG CCA AGA GGG TGG CCG GTG ATC GGA GCA CTT      263
Arg His Leu Pro Pro Gly Pro Arg Gly Trp Pro Val Ile Gly Ala Leu
                 35                  40                  45

CCA CTT TTA GGA GCC ATG CCA CAT GTT TCC TTA GCT AAA ATG GCA AAA      311
Pro Leu Leu Gly Ala Met Pro His Val Ser Leu Ala Lys Met Ala Lys
             50                  55                  60

AAA TAT GGA GCA ATC ATG TAT CTC AAA GTT GGA ACA TGT GGC ATG GCA      359
Lys Tyr Gly Ala Ile Met Tyr Leu Lys Val Gly Thr Cys Gly Met Ala
         65                  70                  75

GTT GCT TCT ACC CCT GAT GCT GCT AAA GCA TTC TTG AAA ACA CTT GAT      407
Val Ala Ser Thr Pro Asp Ala Ala Lys Ala Phe Leu Lys Thr Leu Asp
     80                  85                  90

ATC AAC TTC TCC AAT CGT CCA CCT AAT GCA GGT GCC ACT CAC TTA GCT      455
Ile Asn Phe Ser Asn Arg Pro Pro Asn Ala Gly Ala Thr His Leu Ala
 95                 100                 105                 110

TAT AAT GCT CAA GAC ATG GTT TTT GCA CAT TAT GGA CCA CGA TGG AAG      503
Tyr Asn Ala Gln Asp Met Val Phe Ala His Tyr Gly Pro Arg Trp Lys
                115                 120                 125

TTG CTA AGG AAA TTA AGC AAC TTG CAT ATG CTA GGG GGA AAA GCC TTA      551
Leu Leu Arg Lys Leu Ser Asn Leu His Met Leu Gly Gly Lys Ala Leu
            130                 135                 140

GAG AAT TGG GCA AAT GTT CGT GCC AAT GAG CTA GGG CAC ATG CTA AAA      599
Glu Asn Trp Ala Asn Val Arg Ala Asn Glu Leu Gly His Met Leu Lys
        145                 150                 155

TCA ATG TCC GAT ATG AGT CGA GAG GGC CAG AGG GTT GTG GTG GCG GAG      647
Ser Met Ser Asp Met Ser Arg Glu Gly Gln Arg Val Val Val Ala Glu
160                 165                 170

ATG TTG ACA TTT GCC ATG GCC AAT ATG ATC GGA CAA GTG ATG CTA AGC      695
Met Leu Thr Phe Ala Met Ala Asn Met Ile Gly Gln Val Met Leu Ser
175                 180                 185                 190

AAA AGA GTA TTT GTA GAT AAA GGT GTT GAG GTA AAT GAA TTT AAG GAC      743
Lys Arg Val Phe Val Asp Lys Gly Val Glu Val Asn Glu Phe Lys Asp
            195                 200                 205

ATG GTT GTA GAG TTA ATG ACA ATA GCA GGG TAT TTC AAC ATT GGT GAT      791
Met Val Val Glu Leu Met Thr Ile Ala Gly Tyr Phe Asn Ile Gly Asp
        210                 215                 220

TTT ATT CCT TGT TTA GCT TGG ATG GAT TTA CAA GGG ATA GAA AAA CGA      839
Phe Ile Pro Cys Leu Ala Trp Met Asp Leu Gln Gly Ile Glu Lys Arg
225                 230                 235

ATG AAA CGT TTA CAT AAG AAG TTT GAT GCT TTA TTG ACA AAG ATG TTT      887
```

```
Met Lys Arg Leu His Lys Lys Phe Asp Ala Leu Leu Thr Lys Met Phe
    240             245                 250

GAT GAA CAC AAA GCA ACT ACC TAT GAA CGT AAG GGG AAA CCA GAT TTT         935
Asp Glu His Lys Ala Thr Thr Tyr Glu Arg Lys Gly Lys Pro Asp Phe
    255             260                 265                 270

CTT GAT GTT GTT ATG GAA AAT GGG GAC AAT TCT GAA GGA GAA AGA CTC         983
Leu Asp Val Val Met Glu Asn Gly Asp Asn Ser Glu Gly Glu Arg Leu
                275                 280                 285

AGT ACA ACC AAC ATC AAA GCA CTT TTG CTG AAT TTG TTC ACA GCT GGT        1031
Ser Thr Thr Asn Ile Lys Ala Leu Leu Leu Asn Leu Phe Thr Ala Gly
                290                 295                 300

ACG GAC ACT TCT TCT AGT GCA ATA GAA TGG GCA CTT GCA GAA ATG ATG        1079
Thr Asp Thr Ser Ser Ser Ala Ile Glu Trp Ala Leu Ala Glu Met Met
            305                 310                 315

AAG AAC CCT GCC ATT TTG AAA AAA GCA CAA GCA GAA ATG GAT CAA GTC        1127
Lys Asn Pro Ala Ile Leu Lys Lys Ala Gln Ala Glu Met Asp Gln Val
        320                 325                 330

ATT GGA AGA AAT AGG CGT TTA CTC GAA TCC GAT ATC CCA AAT CTC CCT        1175
Ile Gly Arg Asn Arg Arg Leu Leu Glu Ser Asp Ile Pro Asn Leu Pro
335                 340                 345                 350

TAC CTC CGA GCA ATT TGC AAA GAA ACA TTT CGA AAA CAC CCT TCT ACA        1223
Tyr Leu Arg Ala Ile Cys Lys Glu Thr Phe Arg Lys His Pro Ser Thr
                355                 360                 365

CCA TTA AAT CTT CCT AGG ATC TCG AAC GAA CCA TGC ATA GTC GAT GGT        1271
Pro Leu Asn Leu Pro Arg Ile Ser Asn Glu Pro Cys Ile Val Asp Gly
            370                 375                 380

TAT TAC ATA CCA AAA AAC ACT AGG CTT AGT GTT AAC ATA TGG GCA ATT        1319
Tyr Tyr Ile Pro Lys Asn Thr Arg Leu Ser Val Asn Ile Trp Ala Ile
        385                 390                 395

GGA AGA GAT CCC CAA GTT TGG GAA AAT CCA CTA GAG TTT AAT CCC GAA        1367
Gly Arg Asp Pro Gln Val Trp Glu Asn Pro Leu Glu Phe Asn Pro Glu
400                 405                 410

AGA TTC TTG AGT GGA AGA AAC TCC AAG ATT GAT CCT CGA GGG AAC GAT        1415
Arg Phe Leu Ser Gly Arg Asn Ser Lys Ile Asp Pro Arg Gly Asn Asp
415                 420                 425                 430

TTT GAA TTG ATA CCA TTT GGT GCT GGA CGA AGA ATT TGT GCA GGA ACA        1463
Phe Glu Leu Ile Pro Phe Gly Ala Gly Arg Arg Ile Cys Ala Gly Thr
                435                 440                 445

AGA ATG GGA ATT GTA ATG GTG GAA TAT ATA TTA GGA ACT TTG GTT CAT        1511
Arg Met Gly Ile Val Met Val Glu Tyr Ile Leu Gly Thr Leu Val His
            450                 455                 460

TCA TTT GAT TGG AAA TTA CCA AGT GAA GTT ATT GAG TTG AAT ATG GAA        1559
Ser Phe Asp Trp Lys Leu Pro Ser Glu Val Ile Glu Leu Asn Met Glu
        465                 470                 475

GAA GCT TTT GGC TTA GCT TTG CAG AAA GCT GTC CCT CTT GAA GCT ATG        1607
Glu Ala Phe Gly Leu Ala Leu Gln Lys Ala Val Pro Leu Glu Ala Met
    480                 485                 490

GTT ACT CCA AGG TTA CAA TTG GAT GTT TAT GTA CCA TAGCTATAGA             1653
Val Thr Pro Arg Leu Gln Leu Asp Val Tyr Val Pro
495                 500                 505

TGTGTATTGT GCTATAATTG CGCATGTTGT TGGTTGTAGC ATGAGATATT AAAAGGAGTA     1713

CATGAAGCGC ATTGCATGAG TTTAACTTGT AGCTCCTTAA TATTTAGGT ATTTTTCAAT      1773

TAATAAGTTC TTGTTGGTTG GGTAAAAAAA AAAAAAAA                              1812
```

( 2 ) INFORMATION FOR SEQ ID NO:38:

( i ) SEQUENCE CHARACTERISTICS:
        ( A ) LENGTH: 506 amino acids
        ( B ) TYPE: amino acid
        ( D ) TOPOLOGY: linear ( i i ) MOLECULE TYPE: protein ( x i ) SEQUENCE DESCRIPTION: SEQ ID NO:38:

| Met | Met | Leu | Leu | Thr | Glu | Leu | Gly | Ala | Ala | Thr | Ser | Ile | Phe | Leu | Ile |
|---|---|---|---|---|---|---|---|---|---|---|---|---|---|---|---|
| 1 | | | | 5 | | | | | 10 | | | | | 15 | |
| Ala | His | Ile | Ile | Ile | Ser | Thr | Leu | Ile | Ser | Lys | Thr | Thr | Gly | Arg | His |
| | | | 20 | | | | | 25 | | | | 30 | | | |
| Leu | Pro | Pro | Gly | Pro | Arg | Gly | Trp | Pro | Val | Ile | Gly | Ala | Leu | Pro | Leu |
| | | 35 | | | | | 40 | | | | | 45 | | | |
| Leu | Gly | Ala | Met | Pro | His | Val | Ser | Leu | Ala | Lys | Met | Ala | Lys | Lys | Tyr |
| | 50 | | | | 55 | | | | | 60 | | | | | |
| Gly | Ala | Ile | Met | Tyr | Leu | Lys | Val | Gly | Thr | Cys | Gly | Met | Ala | Val | Ala |
| 65 | | | | | 70 | | | | | 75 | | | | | 80 |
| Ser | Thr | Pro | Asp | Ala | Ala | Lys | Ala | Phe | Leu | Lys | Thr | Leu | Asp | Ile | Asn |
| | | | | 85 | | | | | 90 | | | | | | 95 |
| Phe | Ser | Asn | Arg | Pro | Pro | Asn | Ala | Gly | Ala | Thr | His | Leu | Ala | Tyr | Asn |
| | | | 100 | | | | | 105 | | | | | 110 | | |
| Ala | Gln | Asp | Met | Val | Phe | Ala | His | Tyr | Gly | Pro | Arg | Trp | Lys | Leu | Leu |
| | | | 115 | | | | | 120 | | | | | 125 | | |
| Arg | Lys | Leu | Ser | Asn | Leu | His | Met | Leu | Gly | Gly | Lys | Ala | Leu | Glu | Asn |
| | 130 | | | | | 135 | | | | | 140 | | | | |
| Trp | Ala | Asn | Val | Arg | Ala | Asn | Glu | Leu | Gly | His | Met | Leu | Lys | Ser | Met |
| 145 | | | | | 150 | | | | | 155 | | | | | 160 |
| Ser | Asp | Met | Ser | Arg | Glu | Gly | Gln | Arg | Val | Val | Val | Ala | Glu | Met | Leu |
| | | | | 165 | | | | | 170 | | | | | 175 | |
| Thr | Phe | Ala | Met | Ala | Asn | Met | Ile | Gly | Gln | Val | Met | Leu | Ser | Lys | Arg |
| | | | 180 | | | | | 185 | | | | | 190 | | |
| Val | Phe | Val | Asp | Lys | Gly | Val | Glu | Val | Asn | Glu | Phe | Lys | Asp | Met | Val |
| | | 195 | | | | | 200 | | | | | 205 | | | |
| Val | Glu | Leu | Met | Thr | Ile | Ala | Gly | Tyr | Phe | Asn | Ile | Gly | Asp | Phe | Ile |
| | 210 | | | | | 215 | | | | | 220 | | | | |
| Pro | Cys | Leu | Ala | Trp | Met | Asp | Leu | Gln | Gly | Ile | Glu | Lys | Arg | Met | Lys |
| 225 | | | | | 230 | | | | | 235 | | | | | 240 |
| Arg | Leu | His | Lys | Lys | Phe | Asp | Ala | Leu | Leu | Thr | Lys | Met | Phe | Asp | Glu |
| | | | | 245 | | | | | 250 | | | | | 255 | |
| His | Lys | Ala | Thr | Thr | Tyr | Glu | Arg | Lys | Gly | Lys | Pro | Asp | Phe | Leu | Asp |
| | | | 260 | | | | | 265 | | | | | 270 | | |
| Val | Val | Met | Glu | Asn | Gly | Asp | Asn | Ser | Glu | Gly | Glu | Arg | Leu | Ser | Thr |
| | | 275 | | | | | 280 | | | | | 285 | | | |
| Thr | Asn | Ile | Lys | Ala | Leu | Leu | Leu | Asn | Leu | Phe | Thr | Ala | Gly | Thr | Asp |
| | 290 | | | | | 295 | | | | | 300 | | | | |
| Thr | Ser | Ser | Ser | Ala | Ile | Glu | Trp | Ala | Leu | Ala | Glu | Met | Met | Lys | Asn |
| 305 | | | | | 310 | | | | | 315 | | | | | 320 |
| Pro | Ala | Ile | Leu | Lys | Lys | Ala | Gln | Ala | Glu | Met | Asp | Gln | Val | Ile | Gly |
| | | | | 325 | | | | | 330 | | | | | 335 | |
| Arg | Asn | Arg | Arg | Leu | Leu | Glu | Ser | Asp | Ile | Pro | Asn | Leu | Pro | Tyr | Leu |
| | | | 340 | | | | | 345 | | | | | 350 | | |
| Arg | Ala | Ile | Cys | Lys | Glu | Thr | Phe | Arg | Lys | His | Pro | Ser | Thr | Pro | Leu |
| | | 355 | | | | | 360 | | | | | 365 | | | |
| Asn | Leu | Pro | Arg | Ile | Ser | Asn | Glu | Pro | Cys | Ile | Val | Asp | Gly | Tyr | Tyr |
| | 370 | | | | | 375 | | | | | 380 | | | | |
| Ile | Pro | Lys | Asn | Thr | Arg | Leu | Ser | Val | Asn | Ile | Trp | Ala | Ile | Gly | Arg |
| 385 | | | | | 390 | | | | | 395 | | | | | 400 |

|   |   |   |   |   |   |   |   |   |   |   |   |   |   |   |
|---|---|---|---|---|---|---|---|---|---|---|---|---|---|---|
| Asp | Pro | Gln | Val | Trp<br>405 | Glu | Asn | Pro | Leu<br>410 | Glu | Phe | Asn | Pro | Glu<br>415 | Arg | Phe |
| Leu | Ser | Gly | Arg<br>420 | Asn | Ser | Lys | Ile | Asp<br>425 | Pro | Arg | Gly | Asn | Asp<br>430 | Phe | Glu |
| Leu | Ile | Pro<br>435 | Phe | Gly | Ala | Gly | Arg<br>440 | Arg | Ile | Cys | Ala | Gly<br>445 | Thr | Arg | Met |
| Gly | Ile<br>450 | Val | Met | Val | Glu | Tyr<br>455 | Ile | Leu | Gly | Thr | Leu<br>460 | Val | His | Ser | Phe |
| Asp<br>465 | Trp | Lys | Leu | Pro | Ser<br>470 | Glu | Val | Ile | Glu | Leu<br>475 | Asn | Met | Glu | Glu | Ala<br>480 |
| Phe | Gly | Leu | Ala | Leu<br>485 | Gln | Lys | Ala | Val | Pro<br>490 | Leu | Glu | Ala | Met | Val<br>495 | Thr |
| Pro | Arg | Leu | Gln<br>500 | Leu | Asp | Val | Tyr | Val<br>505 | Pro |   |   |   |   |   |   |

( 2 ) INFORMATION FOR SEQ ID NO:39:

( i ) SEQUENCE CHARACTERISTICS:
        ( A ) LENGTH: 180 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:39:

| | | | | | |
|---|---|---|---|---|---|
| CCAGACACCC | ACAAACTTCC | ATACCTTCAG | GCTGTGATCA | AGGAGACTCT | TCGTCTCCGG | 60 |
| ATGGCAATTC | CTCTATTAGT | CCCACACATG | AAACTTTACA | GAAAACGTTC | ATCTTTTTAT | 120 |
| GTCATATCAA | GTCTTCTTGG | ACTGGTTCGT | TATTACACCT | ACCTATCTGA | ATGTATTTTT | 180 |

( 2 ) INFORMATION FOR SEQ ID NO:40:

( i ) SEQUENCE CHARACTERISTICS:
        ( A ) LENGTH: 180 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:40:

| | | | | | |
|---|---|---|---|---|---|
| ACGAACATGG | GAAAATCCAG | AAGAGTATCA | GCCAGAGAGA | TTCTTGAATA | GTGATATTGA | 60 |
| TGTCAAAGGA | CTAAACTTTG | AGTTGATTCC | ATGGCTAGTA | GCTACTTCTT | TCATGATATC | 120 |
| TGTAATAAGT | GTAGTGCTCG | ACTCCTTCAG | GCGAGTTGTG | TGTTTAATTT | CTCCAGTATC | 180 |

( 2 ) INFORMATION FOR SEQ ID NO:41:

( i ) SEQUENCE CHARACTERISTICS:
        ( A ) LENGTH: 180 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:41:

| | | | | | |
|---|---|---|---|---|---|
| AAGTTCTTTC | CATCAGTTAT | CAAACAAACC | ATGAGGCTGC | ATCCCCTCT | CCCTTTATTA | 60 |
| CTATTAAGGG | AAAGCAAGGA | ATCTTGTGAA | GATAGGGAGC | GGTTACTCC | CTTCGTGGCC | 120 |
| TTACCATTAC | ACTAACAATG | AATGGGCTTG | GAAATAGTCT | CAGATGTTTT | TAAAGAAAAC | 180 |

( 2 ) INFORMATION FOR SEQ ID NO:42:

( i ) SEQUENCE CHARACTERISTICS:
   ( A ) LENGTH: 179 base pairs
   ( B ) TYPE: nucleic acid
   ( C ) STRANDEDNESS: single
   ( D ) TOPOLOGY: linear ( i i ) MOLECULE TYPE: DNA ( x i ) SEQUENCE DESCRIPTION: SEQ ID NO:42:

| | | | | | |
|---|---|---|---|---|---|
| GTGATTTTCC | AAAAGAATCT | CACTTGCTGC | AGATGTCCTA | TGTTCAAGCC | TGTGTGAAGG | 60
| AAACTCTTAG | GTTGCATCCT | CCGGCGCCAT | TATTTATTGA | AGTTGAGAAA | CTTATGTATG | 120
| AAAGTGTCAT | ACAGAACTAC | TGCCCATGTG | GTGTGTTTTA | GTACTTCTTT | TTTTTGGGT | 179

( 2 ) INFORMATION FOR SEQ ID NO:43:

( i ) SEQUENCE CHARACTERISTICS:
      ( A ) LENGTH: 180 base pairs
      ( B ) TYPE: nucleic acid
      ( C ) STRANDEDNESS: single
      ( D ) TOPOLOGY: linear ( i i ) MOLECULE TYPE: DNA ( x i ) SEQUENCE DESCRIPTION: SEQ ID NO:43:

| | | | | | |
|---|---|---|---|---|---|
| ATGTCCTATG | TTCAAGCCTG | TGTGCCGGAA | ACTCTTAGGT | TGCATCCTCC | GGCGCCATTG | 60
| CTACTTCCAC | ATGCGTGCAA | TCGAAACATG | TCCCCCTGGA | TTTGTACACT | AGATACAAGA | 120
| CTTAGCGGTC | CTGGTGTAAT | CTCAATTCTC | ATGTGGTTAT | AAACAGAAGT | TCTTCTGGTG | 180

( 2 ) INFORMATION FOR SEQ ID NO:44:

( i ) SEQUENCE CHARACTERISTICS:
      ( A ) LENGTH: 180 base pairs
      ( B ) TYPE: nucleic acid
      ( C ) STRANDEDNESS: single
      ( D ) TOPOLOGY: linear ( i i ) MOLECULE TYPE: DNA ( x i ) SEQUENCE DESCRIPTION: SEQ ID NO:44:

| | | | | | |
|---|---|---|---|---|---|
| GAAACATTAT | CAATGAACAT | GTTAAGAATC | GAGCACTCGG | AAGCAAGGGA | AATGGTGCGT | 60
| TTGGAGGTGA | AGATTTGGTT | GATGTTTTAC | GGTTGGGGTA | AATTGGGGCC | CCCCTTTTAA | 120
| GGCTTTGGAA | TTTCCACCTG | GAAAAATGGA | CCCCATTTTC | CTTTTCCTGT | ACCTCCAATT | 180

( 2 ) INFORMATION FOR SEQ ID NO:45:

( i ) SEQUENCE CHARACTERISTICS:
      ( A ) LENGTH: 90 base pairs
      ( B ) TYPE: nucleic acid
      ( C ) STRANDEDNESS: single
      ( D ) TOPOLOGY: linear ( i i ) MOLECULE TYPE: DNA ( x i ) SEQUENCE DESCRIPTION: SEQ ID NO:45:

| | | | | | |
|---|---|---|---|---|---|
| AAAACTGCAA | ACTAGCGATA | ACGCTGATGT | TCTTGATGTG | TTGTTGCATA | CTAGCGAGGA | 60
| AGATCCAGAG | GCAATCGACA | GAATTCACAT | | | | 90

( 2 ) INFORMATION FOR SEQ ID NO:46:

( i ) SEQUENCE CHARACTERISTICS:
      ( A ) LENGTH: 180 base pairs
      ( B ) TYPE: nucleic acid
      ( C ) STRANDEDNESS: single
      ( D ) TOPOLOGY: linear (ii) MOLECULE TYPE: DNA (xi) SEQUENCE DESCRIPTION: SEQ ID NO:46:

| | | | | | |
|---|---|---|---|---|---|
| CAGTACACTC | TTTGTGTTCA | TCATATCTCT | TCACATTGCT | CACAAGCTCG | ACCATGGCCG | 60 |
| TCGGTAAGAA | CAAGAGGATT | TCCAAAGGCA | AATACCACAT | TCTGATGATT | CACTTGATAT | 120 |
| ATGTGTACCT | TTATGTCATT | TAATGGCACA | ACAATTCTGG | GGACTTAGGT | TCAAAGAAGC | 180 |

(2) INFORMATION FOR SEQ ID NO:47:

(i) SEQUENCE CHARACTERISTICS:
        (A) LENGTH: 180 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:47:

| | | | | | |
|---|---|---|---|---|---|
| CTGTAGGGTT | ACCGTTCATT | GGAAATTTGC | ATCAATATGA | TACTTTAAAG | CCGCATATCT | 60 |
| ACTTCTGGAA | ACTTTCTAGG | AAGTATGGAA | TACTTTCGGT | TTTGAATTAT | GTATACATAT | 120 |
| ATAAAACAAA | TGTGAAATGT | ATACATATAA | TAAAATTGCT | CTCATGATAT | ACTTCTCTAT | 180 |

(2) INFORMATION FOR SEQ ID NO:48:

(i) SEQUENCE CHARACTERISTICS:
        (A) LENGTH: 179 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:48:

| | | | | | |
|---|---|---|---|---|---|
| TTCTGGAAAT | GTTTCTAGCT | GGTACAGAGA | CATCTAGCAG | CACAACAGAG | TGGGCACTAA | 60 |
| CTGAACTCCT | TCGAAACCCA | GAAACAATGG | ACAATTCTTA | CGCTGAATTT | GTTGTTCGCC | 120 |
| CTTTTATTTT | CAGTTTGATT | GTATCCAAAG | GATGTCGAAT | GAAATCATAC | TCTTTACCT | 179 |

(2) INFORMATION FOR SEQ ID NO:49:

(i) SEQUENCE CHARACTERISTICS:
        (A) LENGTH: 1757 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: CDS
        (B) LOCATION: 35..1522

(xi) SEQUENCE DESCRIPTION: SEQ ID NO:49:

| | | | | | | | | | | |
|---|---|---|---|---|---|---|---|---|---|---|
| CCGTTGCTGT | CGAGAAAACA | GAAAGAAGAG | AAAA | ATG<br>Met<br>1 | GAC<br>Asp | TAC<br>Tyr | GTG<br>Val | AAT<br>Asn | ATT<br>Ile<br>5 | 52 |

| TTG<br>Leu | CTG<br>Leu | GGA<br>Gly | CTG<br>Leu<br>10 | TTT<br>Phe | TTC<br>Phe | ACT<br>Thr | TGG<br>Trp | TTC<br>Phe<br>15 | TTG<br>Leu | GTG<br>Val | AAT<br>Asn | GGA<br>Gly | CTC<br>Leu<br>20 | ATG<br>Met | TCA<br>Ser | 100 |
| CTT<br>Leu | CGA<br>Arg | AGA<br>Arg<br>25 | AGA<br>Arg | AAA<br>Lys | ATC<br>Ile | TCT<br>Ser | AAG<br>Lys<br>30 | AAA<br>Lys | CTT<br>Leu | CCA<br>Pro | CCA<br>Pro | GGT<br>Gly<br>35 | CCA<br>Pro | TTT<br>Phe | CCT<br>Pro | 148 |
| TTG<br>Leu | CCT<br>Pro | ATC<br>Ile | ATC<br>Ile | GGA<br>Gly | AAT<br>Asn | CTT<br>Leu | CAC<br>His | TTA<br>Leu | CTT<br>Leu | GGT<br>Gly | AAT<br>Asn | CAT<br>His | CCT<br>Pro | CAC<br>His | AAA<br>Lys | 196 |

```
                    40                          45                          50
TCA CTT GCT CAA CTT GCA AAA ATT CAT GGT CCT ATT ATG AAT CTC AAA            244
Ser Leu Ala Gln Leu Ala Lys Ile His Gly Pro Ile Met Asn Leu Lys
 55              60                  65                      70

TTA GGC CAA CTA AAC ACA GTG GTC ATT TCA TCA TCA GTC GTG GCA AGA            292
Leu Gly Gln Leu Asn Thr Val Val Ile Ser Ser Ser Val Val Ala Arg
             75                  80                  85

GAA GTC TTG CAA AAA CAA GAC TTA ACA TTT TCC AAT AGG TTT GTC CCG            340
Glu Val Leu Gln Lys Gln Asp Leu Thr Phe Ser Asn Arg Phe Val Pro
                 90                  95                 100

GAC GTA GTC CAT GTC CGA AAT CAC TCC GAT TTT TCT GTT GTT TGG TTA            388
Asp Val Val His Val Arg Asn His Ser Asp Phe Ser Val Val Trp Leu
            105                 110                 115

CCA GTC AAT TCT CGA TGG AAA ACG CTT CGC AAA ATC ATG AAC TCT AGC            436
Pro Val Asn Ser Arg Trp Lys Thr Leu Arg Lys Ile Met Asn Ser Ser
        120                 125                 130

ATC TTT TCT GGT AAC AAG CTT GAT GGT AAT CAA CAT CTG AGG TCT AAA            484
Ile Phe Ser Gly Asn Lys Leu Asp Gly Asn Gln His Leu Arg Ser Lys
135                 140                 145                 150

AAG GTC CAA GAG TTA ATT GAT TAT TGT CAA AAG TGT GCC AAG AAT GGC            532
Lys Val Gln Glu Leu Ile Asp Tyr Cys Gln Lys Cys Ala Lys Asn Gly
                155                 160                 165

GAA GCA GTG GAT ATA GGA AGA GCA ACT TTT GGA ACT ACT TTG AAT TTG            580
Glu Ala Val Asp Ile Gly Arg Ala Thr Phe Gly Thr Thr Leu Asn Leu
            170                 175                 180

CTA TCC AAC ACC ATT TTC TCT AAA GAT TTG ACT AAT CCG TTT TCT GAT            628
Leu Ser Asn Thr Ile Phe Ser Lys Asp Leu Thr Asn Pro Phe Ser Asp
        185                 190                 195

TCT GCT AAA GAG TTT AAG GAA TTG GTT TGG AAC ATT ATG GTT GAG GCT            676
Ser Ala Lys Glu Phe Lys Glu Leu Val Trp Asn Ile Met Val Glu Ala
200                 205                 210

GGA AAA CCC AAT TTG GTG GAC TAC TTT CCT TTC CTT GAG AAA ATT GAT            724
Gly Lys Pro Asn Leu Val Asp Tyr Phe Pro Phe Leu Glu Lys Ile Asp
215                 220                 225                 230

CCG CAA GGT ATA AAG CGA CGC ATG ACT AAT AAT TTT ACT AAG TTT CTT            772
Pro Gln Gly Ile Lys Arg Arg Met Thr Asn Asn Phe Thr Lys Phe Leu
                235                 240                 245

GGC CTT ATC AGC GGT TTG ATT GAT GAC CGG TTA AAG GAA AGG AAT CTA            820
Gly Leu Ile Ser Gly Leu Ile Asp Asp Arg Leu Lys Glu Arg Asn Leu
            250                 255                 260

AGG GAC AAT GCA AAT ATT GAT GTT TTA GAC GCC CTT CTC AAC ATT AGC            868
Arg Asp Asn Ala Asn Ile Asp Val Leu Asp Ala Leu Leu Asn Ile Ser
        265                 270                 275

CAA GAG AAC CCA GAA GAG ATT GAC AGG AAT CAA ATC GAG CAG TTG TGT            916
Gln Glu Asn Pro Glu Glu Ile Asp Arg Asn Gln Ile Glu Gln Leu Cys
280                 285                 290

CTG GAC TTG TTT GCA GCA GGG ACT GAT ACT ACA TCG AAT ACC TTG GAG            964
Leu Asp Leu Phe Ala Ala Gly Thr Asp Thr Thr Ser Asn Thr Leu Glu
295                 300                 305                 310

TGG GCA ATG GCA GAA CTA CTT CAG AAT CCA CAC ACA TTG CAG AAA GCA           1012
Trp Ala Met Ala Glu Leu Leu Gln Asn Pro His Thr Leu Gln Lys Ala
                315                 320                 325

CAA GAA GAA CTT GCA CAA GTC ATT GGT AAA GGC AAA CAA GTA GAA GAA           1060
Gln Glu Glu Leu Ala Gln Val Ile Gly Lys Gly Lys Gln Val Glu Glu
            330                 335                 340

GCA GAT GTT GGA CGA CTA CCT TAC TTG CGA TGC ATA GTG AAA GAA ACC           1108
Ala Asp Val Gly Arg Leu Pro Tyr Leu Arg Cys Ile Val Lys Glu Thr
        345                 350                 355

TTA CGA ATA CAC CCA GCG GCT CCT CTC TTA ATT CCA CGT AAA GTG GAG           1156
Leu Arg Ile His Pro Ala Ala Pro Leu Leu Ile Pro Arg Lys Val Glu
```

-continued

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     | 360 |     |     |     |     | 365 |     |     |     |     | 370 |     |     |     |      |
| GAA | GAC | GTT | GAG | TTG | TCT | ACC | TAT | ATT | ATT | CCA | AAG | GAT | TCA | CAA | GTT | 1204 |
| Glu | Asp | Val | Glu | Leu | Ser | Thr | Tyr | Ile | Ile | Pro | Lys | Asp | Ser | Gln | Val |      |
| 375 |     |     |     |     | 380 |     |     |     |     | 385 |     |     |     |     | 390 |      |
| CTA | GTG | AAC | GTA | TGG | GCA | ATT | GGA | CGC | AAC | TCT | GAT | CTA | TGG | GAA | AAT | 1252 |
| Leu | Val | Asn | Val | Trp | Ala | Ile | Gly | Arg | Asn | Ser | Asp | Leu | Trp | Glu | Asn |      |
|     |     |     |     | 395 |     |     |     |     | 400 |     |     |     |     | 405 |     |      |
| CCT | TTG | GTC | TTT | AAG | CCA | GAA | AGG | TTT | TGG | GAG | TCA | GAA | ATA | GAT | ATC | 1300 |
| Pro | Leu | Val | Phe | Lys | Pro | Glu | Arg | Phe | Trp | Glu | Ser | Glu | Ile | Asp | Ile |      |
|     |     |     | 410 |     |     |     |     | 415 |     |     |     |     | 420 |     |     |      |
| CGA | GGT | CGA | GAT | TTT | GAA | CTC | ATT | CCA | TTT | GGT | GCT | GGT | CGA | AGA | ATT | 1348 |
| Arg | Gly | Arg | Asp | Phe | Glu | Leu | Ile | Pro | Phe | Gly | Ala | Gly | Arg | Arg | Ile |      |
|     |     | 425 |     |     |     |     | 430 |     |     |     |     | 435 |     |     |     |      |
| TGC | CCT | GGA | TTG | CCT | TTG | GCT | ATG | AGG | ATG | ATT | CCA | GTA | GCA | CTA | GGT | 1396 |
| Cys | Pro | Gly | Leu | Pro | Leu | Ala | Met | Arg | Met | Ile | Pro | Val | Ala | Leu | Gly |      |
|     | 440 |     |     |     |     | 445 |     |     |     |     | 450 |     |     |     |     |      |
| TCA | TTG | CTA | AAC | TCA | TTT | AAT | TGG | AAA | CTA | TAT | GGT | GGA | ATT | GCA | CCT | 1444 |
| Ser | Leu | Leu | Asn | Ser | Phe | Asn | Trp | Lys | Leu | Tyr | Gly | Gly | Ile | Ala | Pro |      |
| 455 |     |     |     |     | 460 |     |     |     |     | 465 |     |     |     |     | 470 |      |
| AAA | GAT | TTG | GAC | ATG | CAG | GAA | AAG | TTT | GGC | ATT | ACC | TTG | GCG | AAA | GCC | 1492 |
| Lys | Asp | Leu | Asp | Met | Gln | Glu | Lys | Phe | Gly | Ile | Thr | Leu | Ala | Lys | Ala |      |
|     |     |     |     | 475 |     |     |     |     | 480 |     |     |     |     | 485 |     |      |
| CAA | CCT | CTG | CTA | GCT | ATC | CCA | ACT | CCC | CTG | TAGCTATAGG | | GATAAATTAA | | | | 1542 |
| Gln | Pro | Leu | Leu | Ala | Ile | Pro | Thr | Pro | Leu |     |     |     |     |     |     |      |
|     |     |     | 490 |     |     |     |     | 495 |     |     |     |     |     |     |     |      |

| GTTGAGGTTT | TAAGTTACTA | GTAGATTCTA | TTGCAGCTAT | AGGATTTCTT | TCACCATCAC | 1602 |
| GTATGCTTTA | CCGTTGGATG | ATGGAAAGAA | ATATCTATAG | CTTTGGGTTT | GTTTAGTTTG | 1662 |
| CACATAAAAA | TTGAATGAAT | GGAATACCAT | GGAGTTATAA | GAAATAATAA | GACTATGATT | 1722 |
| CTTACCCTAC | TTGAACAATG | ACATGGCTAT | TTCAC | | | 1757 |

( 2 ) INFORMATION FOR SEQ ID NO:50:

( i ) SEQUENCE CHARACTERISTICS:
        ( A ) LENGTH: 496 amino acids
        ( B ) TYPE: amino acid
        ( D ) TOPOLOGY: linear ( i i ) MOLECULE TYPE: protein ( x i ) SEQUENCE DESCRIPTION: SEQ ID NO:50:

| Met | Asp | Tyr | Val | Asn | Ile | Leu | Leu | Gly | Leu | Phe | Phe | Thr | Trp | Phe | Leu |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Val | Asn | Gly | Leu | Met | Ser | Leu | Arg | Arg | Arg | Lys | Ile | Ser | Lys | Lys | Leu |
|     |     |     | 20  |     |     |     |     | 25  |     |     |     |     | 30  |     |     |
| Pro | Pro | Gly | Pro | Phe | Pro | Leu | Pro | Ile | Ile | Gly | Asn | Leu | His | Leu | Leu |
|     |     | 35  |     |     |     |     | 40  |     |     |     |     | 45  |     |     |     |
| Gly | Asn | His | Pro | His | Lys | Ser | Leu | Ala | Gln | Leu | Ala | Lys | Ile | His | Gly |
|     | 50  |     |     |     |     | 55  |     |     |     |     | 60  |     |     |     |     |
| Pro | Ile | Met | Asn | Leu | Lys | Leu | Gly | Gln | Leu | Asn | Thr | Val | Val | Ile | Ser |
| 65  |     |     |     |     | 70  |     |     |     |     | 75  |     |     |     |     | 80  |
| Ser | Ser | Val | Val | Ala | Arg | Glu | Val | Leu | Gln | Lys | Gln | Asp | Leu | Thr | Phe |
|     |     |     |     | 85  |     |     |     |     | 90  |     |     |     |     | 95  |     |
| Ser | Asn | Arg | Phe | Val | Pro | Asp | Val | Val | His | Val | Arg | Asn | His | Ser | Asp |
|     |     |     | 100 |     |     |     |     | 105 |     |     |     |     | 110 |     |     |
| Phe | Ser | Val | Val | Trp | Leu | Pro | Val | Asn | Ser | Arg | Trp | Lys | Thr | Leu | Arg |
|     |     |     | 115 |     |     |     |     | 120 |     |     |     |     | 125 |     |     |
| Lys | Ile | Met | Asn | Ser | Ser | Ile | Phe | Ser | Gly | Asn | Lys | Leu | Asp | Gly | Asn |
|     |     | 130 |     |     |     |     | 135 |     |     |     |     | 140 |     |     |     |

| | | | | | | | | | | | | | | | |
|---|---|---|---|---|---|---|---|---|---|---|---|---|---|---|---|
| Gln | His | Leu | Arg | Ser | Lys | Lys | Val | Gln | Glu | Leu | Ile | Asp | Tyr | Cys | Gln |
| 145 | | | | | 150 | | | | | 155 | | | | | 160 |
| Lys | Cys | Ala | Lys | Asn | Gly | Glu | Ala | Val | Asp | Ile | Gly | Arg | Ala | Thr | Phe |
| | | | | 165 | | | | | 170 | | | | | 175 | |
| Gly | Thr | Thr | Leu | Asn | Leu | Leu | Ser | Asn | Thr | Ile | Phe | Ser | Lys | Asp | Leu |
| | | | 180 | | | | | 185 | | | | | 190 | | |
| Thr | Asn | Pro | Phe | Ser | Asp | Ser | Ala | Lys | Glu | Phe | Lys | Glu | Leu | Val | Trp |
| | | 195 | | | | | 200 | | | | | 205 | | | |
| Asn | Ile | Met | Val | Glu | Ala | Gly | Lys | Pro | Asn | Leu | Val | Asp | Tyr | Phe | Pro |
| | 210 | | | | | 215 | | | | | 220 | | | | |
| Phe | Leu | Glu | Lys | Ile | Asp | Pro | Gln | Gly | Ile | Lys | Arg | Arg | Met | Thr | Asn |
| 225 | | | | 230 | | | | | 235 | | | | | | 240 |
| Asn | Phe | Thr | Lys | Phe | Leu | Gly | Leu | Ile | Ser | Gly | Leu | Ile | Asp | Asp | Arg |
| | | | | 245 | | | | | 250 | | | | | 255 | |
| Leu | Lys | Glu | Arg | Asn | Leu | Arg | Asp | Asn | Ala | Asn | Ile | Asp | Val | Leu | Asp |
| | | | 260 | | | | | 265 | | | | | 270 | | |
| Ala | Leu | Leu | Asn | Ile | Ser | Gln | Glu | Asn | Pro | Glu | Glu | Ile | Asp | Arg | Asn |
| | | 275 | | | | | 280 | | | | | 285 | | | |
| Gln | Ile | Glu | Gln | Leu | Cys | Leu | Asp | Leu | Phe | Ala | Ala | Gly | Thr | Asp | Thr |
| | 290 | | | | | 295 | | | | | 300 | | | | |
| Thr | Ser | Asn | Thr | Leu | Glu | Trp | Ala | Met | Ala | Glu | Leu | Leu | Gln | Asn | Pro |
| 305 | | | | | 310 | | | | | 315 | | | | | 320 |
| His | Thr | Leu | Gln | Lys | Ala | Gln | Glu | Glu | Leu | Ala | Gln | Val | Ile | Gly | Lys |
| | | | | 325 | | | | | 330 | | | | | 335 | |
| Gly | Lys | Gln | Val | Glu | Glu | Ala | Asp | Val | Gly | Arg | Leu | Pro | Tyr | Leu | Arg |
| | | | 340 | | | | | 345 | | | | | 350 | | |
| Cys | Ile | Val | Lys | Glu | Thr | Leu | Arg | Ile | His | Pro | Ala | Ala | Pro | Leu | Leu |
| | | | 355 | | | | | 360 | | | | | 365 | | |
| Ile | Pro | Arg | Lys | Val | Glu | Glu | Asp | Val | Glu | Leu | Ser | Thr | Tyr | Ile | Ile |
| | 370 | | | | | 375 | | | | | 380 | | | | |
| Pro | Lys | Asp | Ser | Gln | Val | Leu | Val | Asn | Val | Trp | Ala | Ile | Gly | Arg | Asn |
| 385 | | | | | 390 | | | | | 395 | | | | | 400 |
| Ser | Asp | Leu | Trp | Glu | Asn | Pro | Leu | Val | Phe | Lys | Pro | Glu | Arg | Phe | Trp |
| | | | | 405 | | | | | 410 | | | | | 415 | |
| Glu | Ser | Glu | Ile | Asp | Ile | Arg | Gly | Arg | Asp | Phe | Glu | Leu | Ile | Pro | Phe |
| | | | 420 | | | | | 425 | | | | | 430 | | |
| Gly | Ala | Gly | Arg | Arg | Ile | Cys | Pro | Gly | Leu | Pro | Leu | Ala | Met | Arg | Met |
| | | | 435 | | | | | 440 | | | | | 445 | | |
| Ile | Pro | Val | Ala | Leu | Gly | Ser | Leu | Leu | Asn | Ser | Phe | Asn | Trp | Lys | Leu |
| | 450 | | | | | 455 | | | | | 460 | | | | |
| Tyr | Gly | Gly | Ile | Ala | Pro | Lys | Asp | Leu | Asp | Met | Gln | Glu | Lys | Phe | Gly |
| 465 | | | | | 470 | | | | | 475 | | | | | 480 |
| Ile | Thr | Leu | Ala | Lys | Ala | Gln | Pro | Leu | Leu | Ala | Ile | Pro | Thr | Pro | Leu |
| | | | | 485 | | | | | 490 | | | | | 495 | |

( 2 ) INFORMATION FOR SEQ ID NO:51:

( i ) SEQUENCE CHARACTERISTICS:
        ( A ) LENGTH: 390 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( A ) NAME/KEY: CDS (B) LOCATION: 3..389

(xi) SEQUENCE DESCRIPTION: SEQ ID NO:51:

| | | | | | | | | | | | | | | | | |
|---|---|---|---|---|---|---|---|---|---|---|---|---|---|---|---|---|
| TT | TTG | GAG | TGG | GCA | ATG | GCC | GAA | ATC | TTG | AGG | CAT | CCC | AGA | GTT | TGT | 47 |
| | Leu | Glu | Trp | Ala | Met | Ala | Glu | Ile | Leu | Arg | His | Pro | Arg | Val | Cys | |
| | 1 | | | | 5 | | | | | 10 | | | | | 15 | |
| AGA | AAA | ATG | CAA | AAT | GAG | GCG | ATG | GAG | ATT | GCT | AAT | GGC | AAA | CCA | CAC | 95 |
| Arg | Lys | Met | Gln | Asn | Glu | Ala | Met | Glu | Ile | Ala | Asn | Gly | Lys | Pro | His | |
| | | | | 20 | | | | | 25 | | | | | 30 | | |
| ATC | ACA | GAA | AGT | GAT | TTA | GAT | AAA | ATG | CAC | TAC | TTG | AAA | GCA | GTG | ATC | 143 |
| Ile | Thr | Glu | Ser | Asp | Leu | Asp | Lys | Met | His | Tyr | Leu | Lys | Ala | Val | Ile | |
| | | | 35 | | | | | 40 | | | | | 45 | | | |
| AAA | GAG | ACA | CTT | CGG | CTA | CAT | CCG | CCA | ATA | CCA | TTA | CTC | TCC | CCT | CGT | 191 |
| Lys | Glu | Thr | Leu | Arg | Leu | His | Pro | Pro | Ile | Pro | Leu | Leu | Ser | Pro | Arg | |
| | | 50 | | | | | 55 | | | | | 60 | | | | |
| GAA | TCA | ACT | GAA | GAT | GTT | AAG | ATA | ATG | GAA | TCT | GAC | ATA | GAA | GTC | AAA | 239 |
| Glu | Ser | Thr | Glu | Asp | Val | Lys | Ile | Met | Glu | Ser | Asp | Ile | Glu | Val | Lys | |
| | 65 | | | | | 70 | | | | | 75 | | | | | |
| AAA | CTA | TGG | TCT | TTA | TCA | ATG | CTT | GGG | CAA | TCG | GAA | GAG | ACC | CAG | CAG | 287 |
| Lys | Leu | Trp | Ser | Leu | Ser | Met | Leu | Gly | Gln | Ser | Glu | Glu | Thr | Gln | Gln | |
| 80 | | | | | 85 | | | | | 90 | | | | | 95 | |
| AGT | GGG | ATG | AAC | CAA | GAG | TTT | CGA | CCG | GAG | AGA | TTC | ATG | AAT | TCT | TCT | 335 |
| Ser | Gly | Met | Asn | Gln | Glu | Phe | Arg | Pro | Glu | Arg | Phe | Met | Asn | Ser | Ser | |
| | | | | 100 | | | | | 105 | | | | | 110 | | |
| GTG | GAT | TTC | AAA | GGT | CAT | CTC | TTT | CAA | TTA | CTC | CCC | TTC | GGA | GCC | GGC | 383 |
| Val | Asp | Phe | Lys | Gly | His | Leu | Phe | Gln | Leu | Leu | Pro | Phe | Gly | Ala | Gly | |
| | | | 115 | | | | | 120 | | | | | 125 | | | |
| CGC | AGA | T | | | | | | | | | | | | | | 390 |
| Arg | Arg | | | | | | | | | | | | | | | |

(2) INFORMATION FOR SEQ ID NO:52:

(i) SEQUENCE CHARACTERISTICS:
(A) LENGTH: 129 amino acids
(B) TYPE: amino acid
(D) TOPOLOGY: linear (ii) MOLECULE TYPE: protein (xi) SEQUENCE DESCRIPTION: SEQ ID NO:52:

| | | | | | | | | | | | | | | | |
|---|---|---|---|---|---|---|---|---|---|---|---|---|---|---|---|
| Leu | Glu | Trp | Ala | Met | Ala | Glu | Ile | Leu | Arg | His | Pro | Arg | Val | Cys | Arg |
| 1 | | | | 5 | | | | | 10 | | | | | 15 | |
| Lys | Met | Gln | Asn | Glu | Ala | Met | Glu | Ile | Ala | Asn | Gly | Lys | Pro | His | Ile |
| | | | 20 | | | | | 25 | | | | | 30 | | |
| Thr | Glu | Ser | Asp | Leu | Asp | Lys | Met | His | Tyr | Leu | Lys | Ala | Val | Ile | Lys |
| | | 35 | | | | | 40 | | | | | 45 | | | |
| Glu | Thr | Leu | Arg | Leu | His | Pro | Pro | Ile | Pro | Leu | Leu | Ser | Pro | Arg | Glu |
| | 50 | | | | | 55 | | | | | 60 | | | | |
| Ser | Thr | Glu | Asp | Val | Lys | Ile | Met | Glu | Ser | Asp | Ile | Glu | Val | Lys | Lys |
| 65 | | | | | 70 | | | | | 75 | | | | | 80 |
| Leu | Trp | Ser | Leu | Ser | Met | Leu | Gly | Gln | Ser | Glu | Glu | Thr | Gln | Gln | Ser |
| | | | | 85 | | | | | 90 | | | | | 95 | |
| Gly | Met | Asn | Gln | Glu | Phe | Arg | Pro | Glu | Arg | Phe | Met | Asn | Ser | Ser | Val |
| | | | 100 | | | | | 105 | | | | | 110 | | |
| Asp | Phe | Lys | Gly | His | Leu | Phe | Gln | Leu | Leu | Pro | Phe | Gly | Ala | Gly | Arg |
| | | 115 | | | | | 120 | | | | | 125 | | | |
| Arg | | | | | | | | | | | | | | | |

(2) INFORMATION FOR SEQ ID NO:53:

(i) SEQUENCE CHARACTERISTICS:
(A) LENGTH: 377 base pairs
(B) TYPE: nucleic acid
(C) STRANDEDNESS: single
(D) TOPOLOGY: linear (ii) MOLECULE TYPE: DNA (ix) FEATURE:
(A) NAME/KEY: CDS
(B) LOCATION: 3..377

(xi) SEQUENCE DESCRIPTION: SEQ ID NO:53:

```
TG GCG GAA CTA CTG CGC AAC CCC GAG AAA ATG GCA AAA GCA CAA GAC         47
   Ala Glu Leu Leu Arg Asn Pro Glu Lys Met Ala Lys Ala Gln Asp
    1           5                  10                  15

GAA ATA GAC CGA ATA GTA GGC GAC AAG AAC AAA TCG TTC CAA GAG ACA         95
Glu Ile Asp Arg Ile Val Gly Asp Lys Asn Lys Ser Phe Gln Glu Thr
                 20                  25                  30

GAC ATC TCA AAG TTA CCG TAC ATT CAA GCG GTT GTT AAA GAA ACA TTA        143
Asp Ile Ser Lys Leu Pro Tyr Ile Gln Ala Val Val Lys Glu Thr Leu
             35                  40                  45

AGG CTA CAC CCG CCT GGA CCG TTC CTA ATA CCC CAC AAA GCC GAA AAG        191
Arg Leu His Pro Pro Gly Pro Phe Leu Ile Pro His Lys Ala Glu Lys
         50                  55                  60

GAC GTA AAC TTA AGC CGG TTT TTC ATC CCC GAG GAC GCC CAA GTG TGG        239
Asp Val Asn Leu Ser Arg Phe Phe Ile Pro Glu Asp Ala Gln Val Trp
     65                  70                  75

GTC AAT GTA TGG GCC ATT GGT CGT GAT CCA AGC GTG TGG CGG GTC CCA        287
Val Asn Val Trp Ala Ile Gly Arg Asp Pro Ser Val Trp Arg Val Pro
 80                  85                  90                  95

CTT ACA TTG TGT CCT GAA CGG TTT TTG GAA AAC GAC ATC GAT TTC AAA        335
Leu Thr Leu Cys Pro Glu Arg Phe Leu Glu Asn Asp Ile Asp Phe Lys
                100                 105                 110

GGT ACA GAT TTC GAG CTG ATT CCC TTT GGC GCC GGC CGC ATC                377
Gly Thr Asp Phe Glu Leu Ile Pro Phe Gly Ala Gly Arg Ile
            115                 120                 125
```

(2) INFORMATION FOR SEQ ID NO:54:

(i) SEQUENCE CHARACTERISTICS:
(A) LENGTH: 125 amino acids
(B) TYPE: amino acid
(D) TOPOLOGY: linear (ii) MOLECULE TYPE: protein (xi) SEQUENCE DESCRIPTION: SEQ ID NO:54:

```
Ala Glu Leu Leu Arg Asn Pro Glu Lys Met Ala Lys Ala Gln Asp Glu
 1               5                  10                  15

Ile Asp Arg Ile Val Gly Asp Lys Asn Lys Ser Phe Gln Glu Thr Asp
             20                  25                  30

Ile Ser Lys Leu Pro Tyr Ile Gln Ala Val Val Lys Glu Thr Leu Arg
         35                  40                  45

Leu His Pro Pro Gly Pro Phe Leu Ile Pro His Lys Ala Glu Lys Asp
     50                  55                  60

Val Asn Leu Ser Arg Phe Phe Ile Pro Glu Asp Ala Gln Val Trp Val
 65                  70                  75                  80

Asn Val Trp Ala Ile Gly Arg Asp Pro Ser Val Trp Arg Val Pro Leu
                 85                  90                  95

Thr Leu Cys Pro Glu Arg Phe Leu Glu Asn Asp Ile Asp Phe Lys Gly
            100                 105                 110

Thr Asp Phe Glu Leu Ile Pro Phe Gly Ala Gly Arg Ile
        115                 120                 125
```

5,639,870

73 74

-continued

| | 115 | 120 | 125 |

( 2 ) INFORMATION FOR SEQ ID NO:55:

( i ) SEQUENCE CHARACTERISTICS:
        ( A ) LENGTH: 386 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( A ) NAME/KEY: CDS
        ( B ) LOCATION: 2..385

( x i ) SEQUENCE DESCRIPTION: SEQ ID NO:55:

```
A ATG GCA GAG CTG CTC CGT AAC CCA GAA AAA CTG AAG AAA GCA CAA        46
  Met Ala Glu Leu Leu Arg Asn Pro Glu Lys Leu Lys Lys Ala Gln
  1               5                   10                  15

GTA GAG CTT CAA GAA ATC ATC GGC AGA GGA AAC ACA TTA GAG GAA TCT     94
Val Glu Leu Gln Glu Ile Ile Gly Arg Gly Asn Thr Leu Glu Glu Ser
                20                  25                  30

GAC ATC AGT CGA TTG CCA TAT TTA CAG GCT ATC ATT AAG GAA ACA TTT    142
Asp Ile Ser Arg Leu Pro Tyr Leu Gln Ala Ile Ile Lys Glu Thr Phe
            35                  40                  45

CGG CTA CAC CCA GGA CTG CCA TTA TTG CTA CCT AGG AAA GTT GGT TCA    190
Arg Leu His Pro Gly Leu Pro Leu Leu Leu Pro Arg Lys Val Gly Ser
            50                  55                  60

GAC GTT CAG CTC TTT GGG TTT ACA GTA CCC AAA AAT GCA CAA GTC ATA    238
Asp Val Gln Leu Phe Gly Phe Thr Val Pro Lys Asn Ala Gln Val Ile
        65                  70                  75

ATC AAC GCC TGG GCA ATT GGG AGA GAC CCA GAT TGT TGG CAG AAA CCC    286
Ile Asn Ala Trp Ala Ile Gly Arg Asp Pro Asp Cys Trp Gln Lys Pro
80                  85                  90                  95

AAC TCA TTT GAG CCA GAA AGG TTC CTT GGG TCA CAA ATT GAT GTG AAG    334
Asn Ser Phe Glu Pro Glu Arg Phe Leu Gly Ser Gln Ile Asp Val Lys
                100                 105                 110

GGT CGT GAT TTT GAG CTA ATT CCC TTT GGC GCC GGC CGC AGC ATC TGT    382
Gly Arg Asp Phe Glu Leu Ile Pro Phe Gly Ala Gly Arg Ser Ile Cys
                115                 120                 125

GCC G                                                               386
Ala
```

( 2 ) INFORMATION FOR SEQ ID NO:56:

( i ) SEQUENCE CHARACTERISTICS:
        ( A ) LENGTH: 128 amino acids
        ( B ) TYPE: amino acid
        ( D ) TOPOLOGY: linear ( i i ) MOLECULE TYPE: protein ( x i ) SEQUENCE DESCRIPTION: SEQ ID NO:56:

```
Met Ala Glu Leu Leu Arg Asn Pro Glu Lys Leu Lys Lys Ala Gln Val
1               5                   10                  15

Glu Leu Gln Glu Ile Ile Gly Arg Gly Asn Thr Leu Glu Glu Ser Asp
            20                  25                  30

Ile Ser Arg Leu Pro Tyr Leu Gln Ala Ile Ile Lys Glu Thr Phe Arg
        35                  40                  45

Leu His Pro Gly Leu Pro Leu Leu Leu Pro Arg Lys Val Gly Ser Asp
    50                  55                  60

Val Gln Leu Phe Gly Phe Thr Val Pro Lys Asn Ala Gln Val Ile Ile
65                  70                  75                  80
```

```
Asn Ala Trp Ala Ile Gly Arg Asp Pro Asp Cys Trp Gln Lys Pro Asn
                85                  90                  95

Ser Phe Glu Pro Glu Arg Phe Leu Gly Ser Gln Ile Asp Val Lys Gly
            100                 105             110

Arg Asp Phe Glu Leu Ile Pro Phe Gly Ala Gly Arg Ser Ile Cys Ala
        115                 120                 125
```

(2) INFORMATION FOR SEQ ID NO:57:

(i) SEQUENCE CHARACTERISTICS:
        (A) LENGTH: 120 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: CDS
        (B) LOCATION: 1..120

(xi) SEQUENCE DESCRIPTION: SEQ ID NO:57:

```
TTG GAG TGG GCA ATG GCA GAA CTT CTA CGC AAC CCG CAC ACC ATG GCC    48
Leu Glu Trp Ala Met Ala Glu Leu Leu Arg Asn Pro His Thr Met Ala
 1               5                  10                  15

AAA GCA AAA GAG GAG CTT AAA GAC GTT ATC GGC AAA GAA AAA CTT GTA    96
Lys Ala Lys Glu Glu Leu Lys Asp Val Ile Gly Lys Glu Lys Leu Val
            20                  25                  30

GAT GAA GCT GAC ATT TTC GAG ACT                                   120
Asp Glu Ala Asp Ile Phe Glu Thr
        35                  40
```

(2) INFORMATION FOR SEQ ID NO:58:

(i) SEQUENCE CHARACTERISTICS:
        (A) LENGTH: 40 amino acids
        (B) TYPE: amino acid
        (D) TOPOLOGY: linear (ii) MOLECULE TYPE: protein (xi) SEQUENCE DESCRIPTION: SEQ ID NO:58:

```
Leu Glu Trp Ala Met Ala Glu Leu Leu Arg Asn Pro His Thr Met Ala
 1               5                  10                  15

Lys Ala Lys Glu Glu Leu Lys Asp Val Ile Gly Lys Glu Lys Leu Val
            20                  25                  30

Asp Glu Ala Asp Ile Phe Glu Thr
        35                  40
```